United States Patent [19]

Lippman et al.

[11] Patent Number: 5,578,482

[45] Date of Patent: Nov. 26, 1996

[54] LIGAND GROWTH FACTORS THAT BIND TO THE ERBB-2 RECEPTOR PROTEIN AND INDUCE CELLULAR RESPONSES

[75] Inventors: Marc E. Lippman, Bethesda; Ruth Lupu, Gaithersburg, both of Md.

[73] Assignee: Georgetown University, Washington, D.C.

[21] Appl. No.: 96,277

[22] Filed: Jul. 26, 1993

Related U.S. Application Data

[63] Continuation-in-part of Ser. No. 875,788, Apr. 29, 1992, abandoned, which is a continuation-in-part of Ser. No. 640,497, Jan. 14, 1991, abandoned, and a continuation-in-part of Ser. No. 917,988, Jul. 24, 1992, abandoned, which is a continuation-in-part of Ser. No. 872,114, Apr. 22, 1992, abandoned, which is a continuation of Ser. No. 528,438, May 25, 1990, abandoned.

[51] Int. Cl.$^6$ .................. C12N 1/38; C12N 5/26
[52] U.S. Cl. ............ 435/240.1; 435/244; 530/350; 530/399; 514/21
[58] Field of Search .................. 530/350, 324–331, 530/399; 514/2, 8, 12, 21; 435/244, 240.1

[56] References Cited

U.S. PATENT DOCUMENTS

| | | |
|---|---|---|
| 4,705,677 | 11/1987 | Makari . |
| 4,774,321 | 9/1988 | Rosner et al. . |
| 4,859,609 | 8/1989 | Dull et al. . |
| 4,968,603 | 11/1990 | Slamon et al. . |
| 4,993,294 | 6/1990 | Waterfield et al. . |
| 5,015,571 | 5/1991 | Niman et al. ............ 435/7.92 |
| 5,030,565 | 7/1991 | Niman et al. . |
| 5,030,576 | 7/1991 | Dull et al. . |
| 5,115,096 | 5/1992 | Shoyab et al. ............ 530/322 |
| 5,155,027 | 10/1992 | Sledziewski et al. . |
| 5,183,884 | 2/1993 | Kraus et al. . |
| 5,288,477 | 2/1994 | Bacus .................... 435/7.1 |

FOREIGN PATENT DOCUMENTS

| | | |
|---|---|---|
| 0244221 | 4/1987 | European Pat. Off. . |
| 0354808 | 2/1990 | European Pat. Off. . |
| WO85/02467 | 6/1985 | WIPO . |
| WO90/14357 | 11/1990 | WIPO . |

OTHER PUBLICATIONS

Lupu, et al., *Chemical Abstracts*, 113:476 (1990) (Abst. 228667K) (*Science* (1990) 249:1552–1555).

Bacus, et al., "A Ligand For The erbB–2 Oncogene Product (gp30) Induces Differentiation of Human Breast Cancer Cells," *Lab. Invest.*, 66:12A (1992) (Abstr. 60).

Bacus, et al., "A Ligand For the erbB–2 Oncogene Product (gp30) Induces Differentiation of Human Breast Cancer Cells," *Proceedings of the American Assn. for Cancer Res.*, 33:365 (1992) (Abstr. 2181).

Beug, et al., "Production and Characterization of Antisera Specific for the erb–Portion of p. 75, the Presumptive Transforming Protein of Avian Erythroblastosis Virus," *Virology* (1981) 111:201–210.

Sherwin, et al., "High∝Molecular–Weight Transforming Growth Factor Activity in the Urine of Patients with Disseminated Cancer," *Cancer Research* (1983) 43:403–407.

(List continued on next page.)

*Primary Examiner*—Kay K. A. Kim, Ph.D.
*Attorney, Agent, or Firm*—Banner & Allegretti, Ltd.

[57] ABSTRACT

The present invention relates to erbB-2 ligands and functional derivatives thereof which are capable of binding to the erbB-2 oncogene product. The present invention further pertains to anti-ligand molecules capable of recognizing and binding to the erbB-2 ligand molecule and to screening assays for such ligands. The present invention additionally relates to uses for the erbB-2 ligand, the anti-ligand molecules and the screening assays.

A method for inhibiting the growth of adenocarcinoma cells in a human, which cells overexpress the oncogene erbB-2, which entails administering to said human an amount of a 30 kDa glycoprotein effective to inhibit the growth of said cells.

5 Claims, 23 Drawing Sheets

OTHER PUBLICATIONS

Ullrich, et al., "Human Epidermal Growth Factor Receptor cDNA Sequence and Aberrant Expression of the Amplified Gene in A431 Epidermoid Carcinoma Cells," *Nature* (1984) 309:418–425.

Schechter, et al., "The neu Oncogene: an erbB–2–Related Gene Encoding a 185,000–$M_r$, Tumour Antigen," *Nature* (1984) 312:513–516.

Coussens, et al., "Tyrosine Kinase Receptor with Extensive Homology to EGF Receptor Shares Chromosomal Location with neu Oncogene," *Science* (1985) 230:1132–1139.

Bargmann, et al., "The neu Oncogene Encodes an Epidermal Growth Factor Receptor–Related Protein," *Nature* (1986) 319:226–230.

Yamamoto, et al., "Similarity of Protein Encoded By the Human C–erb–B–2 Gene to Epidermal Growth Factor Receptor," *Nature* (1986) 319:230–234.

Lippman, et al., "Autocrine and Paracrine Growth Regulation of Human Breast Cancer," *Breast Cancer Research and Treatment* (1986) 7:59–70.

Dickson, et al., "Characterization of Estrogen Responsive Transforming Activity in Human Breast Cancer Cell Lines," *Cancer Research* (1986) 46:1707–1713.

Gentry, et al., "Characterization of Site–Specific Antibodies to the erbB Gene Product and EGF Receptor: Inhibition of Tyrosine Kinase Activity," *Virology* (1986) 152:421–431.

Stromberg, et al., "Human A673 Cells Secrete High Molecular Weight EGF–Receptor Binding Growth Factors that Appear to be Immunologically Unrelated to EGF or TGF–α," *Journal of Cellular Biochemistry* (1986) 32:247–259.

Stern, et al., "Oncogenic Activation of $p185^{neu}$ Stimulates tyrosine Phosphorylation *In Vivo,*" *Molecular and Cellular Biology* (1988) 8:3969–3973.

King, et al., "EGF Binding To Its Receptor Triggers A Rapid Tyrosine Phosphorylation of the erbB–2 Protein in the Mammary Tumor Cell Line SK–BR–3", *The EMBO Journal* (1988) 7:1647–1651.

Lax, et al., "Chicken Epidermal Growth Factor (EGF) Receptor: cDNA Cloning, Expression in Mouse Cells, and Differential Binding of EGF and Transforming Growth Factor Alpha," *Mol. Cell. Biol.* (1988) 8:1970–1978.

Stern, et al., "EGF–Stimulated Tyrosine Phosphorylation of p185neu: A Potential Model for Receptor Interactions," *The EMBO Journal* (1988) 7:995–1001.

Hudziak, et al., "$p185^{HER2}$ Monoclonal Antibody Has Antiproliferative Effects *In Vitro* and Sensitizes Human Breast Tumor Cells to Tumor Necrosis Factor," *Mol. Cell. Biol.* (1989) 9:1165–1172.

Harsh, IV, et al., "Oncogene–Related Growth Factors and Growth Factor Receptors In Human Malignant Glioma–Derived Cell Lines,", *Journal of Neuro–Oncology* (1989) 7:47–56.

Lee, et al., "HER2 Cytoplasmic Domain Generates Normal Mitogenic and Transforming Signals In a Chimeric Receptor," *The EMBO Journal* (1989) 8;167–173.

Schneider, et al., "Differential Expression of the c–erbB–3 Gene in Human Small Cell and Non–Small Cell Lung Cancer," *Cancer Research* (1989) 49:4968–4971.

Maguire, et al., "Distribution of neu(c–erbB–2) Protein in Human Skin," *Journal of Investigative Dermatology* (1989) 92:786–789.

Slamon, et al., "Studies of the HER–2/neu Proto–oncogene in Human Breast and Ovarian Cancer", *Science* (1989) 244:707–712.

Yarden, et al., "Experimental Approaches to Hypothetical Hormones: Detection of a Candidate Ligand of the Neu Protooncogene," *Proc. Natl. Acad. Sci., USA* (1989) 86:3179–3183.

Falck, et al., "c–erbB–2 Oncogene Product Staining in Gastric Adenocarcinoma. An Immunohistochemical Study," *Journal of Pathology* (1989) 159:107–111.

Oda, et al., "DNA Ploidy Pattern and Amplification of ERBB and ERBB2 Genes in Human Gastric Carcinomas," *Virchows Archiv B Cell Pathol.* (1990) 58:273–277.

Petch, et al., "A Truncated, Secreted Form of the Epidermal Growth Factor Receptor Is Encoded by an Alternatively Spliced Transcript in Normal Rat Tissue," *Mol. Cell. Biol.* (1990) 10:2973–2982.

Lupu, et al., "Direct Interaction of a Ligand for the erbB2 Oncogene Product with the EGF Receptor and $p185^{erbB2}$", *Science* (1990) 249:1552–1555.

Yarden, Yosef, "Agonistic Antibodies Stimulate the Kinase Encoded by the neu Protooncogens in Living Cells But the Oncogenic Mutant Is Constitutively Active," *Proc. Natl. Acad. Sci. USA* (1990) 87:2569–2573.

Lin, et al., "Insulin and Epidermal Growth Factor Stimulate Phosphorylation of $p185^{HER-2}$ In the Breast Carcinoma Cell Line, BT474," *Molecular and Cellular Endocrinology* (1990) 69:111–119.

Alper, et al., "The Presence of cerbB–2 Gene Product–Related Protein In Culture Medium Conditioned by Breast Cancer Cell Line SK–BR–3," *Cell Growth & Differentiation* (1990) 1:591–599.

Koskinen, et al., "Similar Early Gene Responses to Ligand–Activated EGFR and neu tyrosine kinase in NIH3T3 cells," *Oncogene* (1990) 5:615–618.

Shirahata, et al., "Ras and Neu oncogenes Reverse Serum Inhibition and Epidermal Growth Factor Dependence of Serum–Free Mouse Embryo Cells," *Journal of Cellular Physiology* (1990) 144:69–76.

Langton, et al., "An Antigen Immunologically Related to the External Domain of gp185 is Shed from Nude Mouse Tumors Overexpressing the c–erbB–2 (HER–2/neu) Oncogene," *Cancer Research* (1991) 51:2593–2598.

Maihle, et al., "Native Avian c–erbB gene expresses a Secreted Protein Product Corresponding to the Ligand–Binding Domain of the Receptor," *Proc. Natl. Acad. Sci. USA* (1991) 88:1825–1829.

Lupu, et al., "A Novel TGFα–Related Growth Factor Interacts Directly With EGF Receptor and erbB–2," *Proceedings of the American Assn. for Cancer Res.*, vol. 31, 1990 (Abstr. 491).

Linsley, et al., "Detection of Larger Polypeptides Structurally and Functionally Related to Type I Transforming Growth Factor," *Proc. Natl. Acad. Sci. USA* (1985) 82:356–360.

Kokai, et al., "Phosphorylation Process Induced by Epidermal Growth Factor Alters the Oncongenic and Cellular neu (NGL) Gene Products," *Proc. Natl. Acad. Sci. USA* (1988) 85:5389–5393.

Goldman, et al., "Heterodimerization of the erbB–1 and erbB–2 Receptors in Human Breast Carcinoma Cells: A Mechanism for Receptor Transregulation," *Biochemistry* (1990) 29:11024–11028.

Yarden, "Receptor–Like Oncogenes: Functional Analysis Through Novel Experimental Approaches," *Molecular Immunol.* (1990) 27:1319–1324.

Yarden, et al., "Biochemical Analysis of the Ligand for the neu Oncogenic Receptor," *Biochemistry* (1991) 30:3543–3550.

Lupu, et al., "The Role of erbB–2 and its Ligands in Growth Control of Malignant Breast Epithelium," in *Multistage Carcinogenesis,* Harris, et al. (eds.), CRC Press, Boca Raton, (1992) pp. 49–60.

Stancovski, et al., "Mechanistic Aspects of the Opposing Effects of Monoclonal Antibodies to the erbB2 Receptor on Tumor Growth," *Proc. Natl. Acad. Sci USA* (1991) 88:8691–8695.

Lupu, et al., "The Role of erbB–2 and its Ligands in Growth Control of Malignant Breast Epithelium," *Journal of Steroid Biochemistry & Molecular Biology* (1992) 43:229–236.

Lupu, et al., "Characterization of a Growth Factor that Binds Exclusively to the erbB–2 Receptor and Induces Cellular Responses," *Proc. Natl. Acad. Sci. USA* (1992) 89:2287–2291.

Peles, et al., "Isolation of the Neu/HER–2 Stimulatory Ligand: A 44 kd Glycoprotein that Induces Differentiation of Mammary Tumor Cells," *Cell* (1992) 59:1–20.

Bano, et al., "Production and Characterization of Mammary–Derived Growth Factor 1 in Mammary Epithelial Cell Lines," *Biochemistry* (1992) 31:610–616.

Bacus, et al., "Tumor–inhibitory Monoclonal Antibodies to the HER–2/Neu Receptor Induce Differentiation of Human Breast Cancer Cells," *Cancer Research* (1992) 52:2580–2589.

Holmes, et al., "Identification of Heregulin, a Specific Activator of p185$^{erb2}$", *Science* (1992) 256:1205–1210.

Bacus, et al., "A Ligand For the erbB–2 Oncogene Product (gp30) Induces Differentiation of Human Breast Cancer Cells," *Cell Growth Differential* (1992) 3:401–411.

Lupu, et al., "Purification and Characterization of a Novel Growth Factor From Human Breast Cancer Cells," *Biochemstry* (1992) 31:7330–7340.

Xu, et al., "Antibody–Induced Growth Inhibition is Mediated Through Immunochemically and Functionally Distinct Epitopes on the Extracellular Domain of the c–erbB–2 (HER–2/neu) Gene Product," *International Journal of Cancer* (1993) 53:401–408.

Noguchi, et al., "Biological Consequences of Overexpression of a Transfected c–erbB–2 Gene in Immortalized Human Bronchial Epithelial Cells," Cancer Research (1993) 53:2035–2043.

| PEAK NUMBER | PROTEIN SEQUENCE | HOMOLOGY TO HEREGULIN α |
|---|---|---|
| 1 | 10KGKGKGKKXERGRGKKPGSAAXPQSPALP36 | 94 % |
| 2 | 53LVLRCETSSTYSSLAFKWFKNG74 | 90.4 % |
| 3 | 118LGNDSASANITIVESNEIITGNMPA141 | 98 % |
| 4 | 106DSGEYMCKVIS116 | 100 % |
| 5 | 179LVKCAEKEKTFCVNGGECFMVKD203 | 100 % |

FIG. 18A

```
   1    CCGATCCGAG CCCTTGGACC AAACTCGCCT GCGCCGAGAG CCGTCCGCGT AGAGCGCTCC
  61    GTCTCCGGCG AGATGTCCGA GCGCAAAGAA GGCAGAGGCA AAGGGAAGGG CAAGAAGAAG
 121    GAGCGAGGCT CCGGCAAGAA GCCGGAGTCC GCGGCGGGCA GCCAGAGCCC AGCCTTGCCT
 181    CCCCGATTGA AAGAGATGAA AAGCCAGGAA TCGGCTGCAG GTTCCAAACT AGTCCTTCGG
 241    TGTGAAACCA GTTCTGAATA CTCCTCTCTC AGATTCAAGT GGTTCAAGAA TGGGAATGAA
 301    TTGAATCGAA AAAACAAACC ACAAAATATC AAGATACAAA AAAAGCCAGG GAAGTCAGAA
 361    CTTCGCATTA ACAAAGCATC ACTGGCTGAT TCTGGAGAGT ATATGTGCAA AGTGATCAGC
 421    AAATTAGGAA ATGACAGTGC CTCTGCCAAT ATCACCATCG TGGAATCAAA CGAGATCATC
 481    ACTGGTATGC CAGCCTCAAC TGAAGGAGCA TATGTGTCTT CAGAGTCTCC CATTAGAATA
 541    TCAGTATCCA CAGAAGGAGC AAATACTTCT TCATCTACAT CTACATCCAC CACTGGGACA
 601    AGCCATCTTG TAAAATGTGC GGAGAAGGAG AAAACTTTCT GTGTGAATGG AGGGGAGTGC
 661    TTCATGGTGA AAGACCTTTC AAACCCCTCG AGATACTTGT GCAAGTGCCA ACCTGGATTC
 721    ACTGGAGCAA GATGTACTGA GAATGTGCCC ATGAAAGTCC AAAACCAAGA AAAGGCGGAG
 781    GAGCTGTACC AGAAGAGAGT GCTGACCATA ACCGGCATCT GCATCGCCCT CCTTGTGGTC
 841    GGCATCATGT GTGTGGTGGC CTACTGCAAA ACCAAGAAAC AGCGGAAAAA GCTGCATGAC
 901    CGTCTTCGGC AGAGCCTTCG GTCTGAACGA ACAATATGA TGAACATTGC CAATGGGCCT
 961    CACCATCCTA ACCCACCCCC CGAGAATGTC CAGCTGGTGA ATCAATACGT ATCTAAAAAC
1021    GTCATCTCCA GTGAGCATAT TGTTGAGAGA GAAGCAGAGA CATCCTTTTC CACCAGTCAC
1081    TATACTTCCA CAGCCCATCA CTCCACTACT GTCACCCAGA CTCCTAGCCA CAGCTGGAGC
1141    AACGGACACA CTGAAAGCAT CCTTTCCGAA AGCCACTCTG TAATCGTGAT GTCATCCGTA
1201    GAAAACAGTA GGCACAGCAG CCCAACTGGG GGCCCAAGAG GACGTCTTAA TGGCACAGGA
1261    GGCCCTCGTG AATGTAACAG CTTCCTCAGG CATGCCAGAG AAACCCCTGA TTCCTACCGA
1321    GACTCTCCTC ATAGTGAAAG GTATGTGTCA GCCATGACCA CCCCGGCTCG TATGTCACCT
1381    GTAGATTTCC ACACGCCAAG CTCCCCCAAA TCGCCCCCTT CGGAAATGTC TCCACCCGTG
1441    TCCAGCATGA CGGTGTCCAT GCCTTCCATG GCGGTCAGCC CCTTCATGGA AGAAGAGAGA
1501    CCTCTACTTC TCGTGACACC ACCAAGGCTG CGGGAGAAGA AGTTTGACCA TCACCCTCAG
1561    CAGTTCAGCT CCTTCCACCA CAACCCCGCG CATGACAGTA ACAGCCTCCC TGCTAGCCCC
1621    TTGAGGATAG TGGAGGATGA GGAGTATGAA ACGACCCAAG AGTACGAGCC AGCCCAAGAG
1681    CCTGTTAAGA AACTCGCCAA TAGCCGGCGG GCCAAAAGAA CCAAGCCCAA TGGCCACATT
1741    GCTAACAGAT TGGAAGTGGA CAGCAACACA AGCTCCCAGA GCAGTAACTC AGAGAGTGAA
1801    ACAGAAGATG AAAGAGTAGG TGAAGATACG CCTTTCCTGG CATACAGAA CCCCCTGGCA
1861    GCCAGTCTTG AGGCAACACC TGCCTTCCGC CTGGCTGACA GCAGGACTAA CCCAGCAGGC
1921    CGCTTCTCGA CACAGGAAGA AATCCAGGCC AGGCTGTCTA GTGTAATTGC TAACCAAGAC
1981    CCTATTGCTG TATAAAACCT AAATAAACAC ATAGATTCAC CTGTAAAACT TTATTTTATA
2041    TAATAAAGTA TTCCACCTTA AATTAAACAA TTTATTTTAT TTTAGCAGTT CTGCAAATAG
2101    AAAACAGGAA AAAAACTTTT ATAAATTAAA TATATGTATG TAAAAATGAA AAAAAAAAA
2161    AAAA
```

FIG. 18B

```
   1    GGGACAAACT TTTCCCAAAC CCGATCCGAG CCCTTGGACC AAACTCGCCT GCGCCGAGAG
  61    CCGTCCGCGT AGAGCGCTCC GTCTCCGGCG AGATGTCCGA GCGCAAAGAA GGCAGAGGCA
 121    AAGGGAAGGG CAAGAAGAAG GAGCGAGGCT CCGGCAAGAA GCCGGAGTCC GCGGCGGGCA
 181    GCCAGAGCCC AGCCTTGCCT CCCCAATTGA AAGAGATGAA AAGCCAGGAA TCGGCTGCAG
 241    GTTCCAAACT AGTCCTTCGG TGTGAAACCA GTTCTGAATA CTCCTCTCTC AGATTCAAGT
 301    GGTTCAAGAA TGGGAATGAA TTGAATCGAA AAAACAAACC ACAAAATATC AAGATACAAA
 361    AAAAGCCAGG GAAGTCAGAA CTTCGCATTA ACAAAGCATC ACTGGCTGAT TCTGGAGAGT
 421    ATATGTGCAA AGTGATCAGC AAATTAGGAA ATGACAGTGC CTCTGCCAAT ATCACCATCG
 481    TGGAATCAAA CGAGATCATC ACTGGTATGC CAGCCTCAAC TGAAGGAGCA TATGTGTCTT
 541    CAGAGTCTCC CATTAGAATA TCAGTATCCA CAGAAGGAGC AAATACTTCT TCATCTACAT
 601    CTACATCCAC CACTGGGACA AGCCATCTTG TAAAATGTGC GGAGAAGGAG AAAACTTTCT
 661    GTGTGAATGG AGGGGAGTGC TTCATGGTGA AAGACCTTTC AAACCCCTCG AGATACTTGT
 721    GCAAGTGCCC AAATGAGTTT ACTGGTGATC GCTGCCAAAA CTACGTAATG GCCAGCTTCT
 781    ACAAGCATCT TGGGATTGAA TTTATGGAGG CGGAGGAGCT GTACCAGAAG AGAGTGCTGA
 841    CCATAACCGG CATCTGCATC GCCCTCCTTG TGGTCGGCAT CATGTGTGTG GTGGCCTACT
 901    GCAAAACCAA GAAACAGCGG AAAAAGCTGC ATGACCGTCT TCGGCAGAGC CTTCGGTCTG
 961    AACGAAACAA TATGATGAAC ATTGCCAATG GCCTCACCA TCCTAACCCA CCCCCCGAGA
1021    ATGTCCAGCT GGTGAATCAA TACGTATCTA AAAACGTCAT CTCCAGTGAG CATATTGTTG
1081    AGAGAGAAGC AGAGACATCC TTTTCCACCA GTCACTATAC TTCCACAGCC CATCACTCCA
1141    CTACTGTCAC CCAGACTCCT AGCCACAGCT GGAGCAACGG ACACACTGAA AGCATCCTTT
1201    CCGAAAGCCA CTCTGTAATC GTGATGTCAT CCGTAGAAAA CAGTAGGCAC AGCAGCCCAA
1261    CTGGGGGCCC AAGAGGACGT CTTAATGGCA CAGGAGGCCC TCGTGAATGT AACAGCTTCC
1321    TCAGGCATGC CAGAGAAACC CCTGATTCCT ACCGAGACTC TCCTCATAGT GAAAGGTATG
1381    TGTCAGCCAT GACCACCCCG GCTCGTATGT CACCTGTAGA TTTCCACACG CCAAGCTCCC
1441    CCAAATCGCC CCCTTCGGAA ATGTCTCCAC CCGTGTCCAG CATGACGGTG TCCATGCCTT
1501    CCATGGCGGT CAGCCCCTTC ATGGAAGAAG AGAGACCTCT ACTTCTCGTG ACACCACCAA
1561    GGCTGCGGGA GAAGAAGTTT GACCATCACC CTCAGCAGTT CAGCTCCTTC CACCACAACC
1621    CCGCGCATGA CAGTAACAGC CTCCCTGCTA GCCCCTTGAG GATAGTGGAG GATGAGGAGT
1681    ATGAAACGAC CCAAGAGTAC GAGCCAGCCC AAGAGCCTGT TAAGAAACTC GCCAATAGCC
1741    GGCGGGCCAA AGAACCAAG CCCAATGGCC ACATTGCTAA CAGATTGGAA GTGGACAGCA
1801    ACACAAGCTC CCAGAGCAGT AACTCAGAGA GTGAAACAGA AGATGAAAGA GTAGGTGAAG
1861    ATACGCCTTT CCTGGGCATA CAGAACCCCC TGGCAGCCAG TCTTGAGGCA CACCTGCCT
1921    TCCGCCTGGC TGACAGCAGG ACTAACCCAG CAGGCCGCTT CTCGACACAG GAAGAAATCC
1981    AGGCCAGGCT GTCTAGTGTA ATTGCTAACC AAGACCCTAT GCTGTATAA AACCTAAATA
2041    AACACATAGA TTCACCTGTA AAACTTTATT TTATATAATA AAGTATTCCA CCTTAAATTA
2101    AACAATTTAT TTTATTTTAG CAGTTCTGCA AATAGAAAAC AGGAAAAAAA CTTTTATAAA
2161    TTAAATATAT GTATGTAAAA ATGAAAAAAA AAAAAAAA
```

FIG. 23A

```
                    1                          7
                    |                          |
          Lys  Gly  Lys  Gly  Lys  Lys  Xaa m-RNA 5'  AAA  GG-  AAA  GG-  AAA  AAA  --  3'
               G         G         G    G

Probe 3'  TTT  CC-  TTT  CC-  TTT  TTT  --  5'
           C         C         C    C
```

- Probe synthesis method is: MDT.
- Probe length is: 20 bases.
- Number of combinations is: 256

```
                         3                          9
                         |                          |
               Gly  Glu  Tyr  Met  Cys  Lys  Val m-RNA 5'  GG-  GAA  UAU  AUG  UGU  AAA  GU  3'
          G         C              C    G

Probe 3'  CC-  CTT  ATA  TAC  ACA  TTT  CA  5'
          C         G              G    C
```

- Probe synthesis method is: MDT.
- Probe length is: 20 bases.
- Number of combinations is: 64

FIG. 23B

```
          10        20        30        40        50        60        70
          |         |         |         |         |         |         |
AAAGGGAAGGGCAAGAAGAAGGAGCGAGGCTCCGGCAAGAAGCCGGAGTCCGCGGCGGGCAGCCAGAGCCCA
  K  G  K  G  K  K  E  R  G  S  G  K  K  P  E  S  A  A  G  S  Q  S  P 80        90        100       110       120       130       140
          |         |         |         |         |         |         |
GCCTTGCCTCCCCGATTGAAAGAGATGAAAAGCCAGGAATCGGCTGCAGGTTCCAAACTAGTCCTTCGGTGT
  A  L  P  P  R  L  K  E  M  K  S  Q  E  S  A  A  G  S  K  L  V  R  C 150       160       170       180       190       200       210
          |         |         |         |         |         |         |
GAAACCAGTTCTGAATACTCCTCTCTCAGATTCAAGTGGTTCAAGAATGGGAATGAATTGAATCGAAAAAAC
  E  T  S  S  E  Y  S  S  L  R  F  K  W  F  K  N  G  N  E  L  N  R  K  N 220       230       240       250       260       270       280
          |         |         |         |         |         |         |
AAACCACAAAATATCAAGATACAAAAAAAGCCAGGGAAGTCAGAACTTCGCATTAACAAAGCATCACTGGCT
  K  P  Q  N  I  K  I  Q  K  K  P  G  K  S  E  L  R  I  N  K  A  S  L  A 290       300       310       320       330       340       350       360
   |         |         |         |         |         |         |         |
GATTCTGGAGAGTATATGTGCAAAGTGATCAGCAAATTAGGAAATGACAGTGCCTCTGCCAATATCACCATC
  D  S  G  E  Y  M  C  K  V  I  S  K  L  G  N  D  S  A  S  A  N  I  T  I 370       380       390       400       410       420       430
          |         |         |         |         |         |         |
GTGGAATCAAACGAGATCATCACTGGTATGCCAGCCTCAACTGAAGGAGCATATGTGTCTTCAGAGTCTCCC
  V  E  S  N  E  I  I  T  G  M  P  A  S  T  E  G  A  Y  V  S  S  E  S  P 440       450       460       470       480
          |         |         |         |         |
ATTAGAATATCAGTATCCACAGAAGGAGAGTATATGTGCAAAGTGATCAGC
  I  R  I  S  V  S  T  E  G  E  Y  M  C  K  V  I  S
```

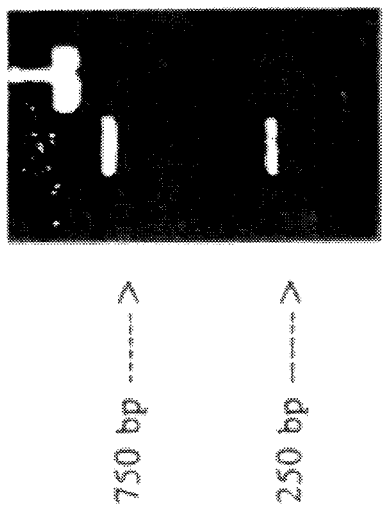
FIG. 23C(2)
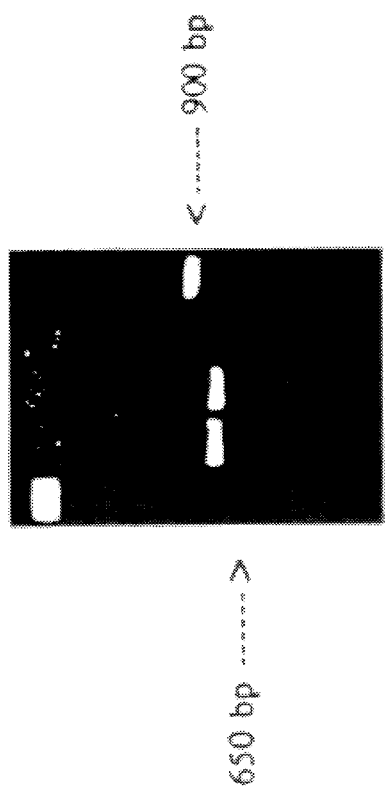
FIG. 23C(1)

LIGAND GROWTH FACTORS THAT BIND TO THE ERBB-2 RECEPTOR PROTEIN AND INDUCE CELLULAR RESPONSES

The present application is a continuation-in-part of U.S. application Ser. No. 07/875,788, filed Apr. 29, 1992, now abandoned, which is a continuation-in-part of U.S. application Ser. No. 07/640,497, filed Jan. 14, 1991, now abandoned, and a continuation-in-part of U.S. application Ser. No. 07/917,988, filed Jul. 24, 1992, now abandoned, which is a continuation-in-part of U.S. application Ser. No. 07/872,114, filed Apr. 22, 1992, now abandoned, which is a continuation of U.S. application Ser. No. 07/528,438, filed May 25, 1990, now abandoned. All of these applications are incorporated by reference in their entirety.

BACKGROUND OF THE INVENTION

1. Field of the Invention

The present invention relates to a growth factor which interacts with the human oncogene erbB-2, and which stimulates as well as inhibits the growth of cells overexpressing this oncogene. A ligand is described which is capable of binding to the expression product of the erbB-2 oncogene. The present invention additionally relates to anti-ligand molecules capable of recognizing and binding to the erbB-2 ligand molecule and to screening assays for such ligands. The present invention further relates to uses for the erbB-2 ligand, the anti-ligand molecules and the screening assay. Furthermore, the invention relates to a cloned gene capable of expressing the erbB-2 ligand of the present invention.

2. Description of the Related Art

Carcinogenesis is believed to be a multi-step process of alteration of genes which are involved in the growth control of cells. A variety of proto-oncogenes and oncogenes have been implicated in the activation of tumor cells as regulating factors. For example, oncogenic protein kinases are believed to induce cellular transformation through either inappropriate or excessive protein phosphorylation, resulting in the uncontrolled growth of malignant neoplasms. See Wrba, F., et al., *Histopathology*, 15:71–76 (1989).

One group of proto-oncogenes encodes cellular growth factors or their receptors. The c-erbB-1 gene encodes the epidermal growth factor or its receptors. The c-sis gene encodes the B-chain of the platelet-derived growth factor. The c-fms gene encodes a related or identical molecule for the receptor of the granulocyte-macrophage colony stimulating factor. A fourth member of this group of proto-oncogenes, called neu was identified in ethylnitrosourea-induced rat neuroblastomas.

The human counterpart of neu, called HER-2/neu or c-erbB-2, has been sequenced and mapped to the chromosomal locus 17q21. See Schneider, P.M., et al., *Cancer Research*, 49:4968–4971 (Sep. 15, 1989). The HER-2/neu or c-erbB-2 oncogene belongs to the erbB-like oncogene group, and is related to, but distinct from the epidermal growth factor receptor (EGFR). The c-erbB-2 oncogene is known to express a 185 kDa transmembrane glycoprotein ($p185^{erbB-2}$). The expressed protein has been suggested to be a growth factor receptor due to its structural homology with EGFR. However, known EGFR ligands, such as EGF or TGFα, do not bind to $p185^{erbB-2}$.

The oncogene has been demonstrated to be implicated in a number of human adenocarcinomas leading to elevated levels of expression of the p185 protein product. For example, the oncogene has been found to be amplified in breast, ovarian, gastric and even lung adenocarcinomas. Furthermore, the amplification of the c-erbB-2 oncogene has been found in many cases to be a significant, if not the most significant, predictor of both overall survival time and time to relapse in patients suffering from such forms of cancer. Carcinoma of the breast and ovary account for approximately one-third of all cancers occurring in women and together are responsible for approximately one-fourth of cancer-related deaths in females. Significantly, the c-erbB-2 oncogene has been found to be amplified in 25 to 30% of human primary breast cancers. See Slamon, D., et al., *Science*, 244, 707–712 (May 12, 1989).

Although ligands for EGFR are known, namely EGF and TGFα, few ligands for the oncogene-encoding transmembrane proteins such as erbB-2, ros, etc., have been characterized. Transforming growth factor ligands belong to a family of heat and acid-stable polypeptides which allow cells to assume a transformed morphology and form progressively growing colonies in anchorage-independent growth assays (DeLarco, et al., *Proc. Natl. Acad. Sci. USA*, 75:4001–4005 (1978); Moses, et al., *Cancer Res.*, 41:2842–2848 (1981); Ozanne, et al., *J. Cell. Physiol.*, 105:163–180 (1980); Roberts, et al., *Proc. Natl. Acad. Sci. USA*, 77:3494–3498 (1980)). The epidermal growth factor receptor (EGFR) and its physiologic ligands, epidermal growth factor (EGF) and transforming growth factor α (TGFα), play a prominent role in the growth regulation of many normal and malignant cell types (Carpenter, G., *Annu. Rev., Biochem.*, 56:881–914 (1987)).

One role the EGF receptor system may play in the oncogenic growth of cells is through autocrine-stimulated growth. If cells express the EGFR and secrete EGF and/or TGFα, then such cells could stimulate their own growth. Since some human breast cancer cell lines and tumors express EGFR (Osborne, et al., *J. Clin. Endo. Metab.*, 55:86–93 (1982); Fitzpatrick, et al., *Cancer Res.*, 44:3442–3447 (1984); Filmus, et al., *Biochem, Biophys. Res. Commun.*, 128:898–905 (1985); Davidson, et al., *Mol. Endocrinol*, 1:216–223 (1987); Sainsbury, et al., *Lancet*, 1:1398–1402 (1987); Perez, et al., *Cancer Res. Treat.*, 4:189–193 (1984)) and secrete TGFα (Bates, et al., *Cancer Res.*, 46:1707–1713 (1986); Bates, et al., *Mol. Endocrinol*, 2:543–555 (1988)), an autocrine growth stimulatory pathway has been proposed in breast cancer (Lippman, et al., *Breast Cancer Res. Treat.*, 7:59–70 (1986)).

The erbB-2 proto-oncogene amplification has been found in breast, ovarian, gastric, salivary gland, and in non-small cell carcinomas of the lung (King, et al., *Science*, 229:974 (1985); Slamon, et al., *Science*, 244:707 (1989); Yokota, et al., *Lancet*, 1:765 (1986); Fukushige, et al., *Mol, Cell, Biol.*, 6:955 (1986); Semba, et al., *Proc. Natl, Acad, Sci. USA*, 82:6497 (1985); Weiner, et al., *Cancer Res.*, 50:421 (1990)). Amplification and/or overexpression of the erbB-2 protooncogene has been found to correlate with poor prognosis in breast, ovarian and non-small cell lung carcinomas (Slamon, et al., *Science*, 235:177 (1986); Slamon, et al., *Science*, 244:707 (1989); Guerin, et al., *Oncogene Research*, 3:21 (1988); Wright, et al., *Cancer Res.*, 49:2087 (1989); Kern, et al., *Cancer Res.*, 50:5184 (1990); DiFiore, et al., *Science*, 237:178 (1987)). In addition to these clinical studies, in vitro studies strongly suggest that overexpression of the erbB-2 transmembrane receptor ($p185^{erbB-2}$) may have an important role in tumor progression (DiFiore, et al., *Science*, 237:178 (1987); Hudziak, et al., *Proc. Natl. Acad. Sci. USA*, 84:7159 (1987)).

An autocrine growth stimulatory pathway analogous with that proposed for epidermal growth factor receptor and its ligands may also be employed by a growing list of oncogene encoded transmembrane proteins that have structure reminiscent of growth factor receptors. This list includes the protooncogenes neu and its human equivalent erbB-2 or HER2 (Bargmann, et al., *Nature*, 319:226–229 (1986); Coussens, et al., *Science*, 230:1131–1139 (1985); Yamamoto, et al., *Nature*, 319:230–234 (1986); c-kit (Yarden, et al., *EMBO*, 6:341–3351 (1987); ros (Neckameyer, et al., *Mol. Cell. Biol.* 6:1478–1486 (1986); met (Park, et al., *PNAS*, 84:6379–6383 (1987); trk (Martin-Zanca, et al., *Nature*, 319:743–748 (1986); and ret (Takahashi, et al., *Mol. Cell. Biol.*, 7:1378–1385 (1987)). The erbB-2 and c-kit protooncogenes encode factors that display remarkable structural homology with EGFR (Yarden, et al., *Annu. Rev. Biochem.*, 57:443–478 (1988). Although erbB-2 and its related oncogene neu are related to EGFR, these proteins are distinct. For example, known EGFR ligands such as EGF and TGFα do not bind to erbB-2 receptor. (King, et al., *EMBO*, 7:1647 (1988); and Stern, et al., *EMBO*, 7:995 (1988).

If, according to the autocrine growth stimulatory pathway, malignant cells are capable of secreting a potent tumor growth factor in vivo, it is plausible that the growth factor ligand might be detected in body fluids, much like human chorionic gonadotropin or α-fetoprotein, and could be used as a tumor marker and a prognostic variable. Studies suggest that TGFα activity can be detected in body fluids of cancer patients and that its presence may provide important information concerning the biology of a patient's tumor (Stromberg, et al., *J. Cell. Biochem.*, 32:247–259 (1986); Twardzick, et al., *J. Natl. Cancer Inst.*, 69:793–798 (1982); Sherwin, et al., *Cancer Res.*, 43:403–407 (1983)).

Prior to the present invention, no ligand was known which binds to p185$^{erbB-2}$ protein. Thus, a need continues to exist for a ligand for p185$^{erbB-2}$. Such a ligand might be used to counteract the effects of c-erbB-2 oncogene overexpression in facilitating carcinogenesis.

SUMMARY OF INVENTION

Accordingly, it is an object of the present invention to provide a growth factor which interacts directly with the erbB-2 oncogene.

It is also an object of the present invention to provide a method for the isolation and purification of the above-described growth factor.

It is also an object of the present invention to provide a method for stimulating and/or inhibiting the growth of cells which overexpress the human oncogene erbB-2.

It is also an object of the present invention to provide a method for generally controlling the growth of over-expressing erbB-2 malignant mammalian cells, and, in particular, stimulating the growth of malignant cells at low (physiological) doses.

Accordingly, the above objects and others are provided by an approximately 30 kDa TGFα-like glycoprotein.

Having obtained the present 30 kDa glycoprotein, in accordance with another aspect of the present invention, the same is used to inhibit the growth of cells which overexpress the c-erbB-2 oncogene.

In accordance with the present invention, the present 30 kDa glycoprotein may be used, by itself, or in conjunction with other medicinal substances (e.g., toxic moieties or therapeutic agents) to inhibit the growth of any cells which overexpress the c-erbB-2 oncogene.

Generally, the present 30 kDa glycoprotein may be used advantageously to inhibit the growth of adenocarcinoma cells, preferably those of breast, ovarian, gastric and lung tissue which overexpress the erbB-2 oncogene.

In another aspect, the present invention relates to the preparation of monoclonal antibodies of gp30, and the use of these monoclonal antibodies to detect the presence of gp30 in patient sera or urine as a prognostic/diagnostic marker for tumor progression.

The present invention thus relates to the use of the present 30 kDa TGFα-like glycoprotein in direct interactions with EGFR and p185$^{erbB-2}$. Hence, in another aspect, the present invention provides conjugates of the 30 kDa glycoprotein ligand with either EGFR or p185$^{erbB-2}$. In still another aspect, the present invention provides diagnostic and therapeutic methods using these conjugates. Further, the present invention provides a diagnostic test kit using the present conjugates.

The present invention relates to an approximately 75 kilodalton growth factor ligand or functional derivative thereof which bind specifically to an erbB-2 oncogene product (p185$^{erbB-2}$) but fail to recognize and bind to an homologous transmembrane protein, i.e., epidermal growth factor receptor. Methods of obtaining the purified ligands of the present invention are also included in the present invention.

The invention additionally pertains to anti-ligand molecules such as antibodies or fragments of antibodies and blocking peptides which bind to the erbB-2 ligand of the present invention. A method to detect the presence of cells which express the erbB-2 ligand with these anti-ligand molecules is also disclosed. A further aspect of the invention involves the use of the erbB-2 ligand to detect cells expressing the erbB-2 oncogene product, p185$^{erbB-2}$.

The invention further pertains to a recombinant DNA molecule coding for a gene which is capable of expressing the erbB-2 ligand of the present invention and to host cells which contain such a recombinant DNA molecule.

The invention is also directed to a method for treating a number of cancers associated with the erbB-2 oncogene product overexpression including breast, ovarian, gastric, lung, prostate, salivary gland and thyroid carcinomas.

Lupu, et al., *Science*, 249:1552–1555 (1990) identified an approximately 30 kilodalton (kDa) glycoprotein (gp30) which is similar to TGFα in its ability to bind to the EGFR, phosphorylate EGFR, and induce colony formation. Direct binding of the gp30 to p185$^{erbB-2}$ was confirmed by binding competition experiments, suggesting that gp30 is a ligand for p185$^{erbB-2}$. Thus, Lupu, et al., identified and characterized a 30 kDa ligand that binds to erbB-2 receptor with high affinity and to EGFR with lower affinity.

Prior to the present invention, no ligand was known which binds to the erbB-2 oncogene product (p185$^{erbB-2}$) but falls to react with EGFR. Such a ligand will be important for understanding the function of p185$^{erbB-2}$ and may be a potential therapeutic and diagnostic target for neoplasia.

Ligands for erbB-2 are of extreme interest. They may directly modulate the growth of cancer cells expressing this receptor. They may be conjugated or otherwise coupled to a variety of toxins, drugs and isotopes, for example, to target these therapies to cancer for increased therapeutic efficacy or for imaging purposes. In addition, brief stimulation of a cancer by the ligand may be combined with subsequent chemotherapy to increase the responsivity of the cancer.

BRIEF DESCRIPTION OF THE DRAWINGS

FIGS. 17A–B show separation of tryptic digested gp30 by C18-Reversed Phase chromatography and amino acid composition of derived peptides. FIG. 17A shows tryptic digestion/C18 chromatography; FIG. 17B shows the sequences obtained from isolated marked peaks. The sequences for peak number 1, 2, 3, 4, and 5 are shown in SEQ ID NO: 1, 2, 3, 4, and 5.

FIGS. 18A–D show the full cDNA sequence of gp30/α1 and β1, and a demonstration of four different gp30 isoforms in breast cancer cells by RNase protection assay. FIG. 18A shows the full cDNA sequence of gp30/α1 (SEQ ID NO: 6). FIG. 18B shows the full cDNA sequence of gp30/β1 (SEQ ID NO: 7). FIG. 18C shows the fragments of four different gp30 isoforms expected to be protected in the RNAse protecting assay. When using the β1 probe in the RNAse protecting assay, the sequences expected to be protected in α1 are GAATGTGCCCATGAAAGTCCAAAACCA (SEQ ID NO: 8), and AGAAAAGGCGGAGGAGCT (SEQ ID NO: 9); the sequence expected to be protected in β1 is shown in SEQ ID NO: 10 and the sequences expected to be protected in β2 and β3 are portions of the sequence shown in SEQ ID NO: 10.

FIGS. 23A–C show generation of a specific erbB-2 ligand PCR product from breast cancer specimens. FIG. 23A shows the sequences of degenerate primers. The RNA sequence derived from Lys-Gly-Lys-Gly-Lys-Lys-Xaa (a portion of SEQ ID NO: 1) is shown in SEQ ID NO: 11 and the probe sequence complementary to the RNA sequence is shown in SEQ ID NO: 13. The RNA sequence derived from Gly-Glu-Tyr-Met-Cys-Lys-Val (SEQ ID NO: 15) is shown in SEQ ID NO: 14 and the probe sequence complementary to the RNA sequence: is shown in SEQ ID NO: 16. FIG. 23B shows the DNA sequence (SEQ ID NO: 17) and the peptide sequence (SEQ ID NO: 18) obtained from the 500 bp PCR product.

DESCRIPTION OF THE PREFERRED EMBODIMENTS

Figure 1:
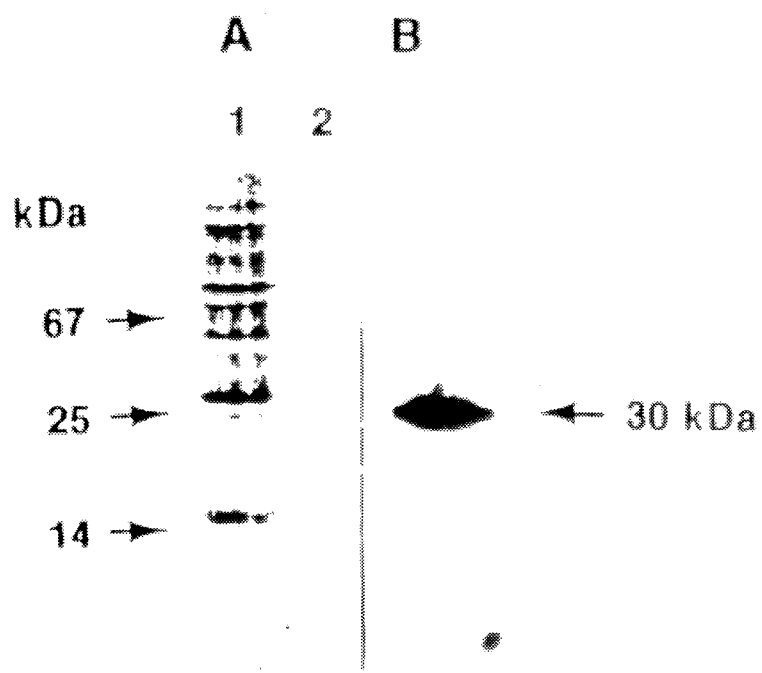
FIG. 1 illustrates the isolation of the present 30 kDa growth factor. Portion A illustrates the use of low affinity heparin chromatography, while portion B illustrates the use of reversed-phase chromatography.

The present invention is predicated upon the discovery that hormone dependent or independent breast cancer cells secrete growth factors, including an insulin-like growth factor I activity, insulin-like growth factor II, transforming growth factor alpha platelet-derived growth factor, members of the FGF family and erbB-2 ligands. Secretion of some of these factors is stimulated by estradiol, and antiestrogens act by decreasing the secretion of these growth factors in hormone dependent breast cancers but not in other tumors.

In fact, a variety of strategies which either block the secretion of these growth factors in vitro can interfere with the growth of human breast cancer cells. Such strategies may include the use of anti-growth factor antibodies, anti-growth factor receptor antibodies, synthetic peptides, drugs which interfere with the ligand-receptor interaction, inhibitory ligands, stable transfection of breast cancer cells with antisense genes or specific growth factor receptors or short term treatment with antisense oligonucleotides to growth factor receptors.

Generally, the present invention provides ligands for p185$^{erbB-2}$, which are capable of generally controlling the growth of erbB-2 overexpressing (o/e) cells when applied thereto, and, in particular, either inhibiting or stimulating the growth of o/e erbB-2 cells when applied thereto.

In the description that follows, a number of terms used in the field of ligand-growth factor receptor interactions and recombinant DNA technology are extensively utilized. In order to provide a clearer and consistent understanding of the specification and claims, including the scope to be given such terms, the following definitions are provided.

Mutant. As used herein, the term "mutant" is meant to include derivatives of an erbB-2 ligand in which the amino acid sequence of the protein has been modified in a manner resulting from addition, substitution, insertion or deletion of one or more amino acids in or from the wild type protein. By a "biologically active mutant" of a erbB-2 ligand is meant a mutant of the ligand which retains all or some of the biological activity possessed by the ligand, particularly the receptor binding activity, and most particularly the stimulation of p185$^{erbB-2}$ autophosphorylation. Mutation may also be used as a general term to denote the modification of any DNA or RNA sequence by addition, substitution, insertion or deletion of one or more nucleotides within that sequence.

Functional Derivative. By a "functional derivative" of the erbB-2 ligand of the invention is meant a ligand that possesses a biological activity which is substantially similar to the ligand from which the derivative is derived. By "substantially similar" is meant a biological activity which is qualitatively similar but quantitatively different from an activity possessed by a normal erbB-2 ligand. By the phrase "a biological activity which is qualitatively similar" is meant a ligand which more or less retains the biological activity of the natural erbB-2 ligand. For example, a functional derivative of the erbB-2 ligand retains the $p185^{erbB-2}$ receptor binding activity, and preferably retains the ability to stimulate autophosphorylation of $p185^{erbB-2}$. The term "functional derivative" is intended to include biologically active "mutants," "fragments," and "variants," of the erbB-2 ligand.

Fragment. A "fragment" of the erbB-2 ligand is meant to refer to a protein molecule which contains a portion of the complete amino acid sequence of the wild type ligand. By a "biologically active fragment" of a ligand is meant a fragment of the erbB-2 ligand which retains all or some of the biological activity possessed by the ligand. For example, if the fragment retains some or all of the receptor binding activity, then such fragment is said to be a biologically active fragment of erbB-2 ligand.

Variant. A "variant" of the erbB-2 ligand is meant to refer to a ligand substantially similar in structure and biological activity to either the native erbB-2 ligand or to a fragment thereof, but not identical to such molecule or fragment thereof. A variant is not necessarily derived from the native molecule and may be obtained from any of a variety of similar or different cell lines. The term "variant" is also intended to include genetic alleles. Thus, provided that two erbB-2 ligands possess a similar structure and biological activity, they are considered variants as that term is used herein even if the composition or secondary, tertiary, or quaternary structure of one of the ligands is not identical to that found in the other.

Generally, erbB-2 ligand variants will have amino acid sequences that correspond to each other. One amino acid sequence "corresponds" to another amino acid sequence if at least 75% of the amino acid positions in the first sequence are occupied by the same amino acid residues in the second sequence. Preferably 90% of the amino acid positions are identical, and most preferably 95% of the amino acid positions are identical. Alternatively, two amino acid sequences are considered to correspond to each other if the differences between the two sequences involve only conservative substitutions.

"Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge as the amino acid for which it is substituted and the substitution has no significant effect on the local conformation of the protein. Amino acid pairs which may be conservatively substituted for one another are well-known to those of ordinary skill in the art.

As used herein, the term "variant" is meant to include polypeptides or nucleic acids encoding polypeptides that are substantially homologous. Two amino acid sequences are "substantially homologous" when at least about 90% of the amino acids match over the defined length of the amino acid sequences, preferably a match of at least about 92%, more preferably a match of at least about 95%. Preferred variants of erbB-2 ligands contain amino acid sequences that differ from the sequence of other erbB-2 ligands by 25 or fewer amino acid residues, more preferably, 18 or fewer residues, even more preferably about 12 or fewer residues and most preferably about 10 or fewer residues.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See e.g., Maniatis et al., supra; DNA Cloning, vols. 1 and II supra; Nucleic Acid Hybridization, supra. DNA sequences encoding erbB-2 ligands are substantially homologous if they hybridize under stringent hybridization conditions as defined in International Patent Publication WO 92/20798 (incorporated herein by reference).

One DNA sequence "corresponds" to another DNA sequence if the two sequences encode the same amino acid sequence.

erbB-2 ligand. The term "erbB-2 ligand" is meant to refer to a protein molecule which is capable of specifically binding to an erbB-2 oncogene product ($p185^{erbB-2}$). Preferred erbB-2 ligands have one or more of the biological activities of the polypeptides encoded by the DNA sequences in FIGS. 18A and B. In particular, preferred erbB-2 ligands are capable of activating $p185^{erbB-2}$; most particularly, preferred erbB-2 ligands stimulate autophosphorylation of $p185^{erbB-2}$. Most preferred erbB-2 ligands are those that fail to bind to the epidermal growth factor receptor. As used herein, the term "erbB-2 ligand" is meant to include any functional derivative of the erbB-2 ligand of the present invention. The erbB-2 ligands of the present invention may bind other protooncogene encoded transmembrane proteins such as c-kit, neu, ros, etc., and thus the term "erbB-2 ligand" is not limited to protein molecules which only bind the erbB-2 oncogene product. Binding of the erbB-2 ligand molecules of the present invention may induce cellular responses of cells which express such other protooncogenes and thus may be used to treat and diagnose patients that have malignant cells which express these other protooncogenes.

A composition comprising a selected polypeptide component is "substantially pure" when the polypeptide component makes up at least about 75% by weight of the combined weight of polypeptide components in the composition. Preferably, the selected component comprises at least about 90% by weight of the combined weight, most preferably at least about 99% by weight of the combined weight. In the case of a composition comprising a selected biologically active protein, which is substantially free of contaminating proteins, it is sometimes preferred that the composition having the activity of the protein of interest contain species with only a single molecular weight (i.e., a "homogeneous" composition).

A. Ligands of the erbB-2 Transmembrane Protein

The human c-erbB-2 oncogene encodes a 185 kDa transmembrane glycoprotein having protein kinase activity. This glycoprotein, known as $p185^{erbB-2}$, shows extensive structural similarity with the p170 epidermal growth factor receptor (EGFR) and is therefore thought to be growth factor receptor. However, neither EGF nor TGFα, the normal ligands for the EGFR, interact directly with p185$^{erbB-2}$. In fact, no ligand for this glycoprotein has been described prior to this invention. It would be extremely desirable to find a ligand for this 185 kDa glycoprotein, inasmuch as erbB-2 oncogene is amplified in many adenocarcinomas and is over expressed in nearly 30% of human breast cancer patients. Additionally, it is known that p185$^{erbB-2}$ is necessary for the maintenance of the malignant phenotype of cells transformed by the oncogene.

In accordance with the present invention, it has been surprisingly discovered that a number of structurally distinct polypeptides function as ligands for p185$^{erbB-2}$. These ligands include polypeptides of about 20–26 kDa (which are glycosylated to form ligands of 30–45 kDa apparent molecular weight) and also include polypeptides of about 75 kDa which are not glycosylated. These ligands share the properties of specifically binding to p185$^{erbB-2}$ and inducing autophosphorylation thereof. The ligands differ in structure and some other biological activities. All of the polypeptides which specifically induce autophosphorylation of p185$^{erbB-2}$ are termed "erbB-2 ligands" herein. The low molecular weight glycosylated species of erbB-2 ligands are variously described herein by the terms "heregulin", "gp30", "30 kDa growth factor", "30 kDa ligand", or "TGFα-like polypeptide". The higher molecular weight species is additionally identified as "p75".

An approximately 30 kDa growth factor (gp30) which is secreted from the estrogen receptor negative cell line MDA-MB-231 is effective as a ligand for p185$^{erbB-2}$ glycoprotein. The 30 kDa glycoprotein of the present invention also exhibits some TGFα-like activity. For example, the present 30 kDa glycoprotein binds to EGFR, is capable of phosphorylating EGFR as well as inducing NRK colony formation, although with a lower affinity than either EGF or TGFα. This is quite surprising inasmuch as the present 30 kDa growth factor is distinct from the normal 16–18 kDa precursor for TGFα or mature TGFα as shown by peptide mapping of the translated proteins. The 30 kDa glycoprotein was observed, unlike EGF and TGFα, to bind to heparin-sepharose, and can be purified to apparent homogeneity by heparin affinity chromatography and subsequent reversed phase chromatography. The heparin binding ability of gp30 is a novel and surprising finding for a growth factor from the EGF family.

The gp30 glycoprotein binds to epidermal growth factor receptor (EGFR) and has TGFα-related properties. In addition, purified gp30 stimulates phosphorylation of p185$^{erbB-2}$ in cells that overexpress erbB-2, in contrast with TGFα and EGF which do not interact with p185$^{erbB-2}$. Surprisingly, gp30 inhibits cell growth in all cells that overexpressed erbB-2 (Lupu, et al., *Science*, 249:1552 (1990)). A monoclonal antibody (4D5) against the extracellular domain of p185$^{erbB-2}$ (Hudziak, et al., *Molec. Cell. Biol.*, 9:1165 (1989)) was able to compete with gp30 for binding to p185$^{erbB-2}$, indicating that the gp30 ligand recognizes and binds to the 4D5 binding site.

However, in accordance with another aspect of the present invention, it has been surprisingly discovered that very low concentrations of gp30 have a stimulatory effect on cells as evidenced by both standard mitogenesis assays and clonogenic assays. By contrast, at higher concentrations, the ligand is growth inhibitory in both assays.

In accordance with the present invention, it has been found that gp30 competes for binding with antibodies directed against erbB-2 which inhibit growth. Further, it has also been found that the gp30 ligand at low concentrations is capable of reversing antibody-induced growth inhibition. Additionally, the gp30 ligand can overcome inhibitory effects seen in cells which overexpress erbB-2 protein which are induced by extracellular domain fragments of the erbB-2 receptor, which indicates a specific pathway of action for the gp30 ligands mediated for interaction with erbB-2.

Due to the ability of the gp30 ligand to compete with monoclonal antibodies for binding the erbB-2, the present invention also provides a radioreceptor assay in which erbB-2 ligands can be identified by their ability to displace radiolabeled antibodies from binding to erbB-2. The present invention thus provides an affinity chromatography purification technique using soluble erbB-2 extracellular domain.

Generally, the 30 kDa glycoprotein can be immunoprecipitated by an anti-TGFα polyclonal antibody and exhibits some TGFα-like biological activity when assayed by EGF radioreceptor assay and NRK and AlN4T cell colony formation assays. The 30 kDa growth factor also stimulates autophosphorylation of the EGF receptor, although less efficiently than mature 6 kDa TFGα or EGF.

Tunicamycin treatment in vivo or N-glycanase deglycosylation in vitro revealed a precursor of 22 kDa in contrast to the 16–18 kDa precursor for mature TGFα. Furthermore, in vitro translation of total mRNA from MDA-MB-231 cells confirmed these observations. Biochemical characterization of the 30 kDa TGFα-like protein was obtained by V8-protease digestion of the de-glycosylated polypeptides and translated products. Peptide mapping of the V8-digested, immunoprecipitated material suggests an amino acid sequence distinct from TGFα. Hence, the 30 kDa polypeptide, while related to the EGF/TGFα family, is encoded by a different gene and is not a post-translation modification of mature TGFα.

The 30 Kd glycoprotein of the present invention is well-characterized by:
1) being a heparin binding growth factor;
2) being capable of strongly binding to erbB-2;
3) being capable of induce tyrosine phosphorylation of p185erbB-2;
4) being capable of inducing internalization of the erbB-2 receptor;
5) being capable of stimulate growth of overexpressing erbB-2 cells at low concentrations;
6) being capable of inhibiting growth of erbB-2 overexpressing cells at high concentrations;
7) being capable of competing with specific erbB-2 monoclonal antibodies, which antibodies are capable of inducing growth inhibition of erbB-2 overexpressing cells; and
8) being capable of inducing differentiation of overexpressing erbB-2 cells at high concentrations;

In accordance with the present invention, as described above, it has also has been discovered that gp30, as well as EGF and TGFα induce cell proliferation of cells such as NRK cells and immortalized human breast epithelial AlN4 cells. Hence, all three ligands have stimulatory activity on cells containing high amounts of EGFR, because of their ability to interact with EGFR.

Accordingly, the 30 kDa glycoprotein of the present invention may be further characterized by:
1) being capable of weakly binding to EGF receptor;
2) exhibiting cross-reactivity to antibodies to TGFα;
3) being capable of cleavage by elastase; and 4) being capable of stimulating transforming activity in normal rat kidney (NRK) cells.

The erbB-2 ligands of the present invention also includes a 75 kilodalton protein (p75), although the invention is intended to include any functional derivatives of this factor. Substantially purified p75 ligand competes for p185$^{erbB-2}$ binding with monoclonal antibodies that bind to p185$^{erbB-2}$ so that proliferation of erbB-2 overexpressing cells is inhibited, such as monoclonal antibody 4D5 (Hudziak, et al., *Mol. Cell. Biol.*, 9:1165 (1989)), and p75 induces phosphorylation of p185$^{erbB-2}$. In cell growth assays, cell proliferation and colony formation of cell lines overexpressing erbB-2 were inhibited with high concentration of p75. Furthermore, p75 can reverse the antiproliferative effect of soluble erbB-2 extracellular domain (ECD).

The 75 kDa erbB-2 ligand of the present invention is extremely important because of the specificity for p185$^{erbB-2}$. Surprisingly, this erbB-2 ligand does not recognize or bind to EGFR, a highly homologous receptor to p185$^{erbB-2}$. This characteristic allows the design of diagnostic and therapeutic agents specifically directed against carcinoma cells which overexpress erbB-2.

B. Identification of erbB-2 Ligands

Identification of erbB-2 ligands of the present invention can be accomplished by using a radioreceptor assay to screen conditioned media from a number of cells. Any cell type may be used in a screen to isolate ligand-producing cells. Preferably, erbB-2 overexpressing cells are used.

The radioreceptor assay, according to the present invention, utilizes a labeled antibody which binds to the extracellular domain of p185$^{erbB-2}$. Antibodies directed against the erbB-2 receptor extracellular domain are well known. The preferred antibodies for identifying erbB-2 ligands of the present invention are 4D5 (Hudziak, et al., *Mol. Cell. Biol.*, 9:1165 (1989)), which may be obtained from Genentech, Calif.

The antibody 4D5 binds to the same binding site of the extracellular domain of p 185$^{erbB-2}$ such that the erbB-2 ligand of the present invention is inhibited from binding the receptor in the presence of these antibodies. Thus, these antibodies can be used in competitive binding assays to identify cell lines that produce the erbB-2 ligand of the invention. One of skill in the art will appreciate that other antibodies which recognize different binding sites or epitopes on the extracellular domain can be generated by well known techniques to identify a number of ligands not previously described. Thus, use of different antibodies which bind distinct locations on the extracellular domain of p185$^{erbB-2}$ may provide for the isolation of unique ligands.

In the assay of the present invention, conditioned media is prepared according to commonly employed procedures. For instance, media from a cell culture is cleared from cells and concentrated 100 fold in an Amicon ultrafiltration unit (Yarden, et al., *Proc. Natl. Acad. Sci.*, 86:3179–3183 (1989); Lupu, et al., *Biochemistry*, 31:7330–7340 (1992); and Bates, et al., *Cancer Res.* 46:1707–1713 (1986).

Competitive binding of the labeled antibody to p185$^{erbB-2}$ in the presence of conditioned media provides a method for detecting cells which produce ligands. In this manner, the ligand in the conditioned media will compete with the labeled antibody for binding to the p185$^{erbB-2}$ protein. Monitoring the amount of label bound to erbB-2 protein is determinative of the presence of ligand. For example, decrease in label attached to the erbB-2 receptor indicates the presence of ligand.

In order to determine whether gp30 bonded specifically to p185$^{erbB-2}$, p185$^{erbB-2}$ binding competition assays were performed. Since iodinated gp30 was not available, an iodinated anti-erbB-2 (4D5) that induced similar biological responses to gp30 in cells with erbB-2 overexpression was used. Iodinated 4D5 MAb was used for the receptor binding experiments, in the presence of increasing concentrations of gp30. The gp30 displaced 4D5 binding to p185$^{erbB-2}$ in intact SK-Br-3 and MDA-MB-453 cells clearly indicating that gp30 binds to the receptor. In a control experiment, the binding to erbB-2 of an iodinated antibody that does not show anti-proliferative effects was not altered by gp30. The gp30 binding activity was not inhibited by excess concentrations of EGF or TGFα.

In order to verify that the receptor competition was specific, iodinated 4D5 was covalently cross-linked to p185$^{erbB-2}$ in the presence or absence of gp30. The complex was immunoprecipitated with an antibody to the COOH-terminal domain of p185$^{erbB-2}$ and analyzed by SDS-polyacrylamide gel electrophoresis (PAGE). The autoradiogram showed a specific high molecular weight 4D5 binding site. Cross-linking of p185$^{erbB-2}$ and iodinated 4D5 was blocked in the presence of gp30. Blocking was not observed in the presence of EGF.

Clearly, gp30 secreted by the MDA-MB-231 breast cancer cell line is a ligand for p185$^{erbB-2}$. Moreover, gp30 also is capable of stimulating p185$^{erbB-2}$ and EGFR phosphorylation. Hence, gp30 can interact directly and independently with p185$^{erbB-2}$ and EGFR, and is considered to exhibit auto-stimulatory properties.

The erbB-2 ligands of this invention can be identified or detected by other procedures, including competitive binding studies with EGF (for gp30 species), direct binding to p185$^{erbB-2}$ or its ECD, autophosphorylation assays with p185$^{erbB-2}$ cells, or binding of antibodies to erbB-2 ligands. These procedures are described in detail below, especially in Examples 3, 8–12 and 14–19.

C. Purification of erbB-2 Ligand

In accordance with this invention, erbB-2 ligand can be isolated from a cell producing the ligand. Any cell that produces the ligand may be used as a starting material according to the methods described in this invention. Lupu, et al., *Science*, 249:1552–1555 (1990) reported the identification and purification of a 30 kilodalton (kDa) growth factor secreted by MDA-MB-231 human breast cancer cells. This glycoprotein (gp30) was purified to apparent homogeneity by sequential low affinity heparin-sepharose chromatography and by reversed phase chromatography. Preferably, SK-Br-3 is used to isolate the 75 kDa erbB-2 ligand of the present invention. This strain is well known to those of skill in the art and is deposited with the American Type Culture Collection, Rockville, Md., 20852 USA (accession number ATCC HTB 30). However, any cell which is found to contain the erbB-2 ligand or functional derivatives thereof can be used to isolate and purify such a factor from the cell and/or its culture medium. The ligands of the present invention can, for example, be isolated from a host cell which expresses a recombinant ligand. The ligand of the present invention is likely to be excreted from the cell. Accordingly, the ligand will normally be purified from the culture media. However, cellular extracts may serve as a source from which to purify the ligand of the present invention. Typically, the cells producing the desired ligand are grown in media conducive to cell growth. The cells are removed and the desired ligand is purified from the media.

The ligands of the present invention can be extracted and purified from the culture media or cell by using known protein purification techniques commonly employed, such as extraction, precipitation, ion exchange chromatography, affinity chromatography, gel filtration and the like. The most preferred methods to isolate the erbB-2 ligand of the present invention are by affinity chromatography using the erbB-2 receptor extracellular domain bound to a column matrix or by heparin chromatography.

As will be apparent to those of skill in the art, extracellular domain obtained from a natural host producing the protein can be used to purify the ligand of the present invention. For example, SK-Br-3 cells have been used to purify the extracellular domain of $p185^{erbB-2}$ (Alper, et al., *Cell Growth and Differentiation* 1:591–599 (1990)). Alternatively, purified recombinant extracellular domain of $p185^{erbB-2}$ can be used in affinity chromatography to obtain the erbB-2 ligand of the present invention. It will be appreciated that the whole $p185^{erbB-2}$ receptor protein or portions of such a protein may be used to purify the erbB-2 ligand according to the present invention, provided that the protein bound to the column matrix contains the desired erbB-2 ligand binding site of the extracellular domain. Yamamoto, et al., *Nature*, 319:230–(1986) describes cloning and expression of the full length $p185^{erbB-2}$ gene. A plasmid containing the erbB-2 receptor gene can be obtained from the American Type Culture Collection, Rockville, Md. (Accession No. ATCC 57584).

Using an affinity chromatography purification procedure, erbB-2 ligand was substantially purified from the cellular media. As used herein, the term "substantially pure" or "substantially purified" is meant to describe a ligand which is substantially free of any compound normally associated with the protein in its natural state, i.e., substantially free of contaminating protein and carbohydrate components. The term is further meant to describe a ligand of the present invention which is homogeneous by one or more purity or homogeneity characteristics used by those of skill in the art. For example, substantially pure ligand proteins will show constant and reproducible characteristics within standard experimental deviations for parameters such as the following: molecular weight, chromatographic techniques, and such other parameters. The term, however, is not meant to exclude artificial or synthetic mixtures of the erbB-2 ligand with other compounds. The term is also not meant to exclude the presence of minor impurities which do not interfere with the biological activity of the enzyme, and which may be present, for example, due to incomplete purification.

D. Cloning erbB-2 Ligand Genes

Any of a variety of procedures may be used to clone the erbB-2 ligand genes of the present invention. One such method entails analyzing a shuttle vector library of DNA inserts (derived from a cell which expresses the erbB-2 ligand) for the presence of an insert which contains the ligand gene. Such an analysis may be conducted by transfecting cells with the vector and then assaying for expression of the ligand binding activity. The preferred method for cloning these genes entails determining the amino acid sequence of the erbB-2 ligand protein. Usually this task will be accomplished by purifying the desired ligand protein and analyzing it with automated sequencers. Alternatively, each protein may be fragmented as with cyanogen bromide, or with proteases such as papain, chymotrypsin or trypsin (Oike, Y., et al., *J. Biol. Chem.*, 257:9751–9758 (1982); Liu, C., et al., *Int. J. Pept. Protein Res.*, 21:209–215 (1983)). Although it is possible to determine the entire amino acid sequence of these proteins, it is preferable to determine the sequence of peptide fragments of these molecules.

Once one or more suitable peptide fragments have been sequenced, the DNA sequences capable of encoding them are examined and one or more suitable oligodeoxyribonucleotides which encode a fragment of the desired erbB-2 ligand sequence are identified. Because the genetic code is degenerate, more than one codon may be used to encode a particular amino acid (Watson, J. D., *In: Molecular Biology of the Gene*, 3rd Ed., W. A. Benjamin, Inc., Menlo Park, Calif. (1977), pp. 356–357). The oligonucleotides were synthesized at LCRC and at Biosynthesis, Tx. The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide. Alternatively, a suitable oligonucleotide that is capable of encoding a fragment of an erbB-2 ligand may be identified in the erbB-2 ligand sequence provided herein in FIG. 17B, or the oligonucleotide of FIGS. 18A and B or 23A and B may be used.

In a manner exactly analogous to that described above, one may employ an oligonucleotide (or set of oligonucleotides) which have a nucleotide sequence that is complementary to the oligonucleotide sequence or set of sequences that is capable of encoding the peptide fragment.

A suitable oligonucleotide, or set of oligonucleotides which is capable of encoding a fragment of the desired erbB-2 ligand gene (or which is complementary to such an oligonucleotide, or set of oligonucleotides) is identified (using the above-described procedure), synthesized, and hybridized, by means well known in the art, against a DNA or, a cDNA preparation depending upon the source of the gene. Typically, isolation of eukaryotic genes is done by screening a cDNA library, while a DNA library is used to isolate prokaryotic genes. Techniques of nucleic acid hybridization are disclosed by Maniatis, et al., *In: Molecular Cloning, a Laboratory Manual*, Second Edition, Coldspring Harbor, N.Y. (1989), and by Haymes, et al., *In: Nucleic Acid Hybrization, a Practical Approach*, IRL Press, Washington, D.C. (1985), which references are herein incorporated by reference. The source of DNA or cDNA used will preferably have been enriched for the desired sequences. Such enrichment can most easily be obtained from cDNA obtained by extracting RNA from cells cultured under conditions which induce erbB-2 ligand synthesis.

Techniques such as, or similar to, those described above have successfully enabled the cloning of genes for human transforming growth factor-alpha (Derynck, et al., *Cell* 38:287–298 (1984)), chicken epidermal growth factor receptor (Lax, et al., *Mol. Cell. Biol.*, 8:1970–1978 (1988)), human aldehyde dehydrogenases (Hsu, et al., *Proc, Natl. Acad. Sci. USA*, 82:3771–3775 (1985)), fibronectin (Suzuki, et al., *Eur. Mol. Biol. Organ. J.*, 4:2519–2524 (1985)), the human estrogen receptor gene (Walter, et al., *Proc. Natl. Acad. Sci. USA*, 82:7889–7893 (1985)), tissue-type plasminogen activator (Pennica, et al., *Nature*, 301:214–221

(1983)) and human term placental alkaline phosphatase complementary DNA (Kam, et al., *Proc. Natl. Acad. Sci. USA*, 82:8715–8719 (1985)).

In a alternative way of cloning the erbB-2 ligand genes of the present invention, a library of expression vectors is prepared by cloning DNA or cDNA, from a cell capable of expressing such a ligand into an expression vector. The library is then screened for members capable of expressing a protein which binds to an anti-ligand molecule (antibody or blocking peptide) and which has a nucleotide sequence that is capable of encoding polypeptides that have the same amino acid sequence as the erbB-2 ligand protein of the present invention, or fragments or variants thereof.

Alternatively, DNA sequences encoding erbB-2 ligands may be amplified by the polymerase chain reaction (PCR) using primers that correspond to appropriate sequences, such as those shown in FIG. 23A. Amplified sequences may be introduced into a vector and thereafter cloned as described below.

E. Expression of erbB-2 Ligand Genes

DNA molecules comprising an erbB-2 ligand gene or at least portions of this gene can be operably linked into an expression vector and introduced into a host cell to enable the expression of the ligand by that cell. Two DNA sequences (such as a promoter region sequence and a desired ligand protein encoding sequence) are said to be operably linked if the nature of the linkage between the two DNA sequences does not (1) result in the introduction of a frame-shift mutation, (2) interfere with the ability of the promoter region sequence to direct the transcription of the desired protein encoding gene sequence, or (3) interfere with the ability of the desired protein gene sequence to be transcribed by the promoter region sequence.

A DNA sequence encoding an erbB-2 ligand protein may be recombined with vector DNA in accordance with conventional techniques. The present invention encompasses the expression of the desired fusion proteins in either prokaryotic or eukaryotic cells. Eukaryotic hosts include yeast (especially Saccharomyces), fungi (especially Aspergillus), mammalian cells (such as, for example, human or primate cells) either in vivo, or in tissue culture.

Yeast and mammalian cells provide substantial advantages in that they can also carry out post-translational peptide modifications including glycosylation. A number of recombinant DNA strategies exist which utilize strong promoter sequences and high copy number plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired fusion protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired fusion protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, et al., *J. Mol. Appl. Gen.*, 1:273–288 (1982)); the TK promoter of Herpes virus (McKnight, *Cell*, 31:355–365 (1982)); the SV40 early promoter (Benoist, et al., *Nature* (London), 290:304–310 (1981)); the yeast gal4 gene promoter (Johnston, et al., *Proc. Natl. Acad. Sci. (USA)*, 79:6971–6975 (1982); Silver, et al., *Proc. Natl. Acad. Sci. (USA)*, 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired fusion protein does not contain any intervening codons which are capable of encoding a methionine (i.e., AUG). The presence of such codons results either in the formation of a fusion protein (if the AUG codon is in the same reading frame as the desired fusion protein encoding DNA sequence) or a frame-shift mutation (if the AUG codon is not in the same reading frame as the desired fusion protein encoding sequence).

The expression of the erbB-2 ligand protein can also be accomplished in procaryotic cells. Preferred prokaryotic hosts include bacteria such as *E. Coli*, Bacillus, Streptomyces, Pseudomonas, Salmonella, Serratia, etc. Bacterial hosts of particular interest include *E. Coli* K12, and other enterobacteria (such as *Salmonella typhimurium* or *Serratia marcescens*), and various Pseudomonas species. The prokaryotic host must be compatible with the replicon and control sequences in the expression plasmid.

To express the desired ligand protein in a prokaryotic cell (such as, for example, *E. coli*, *B. subtilis*, Pseudomonas, Streptomyces, etc.), it is necessary to operably link the desired ligand protein encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the b-lactamase gene of pBR322, etc. Examples of inducible prokaryotic promoters include the major right and left promoters of bacteriophage λ ($P_L$ and $P_R$) the trp, recA, lacZ, lacI, gal, and tac promoters of *E. coli*, the a-amylase (Ulmanen, I., et al., *J. Bacteriol.* 162:176–182 (1985)), the s-28 specific promoters of *B. subilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, et al., *Mol. Gen. Genet.*, 203:468–478 (1986)). Prokaryotic promoters are reviewed by Glick, B. R., *J. Ind. Microbiol.*, 1:277–282 (1987); Cenatiempo, Y., *Biochimie*, 68:505–516 (1986); and Gottesman, S., *Ann. Rev. Genet.*, 18:415–442 (1984).

Proper expression in a prokaryotic cell also requires the presence of a ribosome binding site upstream from the gene-encoding sequence. Such ribosome binding sites are disclosed, for example, by Gold, et al., *Ann. Rev. Microbial.*, 35:365–404 (1981).

The desired protein encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired ligand molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, et al., *Miami Wntr. Symp.*, 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., pp. 44–470 (1981); Broach, J. R., *Cell*, 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.*, 3:280 (1983), and others.

Preferred prokaryotic vectors include plasmids such as those capable of replication in *E. coli* such as, for example, pBR322, ColE1, pSC101, paCYC 184, πVX. Such plasmids are, for example, disclosed by Maniatis, et al., (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, New York (1982), pp. 307–329). Suitable Streptomyces plasmids include pU101 (Kendall, et al., *J. Bacteriol.*, 169:4177–4183 (1987)), and Streptomyces bacteriophages such as φC31 (Chater, et al., In: *Sixth International Symposium on Actinomycetales Biology*, Akademiai Kaido, Budapest, Hungary (1986), pp. 45–54). Pseudomonas plasmids are reviewed by John, et al., (*Rev. Infect. Dis.*, 8:693–704 (1986)), and Izaki, K. (*Jpn. J. Bacteriol.*, 33:729–742 (1978)).

Once the vector or DNA sequence containing the construct has been prepared for expression, the DNA construct may be introduced (transformed) into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the recombinant erbB-2 ligand protein of the present invention.

F. Purification of Recombinant erbB-2 Ligand

The erbB-2 ligand proteins of this invention can be produced by fermentation of the recombinant host containing the cloned ligand genes. The recombinant host, such as mammalian cells producing the cloned protein, can be grown and harvested according to techniques well known in the art.

The recombinant erbB-2 ligand proteins of the present invention can be extracted and purified from the recombinant host or its culture media by using known protein purification techniques commonly employed, such as extraction, precipitation, ion exchange chromatography, affinity chromatography, gel filtration and the like. Biochemical techniques employed to isolate the erbB-2 ligand proteins of the present invention from SK-Br-3 are of particular interest when purifying these proteins from a recombinant host.

G. Anti-Ligand Molecules

The present invention concerns anti-ligand molecules which bind covalently or non-covalently to the erbB-2 ligands of the present invention. Without being limited, the anti-ligand molecules of the present invention include antibodies, blocking peptides and any other molecule, compound, chemical, etc. that is capable of covalently or non-covalently binding to the erbB-2 ligand of the present invention.

Blocking peptides, according to the present invention, are "capable of binding" a molecule if they are capable of specifically reacting with or have affinity for the molecule such that the blocking peptide will bind to the molecule. An example of a blocking peptide of the present invention is the extracellular domain of the erbB-2 transmembrane receptor. Typically, peptide fragments of the extracellular domain which bind to the erbB-2 ligand of the present invention may be used, although functional derivatives of such erbB-2 transmembrane receptor may be used. Such derivatives may include, for example, neu, c-kit, met or any transmembrane tyrosine kinases that have a structure reminiscent of growth factor receptors.

The blocking peptides of the present invention may be prepared by a number of well known techniques. Synthetic peptides may be constructed using automated protein synthesizers. Alternatively, the blocking peptides of the invention may be generated through recombinant DNA techniques. For instance, a DNA molecule encoding for the desired peptide may be operably linked to a promoter and other regulatory sequences such that expression of said peptide can be obtained in a transformed host. A number of methods of producing a desired blocking peptide will be readily apparent to one of skill in the art.

It will be understood by those of skill in the art that the blocking peptide of the present invention can be detectably labeled or conjugated with therapeutic agents by standard techniques well known in the art. Examples of detectable labels are described below which may be used to detectably label the blocking peptides of the present invention.

The term "therapeutic agent" as used herein is meant to refer to any molecule, chemical compound, protein etc. which, when introduced in close association to a cell, is capable of killing, destroying, inhibiting the growth or reproduction of, or otherwise interfering in the normal physiology or metabolism of said cell in a manner not conducive to the cell's survival or reproduction. Examples of suitable therapeutic agents include cytotoxic drugs, toxins, isotopes, endocrine therapies and the like. Specific cytotoxic drugs that may be used are Adriamycyn, Cyclophosphamide, 5-Fluorouracil, Methotrexate, Cisplatin, Carboplatin, Vincristine, VP-16, Bleomycin, Mitomycin C, Taxol, etc. Toxins may include Ricin A, Diphtheria, and Pseudomonas. Examples of suitable isotopes include $p^{32}$, Indium, Yttrium, and Iodine. Examples of suitable endocrine therapy include Diethyl bestrol (DES), Tamoxifen, and LHRH antagonizing drugs.

The term "antibody" encompasses whole immunoglobulin as well as immunoglobulin fragments. "Antibody" (Ab) or "polyclonal antibody" and/or "monoclonal antibody" (Mab) as used herein is meant to include intact molecules, such as immunoglobulin G molecules made up of four immunoglobulin peptide chains, two heavy chains and two light chains, as well as fragments thereof (such as, for example, Fab and F(ab')2 fragments) which are capable of binding a hapten or antigen. "Immunoglobulin fragments" are protein molecules related to immunoglobulin, which are known to retain the epitopic binding specificity of the original antibody, such as Fab, F(ab)'$_2$, Fv, etc. Fab and F(ab')$_2$ fragments lack the Fc fragment of intact antibody, clear more rapidly from the circulation, and may have less non-specific tissue binding than an intact antibody (Wahl, et al., *J. Nucl. Med.*, 42:316–325 (1983)).

An antibody is said to be "capable of binding" or "directed against" a molecule if it is capable of specifically reacting with the molecule to thereby bind the molecule to the antibody. The term "epitope" or "binding site" is meant to refer to that portion of an antigen which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens. The antigen of the present invention can be any erbB-2 ligand identified herein, including erbB-2 ligand fragments and synthetic peptides which have amino acid sequences corresponding to erbB-2 ligand sequences. For example, the p75 erbB-2 ligand can be used to generate anti-p75 ligand antibodies according to the present invention.

The antibodies used in the present invention may be prepared by any of a variety of methods. For example, cells producing erbB-2 ligand (or fractions, lysates, etc. thereof) can be administered to an animal in order to induce the production of sera containing polyclonal antibodies that are capable of binding the antigen. Since cells which produce erbB-2 ligand excrete the protein into the culture media, the media may be used as a source of the erbB-2 ligand antigen. In a preferred method, a preparation of the erbB-2 ligand of the present invention is prepared and purified to render it substantially free of natural contaminants. Particularly preferred preparations of erbB-2 ligand are produced by expression of recombinant DNA encoding an erbB-2 ligand in a non-human host cell, since antigens that are found with the erbB-2 ligand in the native state will not be expressed by the recombinant host. Such preparations are then introduced into an animal in order to produce polyclonal antisera of greater specific activity.

The antibodies of the present invention may be monoclonal or polyclonal antibodies (or hapten binding fragments thereof). Such monoclonal antibodies can be prepared using hybridoma technology (Kohler, et al., *Nature*, 256:495 (1975); Kohler, et al., *Eur. J. Immunol.*, 6:511 (1976); Kohler, et al., *Eur. J. Immunol.*, 6:292 (1976); Hammerling, et al., In: *Monoclonal Antibodies and T-Cell Hybridomas*, Elsevier, New York, pp. 563–681 (1981)). In general, such procedures involve immunizing an animal with substantially pure erbB-2 ligand protein.

The splenocytes of the immunized animal are extracted and fused with a suitable myeloma cell line. Any suitable myeloma cell line may be employed in accordance with the present invention; however, a suitable parent myeloma cell line (SP$_2$O), available from the American Type Culture Collection, Rockville, Md., may be used. After fusion, the resulting hybridoma cells are selectively maintained in HAT medium, and then cloned by limiting dilution as described by Wands, et al., *Gastroenterology*, 80:225–232 (1981), which reference is herein incorporated by reference). The hybridoma cells obtained through such a selection are then assayed to identify clones which secrete antibodies capable of binding to the erbB-2 ligand.

It will be appreciated that Fab and F(ab')$_2$ and other fragments of the antibody may be used according to the methods disclosed herein for the detection erbB-2 ligand in samples in the same manner as intact antibody. Such fragments are typically produced by proteolytic cleavage, using enzymes such as papain (to produce Fab fragments) or pepsin (to produce F(ab')$_2$ fragments). Alternatively, hapten-binding fragments can be produced through the application of recombinant DNA technology or through synthetic chemistry.

Similar to blocking peptides, antibodies can be conjugated to the therapeutic agents. Suitable examples of therapeutic agents which may be conjugated to the anti-ligand antibodies of the present invention include, but are not limited to, cytotoxic drugs, toxins, and isotopes. Examples of suitable therapeutic agents are described above.

The polyclonal or monoclonal antibodies produced against gp30 or p75 may be produced in accordance with well-known techniques. For example, see *Current Protocols in Molecular Biology*, edited by F. M. Ausubel, et al. (Wiley 1987), in particular Chapter 11 on Immunology. Also, the immunoassays used in the assays and diagnostic test kits of the present invention are well known to the artisan as evidenced by the above treatise, and by the methods disclosed in U.S. Pat. No. 4,921,790 which patent has been specifically incorporated herein in the entirety.

H. Assays for Detecting erbB-2 Ligand

The 185 kd transmembrane glycoprotein known as p185$^{erbB-2}$ is thought to be a transmembrane protein which functions as a growth factor receptor and is encoded by a protooncogene. The erbB-2 expression is amplified in many adenocarcinomas and, in particular, is amplified or overexpressed in nearly 30% of human breast cancers (Maggurie, et al., *Seminars in Oncology*, 16:148–155 (1989)). Patients with cancer cells which overexpress erbB-2 are known to have much shorter disease-free periods and poorer overall survival than cancer patients that do not show erbB-2 overexpression. Consequently, it is important to distinguish between malignancies which exhibit erbB-2 overexpression from those which do not. Diagnosis of erbB-2 associated cancers thus provide the clinician with a way to pre-select an effective therapy for treating particular types of cancer.

Expression of the erbB-2 protooncogene encoding a 185 kDa transmembrane protein serves as a marker to identify a particular invasive malignant cell type. Since the erbB-2 receptor is a transmembrane protein, its extracellular domain is accessible to interaction with its ligand on the cell surface. Consequently, the ligand of the present invention which binds specifically to $p185^{erbB-2}$ can be utilized to detect cells which express the erbB-2 receptor. Surprisingly, the erbB-2 ligand of the present invention does not cross-react with the EGFR and thus is specific for erbB-2 receptor. Therefore, the erbB-2 ligands of the invention are capable of detecting particular cancer cells in a patient and may not recognize normal cells or malignant cells that fail to overexpress the erbB-2 receptor. This characteristic is important in that early detection of erbB-2 overexpressing malignant cells may indicate prognosis and treatment for the patient.

According to the present invention, diagnosis with the erbB-2 ligands involves the detection of $p185^{erbB-2}$ overexpressing cancer cells in a patient. Detection of such cells in a patient may be accomplished by any of a variety of in vitro assays or in vivo imaging techniques. Examples of these in vitro and in vivo techniques are disclosed in the preferred embodiments described below. The materials for use in the in vitro assays and in vivo imaging techniques which utilize erbB-2 ligand are also ideally suited for preparation of a kit.

The anti-ligand molecules including antibodies, fragments of antibodies, or blocking peptides of the present invention may be used to detect the presence of the erbB-2 ligand. Thus, the antibodies (or fragments thereof) and blocking peptides may be employed in histology and biopsy to detect erbB-2 ligand expression in a patient suffering from breast, liver, ovarian, lung, colon carcinomas and the like. Such detection may be accomplished using any of a variety of assays. For example, by radioactively labeling the antibodies or antibody fragments, it is possible to detect the erbB-2 ligand through the use of radioimmune assays. A good description of a radioimmune assay (RIA) may be found in *Laboratory Techniques and Biochemistry in Molecular Biology*, by Work, et al., North Holland Publishing Company, New York (1978), with particular reference to the chapter entitled "An Introduction to Radioimmune Assay and Related Techniques" by Chard, T., incorporated by reference herein. Alternatively, fluorescent, enzyme, or other suitable labels can be employed. Detectably labeled blocking peptides may be used in an analogous manner to detect the erbB-2 ligand.

The present invention also provides a method of detecting cells which overexpress $p185^{erbB-2}$ in a patient, which generally entails contacting a sample obtained from the patient with a detectably labelled erbB-2 ligand; and detecting the presence of the erbB-2 ligand in the sample using some minor modification of standard radioimmunoassay or radio receptor assay methodology. Generally, the sample may be any one of or combination of the following: body tissue, body fluids such as blood, urine, saliva, tear drops, serum, and cerebrospinal fluid, and/or feces.

Alternatively, the detection of erbB-2 ligand may be accomplished by in vivo imaging techniques, in which the labeled antibodies, fragments thereof, or blocking peptides are provided to a patient, and the presence of the breast, ovarian, liver, lung, or colon carcinoma which expresses erbB-2 ligand is detected without the prior removal of any tissue sample. Such in vivo detection procedures have the advantage of being less invasive than other detection methods, and are, moreover, capable of detecting the presence of antigen-expressing cells in tissue which cannot be easily removed from the patient.

In accordance with the above-discussed assays, antibodies, fragments thereof, or blocking peptides may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels will be readily apparent to one of skill in the art. Suitable non-radioactive isotopic labels for use in the present invention will also be known to one of ordinary skill in the art.

Examples of suitable fluorescent labels include a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, pseudomonas endotoxin and cholera toxin. Examples of chemiluminescent labels include a luminal label, an isoluminal label, an aromatic acridinium ester label, an imidazole label, an acridiniu salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta*, 70:1–31 (1976)), and Schurs, et al. (*Clin. Chim. Acta*, 81:1–40 (1977)). Coupling techniques mentioned in the latter are the glutaraldehyde method, the periodate method, the dimaleimide method, the m-maleimido-benzyl-N-hydroxy-succinimide ester method, all of which methods are incorporated by reference herein.

The detection of the antibodies, fragments of antibodies or blocking peptides can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding antibodies and blocking peptides, or will be able to ascertain the same by use of routine experimentation.

The binding molecules (anti-ligand molecules) of the present invention may also be adapted for utilization in an immunometric assay, also known as a "two-site" or "sandwich" assay. In a typical immunometric assay, a quantity of unlabeled antibody, or fragment of antibody, is bound to a solid support that is insoluble in the fluid being tested (i.e., blood, lymph, liquified, stools, tissue homogenate, etc.) and a quantity of detectably labeled soluble antibody is added to permit detection and/or quantitation of the ternary complex formed between solid-phase antibody, peptide antigen, and labeled antibody. It will be apparent to one of skill that labeled blocking peptide may also be used in place of or combination with the antibody used in the assay according to the invention.

Typical immunometric assays include "forward" assays in which the antibody or blocking peptide bound to the solid phase is first contacted with the sample being tested to extract the antigen from the sample by formation of a binary solid phase antibody-antigen complex or a blocking peptide-antigen complex. After a suitable incubation period, the solid support is washed to remove the residue of the fluid sample, including unreacted antigen, if any, and then contacted with the solution containing an unknown quantity of labeled antibody or labeled blocking peptide (which functions as a "reporter molecule"). After a second incubation period to permit the labeled molecule to complex with the antigen bound to the solid support through the unlabeled antibody or blocking peptide, the solid support is washed a second time to remove the unreacted labeled antibody. This type of forward sandwich assay may be a simple "yes/no" assay to determine whether erbB-2 ligand antigen is present or may be made quantitative by comparing the measure of labeled antibody or labeled blocking peptide with that obtained for a standard sample containing known quantities of antigen. Such "two-site" or "sandwich" assays are described by Wide at pages 199–206 of *Radioimmune Assay Method*, edited by Kirkham and Hunter, E. & S. Livingstone, Edinburgh, 1970.

In another type of "sandwich" assay, which may also be useful to detect the erbB-2 ligand antigen, the so-called "simultaneous" and "reverse" assays are used. A simultaneous assay involves a single incubation step as the antibody or blocking peptide bound to the solid support and labeled antibody or blocking peptide are both added to the sample being tested at the same time. After the incubation is completed, the solid support is washed to remove the residue of fluid sample and uncomplexed labeled antibody or peptide. The presence of labeled antibody or blocking peptide associated with the solid support is then determined as it would be in a conventional "forward" sandwich assay.

In the "reverse" assay, stepwise addition of a solution of labeled antibody or labeled blocking peptide to the fluid sample is followed by the addition of unlabeled antibody or unlabeled blocking peptide bound to a solid support after a suitable incubation period is utilized. After a second incubation, the solid phase is washed in conventional fashion to free it of the residue of the sample being tested and the solution of unreacted labeled antibody or block peptide. The determination of labeled antibody or labeled blocking peptide associated with a solid support is then determined as in the "simultaneous" and "forward" assays.

As explained above, the immunometric assays for erbB-2 ligand antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to the product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise an immuno-absorbent-bound peptide fragment. Such fragment may be bound to a separate solid-phase immunoabsorbent or directly to the inner walls of a container. A second container may comprise detectably labeled antibody or blocking peptide in lyophilized form or in solution.

The carrier may also contain, in addition, a plurality of containers each of which comprises different, predetermined and known amounts of antigen. These latter containers can then be used to prepare a standard curve from which can be interpolated the results obtained from the sample containing the unknown amount of antigen.

One of skill in the art will recognize that in accordance with these assays, a variety of labels and methods of labeling may be used. Examples of types of labels that can be used in the present invention include, but are not limited to, enzyme labels, radioisotopic labels, non-radioactive isotopic labels, fluorescent labels, toxin labels, and chemiluminescent labels. The binding of these labels to the erbB-2 ligand protein may be accomplished using standard techniques commonly known to those of ordinary skill in the art.

As gp30 is known to be produced by MDA-MB-231 breast cancer cells, and is also likely to be produced by other adenocarcinoma cancer cells, the present invention also provides a method for detecting gp30 in patient sera or urine or other body fluids.

Generally, the present conjugates may be used advantageously in a biochemical detection method in which the 30 kDa glycoprotein ligand is bound to a surface and put into contact with aqueous solution containing a tumor portion containing cells which are suspected of overexpressing either EGFR or erbB-2 oncogene. This is conveniently done as either EGFR or p185 may be found on the cell surfaces. If such cells are present, either the EGFR or $p185^{erbB-2}$ will become bound to the ligand. Thereafter, the aqueous solution is separated from the bound antiligand material, and the antiligand material may be conveniently detected with a known detection means associated therewith. For example, an amplified enzyme-linked immunoassay may be used. The surface to which the ligand is bound is treated with one or more agents for limiting the amount of non-specific binding.

Such agents reduce the "noise" arising due to non-specific binding when interpreting the assay.

In accordance with the above procedure, a diagnostic test kit may be constructed in a variety of ways. For example, a test kit may be constructed to contain a vessel containing a test liquid having a surface to which gp30 ligand is bound. This is preferably a multi-well test plate. Also contained is at least one other vessel containing reagent solution. The agent for limiting non-specific binding may be incorporated within a solution of the kit or may have been used to treat the surface of the first vessel before it is supplied. Then, a portion of the tumor or a tumor sample may be worked up into an aqueous solution and put into contact with the bound gp30.

In order to conveniently detect the overexpression of EGFR or erbB-2 oncogene in a human patient it is advantageous to use the well-known sandwich assay technique. For example, one assay method and test kit which may be used in accordance with the present invention are described in U.S. Pat. No. 4,668,639 which is incorporated herein in the entirety.

Hence, the present invention contemplates and is specifically directed to any diagnostic or therapeutic method for the detection of adenocarcinoma cells which overexpress EGFR or erbB-2 oncogene, which method uses the formation of a conjugate between the 30 kDa glycoprotein of the present invention and either EGFR or $p185^{erbB-2}$.

As noted above, the present invention also provides an assay and a test kit for the detection of gp30 using polyclonal or monoclonal antibodies to gp30. Importantly, however, the presence of the 30 kDa glycoprotein (gp30) in patient sera can be detected utilizing either monoclonal or polyclonal antibodies in virtually any type of immunoassay. This includes both single-site or two-site or "sandwich" assays of the non-competitive types, as well as in traditional competitive binding assays. In such an assay, the monoclonal antibodies to gp30 are preferably bound to the microliter or multi-well plate and exposed to patient sera suspected of containing gp30. Upon detecting the presence of gp30 by a conventional detecting means, a conclusion of poor prognosis would be made necessitating the use of more aggressive treatment for the tumor.

With the above assay, a test kit is also provided. Generally, the kit contains a first container containing an antibody having specificity for gp30 and a second container containing a second antibody having specificity for gp30 and being labelled with a reporter molecule capable giving a detectable signal. The first antibody is immobilized on a solid surface. The above assay and test kit for the detection of gp30 may be, respectively, conducted and constructed by analogy in accordance with U.S. Pat. No. 4,921,790, which is incorporated herein in the entirety.

As described above, the diagnostic aspects of the present invention relate to the use of methods and test kits for the detection of either $p185^{erbB-2}$, EGFR or gp30. The detection of any one of these proteins may form the basis for a poor prognosis necessitating the use of aggressive treatment of one or more adenocarcinomas.

Diagnostic uses of the anti-ligand molecules of the present invention may include, for example, detection of erbB-2 ligand in a sample obtained from a patient. Such samples may be body tissue, body fluids (such as blood, urine, tear drops, saliva, serum, and cerebrospinal fluid), feces, cellular extracts and the like. According to the method of detecting erbB-2 ligands, the erbB-2 ligand of the present invention is excreted into vitro into cell culture medium. Another growth factor, TGFα, also secreted in vitro was identified in body fluids of cancer patients. Consequently, the growth factor of the present invention (erbB-2 ligand) may be detected in body fluids, stools, etc. from a cancer patient.

Assaying for the erbB-2 ligand of the invention in a sample obtained from a patient may thus provide for a method for diagnosing cancer. That is, detection of erbB-2 ligand in a sample obtained from a patient indicates the presence of erbB-2 ligand-expressing cells in a patient. Cancer patients with adenocarcinoma cells that overexpress the erbB-2 receptor are known to have a much shorter disease-free period and poorer overall survival than cancer patients that do not show erbB-2 overexpression. Detection of erbB-2 ligand growth factor may thus serve as a prognostic test, allowing the clinician to select a more effective therapy for treating the patient.

I. Therapeutic Uses of erbB-2 Ligand

The erbB-2 ligand of the present invention may be used both diagnostically and therapeutically. Specifically, the erbB-2 ligand may be used to detect, in a patient, adenocarcinoma cells which overexpress the erbB-2 receptor protein. Treatment of such a patient to growth inhibit or destroy these cells may also be accomplished according to the present invention.

The erbB-2 ligand of the present invention may be used to treat a patient suffering from cancer. Treatment therapies with erbB-2 ligand are specifically targeted against cells which may bind to the erbB-2 ligand of the present invention. In this manner, malignant cells that overexpress the erbB-2 receptor (or related receptors) may be growth inhibited or destroyed by the treatment method of the present invention. It will be appreciated that a number of therapeutic uses of the erbB-2 ligand of this invention may be devised. Thus, the present invention is not meant to be limited to the therapeutic treatments described, and they are only presented by way of illustration.

One aspect of cancer treatment using the erbB-2 ligand of this invention concerns the use of ligand-therapeutic agent conjugates. The erbB-2 ligand conjugates of the invention may bind to the adenocarcinoma cell which overexpress the erbB-2 receptor. Once the erbB-2 ligand conjugate is bound to the cell, the therapeutic agent is capable of killing or inhibiting the growth of that cell.

In this manner, administration of an effective amount of ligand conjugate to a patient serves as a treatment that may destroy or inhibit growth of particular types of cancer cells in vivo. Normal cells are not affected by administration of the ligand-therapeutic agent conjugate of this invention.

A second aspect of treatment using the erbB-2 ligand of the present invention relates to the inhibitory affects of the growth factor. Surprisingly, the erbB-2 ligand of the present invention acts, in sufficient concentrations, as an inhibitor capable of inhibiting or suppressing proliferation of adenocarcinoma cells. Any of a number of cancer cells may be growth inhibited with the erbB-2 ligand of the present invention, provide that the erbB-2 ligand can interact with the cell. Typically, malignant cells which overexpress the erbB-2 receptor are inhibited. Such cells may include, but are not limited to, breast, lung, ovarian, gastric, thyroid, prostate or salivary gland carcinoma cells. Cells not affected by the erbB-2 ligand of the invention include normal cells and malignant cells which do not overexpress the protooncogene coding for the erbB-2 receptor.

In vitro or in vivo inhibition of tumor cells may be accomplished by administration of an effective amount of the erbB-2 ligand of the present invention. One of skill in the art will recognize that the amount sufficient to inhibit cell growth varies depending on the cell type, the body weight of the patient, the type of therapeutic agent used etc. These variables can easily be determined by those skilled in the art with little experimentation.

For example, the 30 kDa glycoprotein of the present invention may be used advantageously to inhibit the growth of various types of adenocarcinoma cells which overexpress the erbB-2 oncogene and/or EGFR. Preferably, the present 30 kDa glycoprotein is used in inhibit the growth of adenocarcinoma cells of breast, ovarian, gastric and lung tissue which overexpress the erbB-2 oncogene and EGFR.

The therapeutic aspects of the present invention relate to the use of gp30 to inhibit the growth of adenocarcinoma cells which overexpress EGFR and/or erbB-2 oncogene. Generally, the amount of gp30 to be administered as a therapeutic agent will be determined on a case by case basis by the attending physician. As a guideline, the extent of the adenocarcinoma, body weight and age of the patient are considered while up to about 10,000 ng per day may be used, generally not more than 1,000 ng per day of gp30 is administered. It is preferred, however, if from about 5–500 ng per day are used. Notably, however, the above amounts may vary on a case-by-case basis.

In using the present 30 kDa glycoprotein to control the growth of the above malignant cells in a mammal, preferably a human, relatively high or low concentrations of the glycoprotein may be used. For example, to stimulate cell growth, an aqueous solution having a concentration of about 1–50 ng/ml may be conveniently administered to a patient such that a total of from about 1–10,000 ng of glycoprotein are administered per day. It is preferred, however, if about 1–1000 ng are administered per day. Alternatively, to inhibit cell growth, an aqueous solution having a concentration greater than 1 mg/ml may conveniently be administered to a patient such that concentrations are achieved which will directly inhibit overexpressing cells.

While the present 30 kDa glycoprotein may be administered by itself, as a therapeutic agent, it may be administered in combination with one or more other therapeutic agents. For example, the 30 kDa glycoprotein may be administered with any chemotherapeutic substance, growth inhibitor or immune-stimulating substance. The present invention specifically contemplates such combinations.

gp30, when used in very low (pm) concentrations, may be used to simulate the growth of cells overexpressing erbB-2.

As indicated above, however, the amount of gp30 to be administered for an inhibitory or stimulatory effect will generally be determined on a case-by-case basis by the attending physician. Generally, a lesser amount of gp30 is required to exhibit a stimulatory effect than is required to exhibit an inhibitory effect. The appropriate amount may be readily determined using human cell samples or by considering various factors for the patient on a case-by-case basis.

Further, the gp30 of the present invention is generally administered in solution form by intravenous injection using a solution having a concentration of gp30 of about 0.1 mg to 1 mg per ml of solution. The solution may be an aqueous solution, a saline solution as used in clinical practice or dextrose 5% saline solution.

Thus, the present invention provides a substantially pure erbB-2 ligand or functional derivative thereof, which ligand has a molecular weight of about 30 Kd, and which is capable of binding to erbB-2 receptor protein, $p185^{erbB-2}$.

Generally, in accordance with the present invention, at the lower end of the concentrations expressed above, such as in the range of about 0.05 ng to about 1 μg, preferably about 0.1 ng to about 1 ng, the present erbB-2 ligand conjugate stimulates the growth of malignant cells which express erbB-2.

The use of erbB-2 ligands that do not bind to EGFR such as p75 may be preferred for treatment of some cancers. The above procedures for therapy will also apply to such ligands.

The amounts of erbB-2 ligand of the present invention used in treatment of cancer will generally be related to the amount of erbB-2 ligand that has been shown to be effective when administered to cells of the same type in vitro. Levels of erbB-2 ligand that induce proliferation of cells in vitro are considered stimulatory, while concentrations that induce differentiation of cells in vitro are generally considered inhibitory. The erbB-2 ligand will be administered in a manner and amount so that the circulating concentration of the ligand is similar to the concentration found to be effective in vitro. Generally, the circulating concentration will be from about 0.05 ng/ml to 1 μg/ml, where stimulatory concentrations are generally below 1 ng/ml and inhibitory concentrations are generally above about 1 ng/ml.

J. Therapeutic Uses of Anti-Ligand Molecules

The anti-ligand molecules of the present invention have a multitude of therapeutic and diagnostic uses. For example, therapeutic uses may involve cancer therapy in a patient suspected of suffering from cancer. Specifically, the anti-ligand molecules of the present invention such as antibodies or blocking peptides may be used to treat patients that have adenocarcinoma cells which produce the erbB-2 ligand and/or overexpress the erbB-2 receptor proteins.

One type of treatment may involve the use of the antibody conjugated to a therapeutic agent. Blocking peptide coupled to a therapeutic agent may be used in an analogous manner. By administering an effective amount of anti-ligand coupled to the therapeutic agent to a patient, the adenocarcinoma cells in the patient which express erbB-2 ligand and/or a erbB-2 receptor can be growth inhibited or killed, thereby providing a treatment for cancer. Normal and malignant cells which overexpress EGFR are not affected by administration of the anti-ligand-therapeutic conjugate agent to a patient. Thus, treatment of a patient with the anti-ligand conjugate may selectively inhibit or destroy erbB-2 overexpressing cancer cells in vivo.

In accordance with the method of cancer treatment of the invention, the conjugated anti-ligand is capable of recognizing and binding to carcinoma cells due to the carcinoma cells association with the erbB-2 ligand. Without being limited, the mechanism of binding to the cancer cell may involve the recognition of erbB-2 ligand located on the cell surface or because of expression and/or secretion of the ligand.

Once the conjugated anti-ligand is bound or in close association with the adenocarcinoma cell by interacting with ligand, the therapeutic agent is capable of inhibiting or killing that cell. In this manner, the therapy of the present invention is selective for a particular target, i.e., cancer cells which are associated with the erbB-2 ligand. Normal cells and other cells not associated with the erbB-2 ligand (cells which do not express or bind erbB-2 ligand) may not, for the most part, be affected by this therapy.

Alternatively, the anti-ligands of the present invention may be used to prevent or inhibit inducement of adenocarcinoma cell proliferation. For example, cancer cells which contain the $p185^{erbB-2}$ receptor are induced to proliferate in the presence of low concentrations of erbB-2 ligand. Preventing the erbB-2 ligand growth factor from interacting with its receptor may provide a means to treat a cancer patient.

According to the method of inhibiting cellular proliferation of the present invention, the anti-ligand is capable of binding to the erbB-2 ligand. Binding the excreted erbB-2 ligand in vivo forms a ligand-anti-ligand complex and thus may prevent or inhibit the ligand-receptor interaction either sterically or otherwise. Thus, the present invention provides a treatment to prevent or inhibit adenocarcinoma cell proliferation in a patient by administering an effective amount of an anti-ligand to such a patient.

It will be appreciated that a number of other therapeutic uses of the anti-ligands of the present invention may be devised. Such therapies may involve use of other known treatment techniques in combination with the anti-ligands of the invention. The present invention is not meant to be limited by the therapeutic treatments described which are only presented by way of illustration.

Furthermore, administration of an effective amount of the anti-ligands of the present invention sufficient to inhibit or kill an adenocarcinoma cell may vary depending upon a number of factors including the type of malignant cell, body weight of the patient, the type of therapeutic agent used and the like. Those of skill in the art will appreciate that the amount necessary to inhibit or kill a particular malignant cell in vitro or in vivo can easily be determined with minimal experimentation.

In order to further exemplify the present invention, reference will now be made to certain examples which are provided solely for purposes of illustration and are not intended to be limitative.

Cell Lines

Cells from the following sources were used in the Examples: MDA-MB-231 SKBr-3, MDA-MB-453, BT-474, and NRK clone 49F fibroblasts were obtained from the American type Culture Collection (Rockville, Md.). Hs578T cells, A431 cells, and H8 cells, a TGFα-transfected MCF-7 breast cancer cell line, were available upon request from a variety of sources. Carcinogen-immortalized normal mammary epithelial cell subline 184A1N4 and its SV40-transfected derivative 184A1N4T, were also available on request. Rat-FeSrV transfected cells were also provided upon request. All cell lines were propagated in improved modified Eagle's medium (IMEM, Gibco, Grand Island N.Y.) supplemented with 10% fetal bovine serum (FBS, Gibco).

Conditioned Media Preparation, Collection and Concentration

Conditioned media collections were carried using a well-known procedure. The media were concentrated 100-fold in an Amicon ultra-filtration cell (YM5 membrane) (Amicon, Denvers, Mass.). Once clarified and concentrated, the media were stored at −20° C. while consecutive collections were made during the following days. The concentrated media were dialyzed using Spectraphore 3 tubing (Spectral Medical Industries, Los Angeles, Calif.) against 100 volumes of 0.1M acetic acid over a two-day period at 4° C. The material that precipitated during dialysis was removed by centrifugation at 4000 rpm for 30 min. at 4° C.; protease inhibitors were added. The clarified sample was then lyophilized. The following Examples are provided solely for the purpose of illustrating the present invention and are not intended to be limitative.

In order to further describe the various aspects of the present invention, reference will now be made to the figures of the present specification.

EXAMPLE 1

Identification of a TGFα-like Polypeptide in MDA-MB-231 Human Breast Cancer Cells To determine whether the 30 kDa TGFα-like protein was recognized by antibodies developed against mature 6 kDa TFGα, MDA-MB-231 cells were metabolically labelled with [$^{35}$S] methionine and [$^{35}$S] cysteine.

Cells were grown to 80% confluence in IMEM. Cell monolayers were washed three times with PBS and incubated for two hours in serum-free IMEM which lacked methionine and cysteine and was supplemented with glutamine (2.9 g/l) (Biofluids, Rockville, Md.). This medium was then removed and replaced with serum-free IMEM without methionine and cysteine containing 2.5 mCi/ml [$^{35}$S] cysteine and methionine (Amersham, Arlington Heights, Ill., 1175 Ci/mmole). A total of 2.5 ml of this medium was used for a 5 cm dish. The medium was harvested from the culture after 16 hrs at 37° C. and clarified by centrifugation. Cells were washed once with PBS, harvested by scraping, and lysed in 1 ml of RIPA buffer (300 mM NaCl, 100 mM Tris-HCl, containing 2% Triton X 100, 2% Nadeoxycholate, 0.2% SDS, 0.4% BSA and 2 mM PMSF). Following an incubation of 30 minutes on ice, the lysate was clarified by centrifugation (30 minutes at 4000 rpm) and used immediately or was stored at −70° C.

Metabolically labelled conditioned media from MDA-MB-231, TGFα-transfected MCF-7 (H8), and HS578T cells were tested by solid phase RIA for immunoreactivity with a polyclonal antibody (R399) and a monoclonal antibody raised against recombinant 6 kDa TGFα.

Polyclonal and Monoclonal Antibodies

Polyclonal Antibodies Antiserum against human TGFα was obtained by immunization of a rabbit on day 0 with 400 g of recombinant TGFα synthesized in E. coli, provided by Genentech Corp. The immunogen was first conjugated to keyhole limpet hemocyanin (KLH) and was emulsified in complete Freund's adjuvant and was injected intradermally at multiple sites. Additional injections were given as follows: day 60, 175 g TGFα and days 90, 150, 180, and 210, 100 g TGFα. The booster injections were given subcutaneously at multiple sites in incomplete Freund's adjuvant. The rabbit serum was assayed for antibody titer by ELISA at 10 to 14 days following each injection. The antiserum collected at day 180, designated R399, was used for immunoprecipitation and radioimmunoassay.

Monoclonal Antibodies A monoclonal antibody against recombinant TGFα was kindly provided by Genentech Corp.

Measurement of Anti TGFα Antibody (R.399) Levels by ELISA

Micro-Elisa plates (Dynatech-Immunolon II, Dynatech Laboratories, Inc. Chantilly Va.) were coated for 16 hours at 4° C. with 500 ng/ml of recombinant TGFα in 50 mM sodium carbonate buffer (pH 9.6). The samples to be assayed (antibody) were serially diluted 1:1,000–1:64,000 with 0.15M NaCl, 0.05M Tris-HCl (pH 7.4), 2 mM EDTA, 5 mg/ml bovine serum albumin, 0.05% Tween 20 (TBS-BSA-Tween) and were incubated in the wells for 2 hours at 37° C. The plates were washed five times with PBS-Tween and then incubated for 1 hr at 37° C. with horseradish peroxidase-conjugated goat anti-rabbit immunoglobulin in TBS-BSA-Tween. The plates were then washed five times with PBS-Tween and incubated for 4 hrs at 22° C. with 100 l per well of 0.1 mg/ml o-phenylenediamine, 0.012% $H_2O_2$ in 0.1 M Phosphate-citrate buffer (pH 5.0). The reaction was stopped by the addition of 50 l/well of 2.5N $H_2SO_4$ and the absorbance was measured at 492 nm using a UR 700 Microplate Reader (Dynatech Lab., Inc., Chantilly, Va.).
Radioimmunoassay (RIA)

TGFα RIA The presence of peptides immunologically related to TGFα was determined using a RIA kit with a polyclonal anti-rat TGFα and rat [$^{25}$I] TGFα (Biotope, Inc., Seattle, Wash.). This antibody does not cross-react with human EGF. Aliquots of conditioned media were reduced with 40 mM dithiothreitol and denatured by immersion for 1 minute in a boiling water bath. Assays were done in duplicate according to the manufacturer's protocol and each collection of conditioned media was assayed at least twice.

Solid Phase RIA 96 well microtiter plates were coated with anti-TGFα antibody (R399 or monoclonal antibody) for 2 hours at 37° C. The wells were then filled with 100 l of the column fraction to be assayed for TGFα activity. A standard curve was constructed using 0.075 to 15 ng unlabelled TGFα. After the 2 hours incubation $5 \times 10^4$ cpm of [$^{125}$I] TFGα or $2 \times 10^5$ cpm of metabolically labelled antigen was added per well. The plates were incubated further for 16 hours at 4° C. The wells were washed and counted using a gamma counter (Model B5002, Packard Instruments Co., Sterling, Va.). The EGF RIA was performed with an anti-EGF antibody (Oncogene Science clone 144-8, Manhasset, N.Y.). A standard curve was constructed using human EGF (hEGF, receptor grade, Collaborative Research, Waltham, Mass.).

Metabolically labelled TGFα-like material from MDA-MB-231 cells reacted only with the polyclonal antibody. In contrast, the two antibodies cross-reacted with metabolically labelled material derived from H8 cells and no immunoreaction was noted with pre-immune serum (normal rabbit serum, NRS) or metabolically labelled conditioned media from Hs578t breast carcinosarcoma cells (FIG. 1), which do not produce TGFα mRNA. Thus only the monoclonal antibody is able to distinguish between TGFα and the TGFα-like material from MDA-MB-231 cells. Specificity of the assay was demonstrated using a competition RIA with unlabelled recombinant TGFα.

Labelled material from MDA-MB-231, H8, and Rat-FeSrV cells was immunoprecipitated with the anti-TGFα polyclonal antibody. [$^{35}$S]-labelled proteins released into the conditioned media by the different cell lines were immunoprecipitated with 10 μg (specific or non-specific antibody) partially purified by 45% ammonium sulfate precipitation. After solubilization, the immuno-precipitates were analyzed by 15% SDS-PAGE and subsequent fluorography. Prestained molecular weight markers (Biorad, Richmond, Calif.) were run in parallel lanes.

Detection of an immunoreactive species of approximately 30 kDa size verified the secretion of a higher molecular weight TGFα-like polypeptide in MDA-MB-231 cells. H8 cells, which overexpress classical TGFα, yielded a 6 kDa product. The expected 18 kDa precursor of the classical 6 kDa TGFα was precipitated from Rat-FeSrV, which are known to secrete the "normal" precursor. The intensity of the bands diminished when the immunoprecipitation was performed in the presence of excess unlabelled TGFα. No specific bands were immunoprecipitated by pre-immune rabbit serum.

EXAMPLE 2

Identification of erbB-2 Ligands

A monoclonal antibody (4D5) radioreceptor assay was used to screen conditioned media derived from different human cell lines for the presence of $p185^{erbB-2}$ binding activity. Conditioned media was collected as described by Bates, et al., *Cancer Res.* 46:1707–1713 (1986). Briefly, media were concentrated 100-fold in an Amicon ultrafiltration cell (YM5 membrane) (Amicon, Denvers, Mass.). Once clarified and concentrated, the media were stored at −20° C. while consecutive collections were made during the following days. The concentrated media were dialyzed using Spectraphore 3 tubing (Spectral Medical Industries, Los Angeles, Calif.) against 100 volumes of 0.1M acetic acid over a two day period at 4° C. The material that precipitated during dialysis was removed by centrifugation at 4000 rpm for 30 min. at 4° C.; protease inhibitors were added as described by Bates, et al., *Cancer Res.*, 46:1707–1703 (1986).

A monoclonal antibody, 6E9, (Fendly, et al., *Cancer Res.*, 50:1550–1558 (1990)) against the extracellular domain of $p185^{erbB-2}$ which does not compete with gp30 for $p185^{erbB-2}$ binding was used as a control, to rule out the possibility that the erbB-2 oncoprotein or the portion of it that is shed from the cells into their growth media might interfere with the 4D5 assay. Shed erbB-2 extracellular domain would compete with the binding of both 4D5 and 6E9 to $p185^{erbB-2}$, as opposed to a erbB-2 ligand which would compete exclusively with 4D5. Any antibody which is directed against the $p185^{erbB-2}$ extracellular domain can be used as a control antibody in place of 6E9, provided that the control antibody does not interfere with 4D5 or MO193 binding, i.e., that the control antibody and the test antibody do not bind the same binding site on the extracellular domain.

Binding assays were performed as described (Lupu, et al., *Science,* 249:1552 (1990)). Proliferating SK-Br-3 cells were incubated with iodinated anti-erbB2-antibodies (4D5 or 6E9) in the presence of several concentrations of conditioned media. Media derived from SK-Br-3, MCF-7, HS578T, MDA-MB-453, BT-549, MDA-MB-468, and MDA-MB-157 breast cancer cells, as well as several non-malignant and transformed breast epithelial cells (Cell lines studied were non-malignant breast epithelial 184 cells, immortalized 184A1N4 cells and oncogene-transformed 184A1N4T (SV-40), 184A1N4H (ras), 184A1N4M (myc), 184A1N4TH (SV-40, myc), and 184A1N4MH (myc, ras) cells were evaluated.) Conditioned media from MDA-MB-231 cells were used as a positive control since these cells were known to secrete gp30. Only one of the 15 different media tested, that from SK-Br-3 cells, showed an ability to compete with 4D5 for $p185^{erbB-2}$ binding.

EXAMPLE 3

Purification of the TGFα-like Polypeptide

TGFα-like material was isolated from serum-free conditioned media of MDA-MB-231 cells. Levels of TGFα-like polypeptide were quantified by three independent assays: capacity to induce anchorage-independent growth of NRK fibroblasts in soft agar, ability to compete with [$^{125}$I] EGF for EGF receptor binding on A431 human carcinoma cell membranes-and cross-reactivity with polyclonal antibodies raised against mature TGFα. EGF receptor binding activity and TGFα immunoreactivity were detected using a RIA kit provided by Biotope.
EGF Radioreceptor Assay A431 membranes were prepared according to the method of Kimball and Warner. A431 cells were disrupted under nitrogen and the nuclei and organelles pelleted by low speed centrifugation. The membranes were then pelleted by centrifugation at 35,000 rpm for 1 hour and resuspended in 20 mM HEPES buffer, pH7.4. Membranes (2.5 g/ml) were plated into 96 well plates and allowed to dry overnight at 37° C. before use. Standard binding competition studies were performed using [$^{125}$I] EGF (ICN, Costa Mesa, Calif., specific activity—100 Ci/g, about 50,000 CPM/well). A standard curve was constructed with 0.075–10 ng of unlabelled hEGF (receptor grade, Collaborative Research). The different fractions to be analyzed were lyophilized and reconstituted in PBS (0.5 ml/500 ml conditioned media). After incubation of the labelled EGF and 10 l of the samples for 2 hours at 37° C. in binding buffer (IMEM containing 50 mM HEPES and 0.1% BSA pH 7.7), the wells were washed, cut from the plate and counted. EGF-competing activity, was computed using a Hewlett Packard RIA Program.

Molecular Filtration Chromatography

To determine the approximate molecular weight of the MDA-MB-231 derived TGFα-like polypeptide, 5 ml of 100-fold concentrated, dialyzed conditioned medium was chromatographed by gel filtration using Sephadex G-100. Lyophilized conditioned medium was dissolved in 1M acetic acid to a final concentration of about 25 mg/ml total protein. Insoluble material was removed by centrifugation at 10,000 rpm for 15 minutes. The sample was then loaded onto a Sephadex G-100 column (XK 16, Pharmacia, Piscataway, N.J.), was equilibrated and was subjected to elution with 1M acetic acid at 4° C. with an upward flow of 30 ml/hr. 100 ng of protein was processed from 4 ml of 100-fold concentrated medium. Fractions containing 3 ml of eluate were lyophilized and resuspended in 300 1 PBS for assay and served as a source for further purification.

Elution was performed with 1.0M acetic acid and fractions were characterized for protein content. TGFα-like activities were eluted from the column in a single broad peak. Maximal activity was observed at an apparent molecular weight of 30 kDa and was separated from the bulk of contaminating proteins present in the bed volume. All the fractions demonstrating TGFα immunoreactivity also contained EGF receptor binding activity. The relative amounts of receptor binding activity and immunoreactivity present in these fractions, however, appeared to differ.

Heparin Affinity Chromatography

Further analysis of the TGFα-like polypeptide from MDA-MB-231 cells was carried out using heparin-sepharose affinity chromatography. Heparin-sepharose affinity chromatography was performed on unconcentrated conditioned media from MDA-MB-231 cells.

Media conditioned by MDA-MB-231 cells were clarified by centrifugation for 20 minutes at 2,000 rpm at 4° C. The supernatant was collected and stored at −70° C. After allowing the heparin-sepharose (Pharmacia, Piscataway, N.J.) to expand-in PBS, 2 ml of gel was loaded on an Econo column (Biorad, Richmond, Calif.) and washed with about 100 bead volumes of PBS. Conditioned media were run through the beads by gravity (flow rate 20 to 50 ml/hr). The gel was then washed with 5 volumes of PBS and eluted stepwise with an increasing gradient of NaCl in 10 mM Tris-HCl, pH 7.0 (elution buffer). Gradient steps of 0.4M, 1.1M, 2.0M and 3.0M NaCl were used in the elution buffer until the 280 nm absorption during each step returned to baseline (usually 3 to 5 column bed volumes). The eluate was desalted on G-25 columns (Pharmacia, Piscataway, N.J.) and filter-sterilized before use in the different bioassays. Pooled fractions containing active materials were also desalted on PD10 columns (Pharmacia, Piscataway, N.J.) before running through HPLC and FPLC.

In all experiments, less than 20% of the TGFα activity loaded onto the column was recovered in the unabsorbed fractions. A sharp peak of erbB-2 phosphorylation activity and EGF receptor binding activity was eluted by heparin-sepharose chromatography at a concentration of 0.6–0.9M NaCl. This activity represented one major 30 kDa molecular weight protein, which retained 70%–80% of the load activity.

FIG. 1A illustrates the use of low affinity heparin chromatography. In particular, affinity chromatography of conditioned media from MDA-MB-231 cells was performed on a heparin-sepharose column. Fractions were analyzed for EGF receptor binding activity of A431 cell membranes. Aliquots from the input media and from the fractions containing activity were analyzed by a 15% SDS-PAGE, followed by silver staining. Lane 1 shows unconcentrated conditioned media. Lane 2 represents the active fraction.

Reversed-Phase High Pressure Liquid Chromatography (HPLC) The TGFα-like polypeptide (the erbB-2 ligand) was further purified by reversed phase chromatography (HPLC) in two steps. A pool of fractions containing EGF receptor-competing activity from heparin-sepharose chromatography was reconstituted in 0.05% TFA in water and then chromatographed on a Bondapak C$_3$ column. A steep acetonitrile gradient (0–100%) was used in this step. TGFα-like polypeptide elutes as a sharp peak in 30% acetonitrile and is separated from the bulk of the contaminating proteins. Steep Acetonitrile Gradient Steep acetonitrile gradient and all other HPLC steps were carried out at room temperature after equilibration of the C3-Reversed phase column with 0.05% TFA (Trifluoroacetic acid) in water (HPLC-grade). The samples were loaded and fractions eluted with a linear gradient (0–45% acetonitrile in 0.05% TFA) at a flow rate of 1 ml/min over a 30 minute period. Absorbance was monitored at 280 nm. One ml fractions were collected and lyophilized before analysis for EGF receptor-competing activity. The capacity of the individual fractions to compete for EGF receptor binding (as described above) and to stimulate the growth of NRK cells in soft agar was determined.

Soft agar cloning assays (anchorage-independent growth assays) were carried out using a 1 ml bottom layer of IMEM containing 0.6% Bacto-agar (Difco, Detroit, Mich.), 10% FBS, and 2 mM glutamine in 35mm tissue dishes (Costar, Cambridge, Mass.). A 0.8 ml top layer of IMEM containing the test samples, 0.36% agar, 10% FBS, and 3×10$^4$ NRK cells was added after solidification of the bottom layer. Each sample was plated in triplicate. All samples were sterilized by filtration using a 0.22 m Millex CU millipore filter before plating. Plates were incubated in a humidified, 5% CO$_2$ atmosphere at 37° C. and were counted after 12 days incubation with a Bausch and Lomb Stem Cell Colony Counter (Artex Systems Corp, Farmingdale, N.Y.).

Shallow Acetonitrile Gradient A pool of the active fractions was rechromatographed on the same column. Generally, fractions were eluted with an 0–20% acetonitrile gradient in 0.05% TFA for 5 minutes followed by a linear 20–40% acetonitrile gradient. The TGFα-like polypeptide activity was eluted at 25–30% acetonitrile and effectively separated from other contaminant proteins.

In a particular experiment, the pool of active fractions from the previous HPLC step was rechromatographed over the same column. Elution was performed with a 0–18% acetonitrile gradient in 0.05% TFA over a 5 minute period followed by a linear 18–45% acetonitrile gradient in 0.05% TFA over a 30-minute period. The flow rate was 1.0 ml/min and 1 ml fractions were collected. Human TGFα-like factor was eluted at a 30–32% acetonitrile concentration as a single peak detectable by RRA.

FIG. 1B illustrates the use of reversed-phase chromatography. Notably, the EGF/TFGα-active fractions obtained after heparin-sepharose chromatography were chromatographed twice on a μBondapak C$_3$ column in 0.05% TFA. Samples were eluted with a steep gradient of acetonitrile. Fractions that showed EGF receptor binding activity were then rechromatographed and eluted with a shallow acetonitrile gradient. EGF competing activity was constantly eluted at a 25–30% acetonitrile gradient. The resulting fraction was analyzed on a 15% SDS-PAGE followed by silver staining. Sizes are shown in kilodaltons.

In order to achieve a complete separation of TGFα-like polypeptide from those impurities detected by silver staining (data not shown) we used size exclusion chromatography under acidic conditions. The active fractions for erbB-2 phosphorylation or EGF receptor-competing activity were pooled and analyzed by SDS-PAGE. One single polypeptide band was observed after silver staining.

A summary of the steps leading to the isolation and purification of TGFa-like polypeptide is presented in Table 1. A 27% recovery of activity and approximate 5400 fold purification was achieved.

TABLE 1

Purification of TGFα-Like Activity
from Conditioned Medium from MDA-MB-231 Cells*

| Purification Step | Protein Recovered[a] (mg) | EGF Competing Activity[b] (Units/mg TGFα) | Relative Specific Activity (Units/mg protein) | Degree of Purification (fold) | Recovery (% Activity) |
|---|---|---|---|---|---|
| Conditioned Medium | 98 | 450 | 4.6 | 1 | 100 |
| Acid-Soluble Supernatant | 82 | 419 | 5.1 | 1 | 93 |
| Gel Filtration | 2.95 | 209 | 70.8 | 15.3 | 46 |
| 1-Heparin-Sepharose | 1.54 | 230 | 149 | 32.3 | 51 |
| 2-Reverse Phase[c] | 0.03 | 173 | 5768 | 1253 | 38 |
| 3-Reverse Phase[d] | 0.006 | 124 | 24800 | 5400 | 27 |

[a]Total protein was determined using BSA as a standard. The quantitation of step 6 was based on extrapolation from standard values. The absolute specific activity of a comparison aliquot was found to be 1 million units/mg.
[b]One unit of EGF competing activity is defined as the amount of protein that inhibits the binding of [$^{125}$I]EGF to the receptor by 50%.
[c]Steep acetonitrile gradient.
[d]Shallow acetonitrile gradient.
1-2-3: Subsequent purification steps
*Each value represents the mean of 4–6 experiments and they were reproducible within 10%.

EXAMPLE 4

Characterization and Purification of the erbB-2 Ligand

Since SK-Br-3 cells seemed to secrete a erbB-2 ligand, our next step was to determine whether the putative ligand showed heparin binding, which would be consistent with the secretion of gp30. No p185$^{erbB-2}$ binding activity was detected after media from SK-Br-3 cells was processed by heparin chromatography, suggesting that either gp30 was not present in the media or, since SK-Br-3 cells release p185$^{erbB-2}$ extracellular domain (ECD) into the culture media, that ECD might interfere with heparin binding or might be washed off the column bound to the extracellular domain.

Our next step was to develop a purification procedure which would not interfere with p185$^{erbB-2}$ ECD. Recombinant p185$^{erbB-2}$ extracellular domain (ECD) (obtained from Genentech Inc., California) was coupled to a polyacrylamide-hydrazide sepharose affinity chromatography matrix (Avromeas, et al., Scand. J. Immunol., 8:7 (1978)). The molecular weight of this extracellular domain is approximately 94 kilodalton.

erbB-2 extracellular domain (ECD) was coupled to polyacrylamide-hydrazide Sepharose beads (Sigma). After extensive washes of the beads (5 volumes) with ice-cold 1.0M HCl, the beads were activated with 0.5M NaNO$_2$ (1 volume). The temperature was maintained at 0° C. for 15–20 minutes, then the beads were filtered on a sintered glass funnel and washed with ice-cold 0.1M HCl. The beads were immediately washed with 0.1M sulphamic acid and then ice-cold water, and resuspended in 0.2M NaHCO$_3$, pH 6.0 (10 volumes).

The coupling was tested by demonstrating the binding of iodinated 4D5 antibody to the column. Other antibodies such as MOI93 can also be used.

The percent of EDC binding to the sepharose beads was between 90–98%. 1.0 ml of gel was loaded on an Econo column (Biorad, Richmond, Calif.) and washed with about 100 bead volumes of PBS. After the column was packed, conditioned media, derived from SK-Br-3 human breast cancer cells, were run through the beads by gravity (flow rate 30 ml/hr). The column was then washed with 5 volumes of PBS and eluted stepwise with 1.0M Citric Acid at different pHs (from 4.0 to 2.0). Usually 10 bed volumes of each pH solution were employed. All fractions were desalted on PD10 columns (Pharmacia, Piscataway, N.J.) before testing their biological activity. Aliquots from the input media and from the fractions containing activity were analyzed by a 10% SDS-PAGE, followed by silver staining.

Concentrated conditioned media from SK-Br-3 cells (clones 21, 22) were loaded onto the column and elution of the material obtained was performed stepwise with 1.0M Citric Acid across a pH range from 4.0 to 2.0, to allow the dissociation of the erbB-2 ECD and putative ligand. The fractions were tested for their p185$^{erbB-2}$ binding properties in the 4D5 binding assay.

Figure 7:
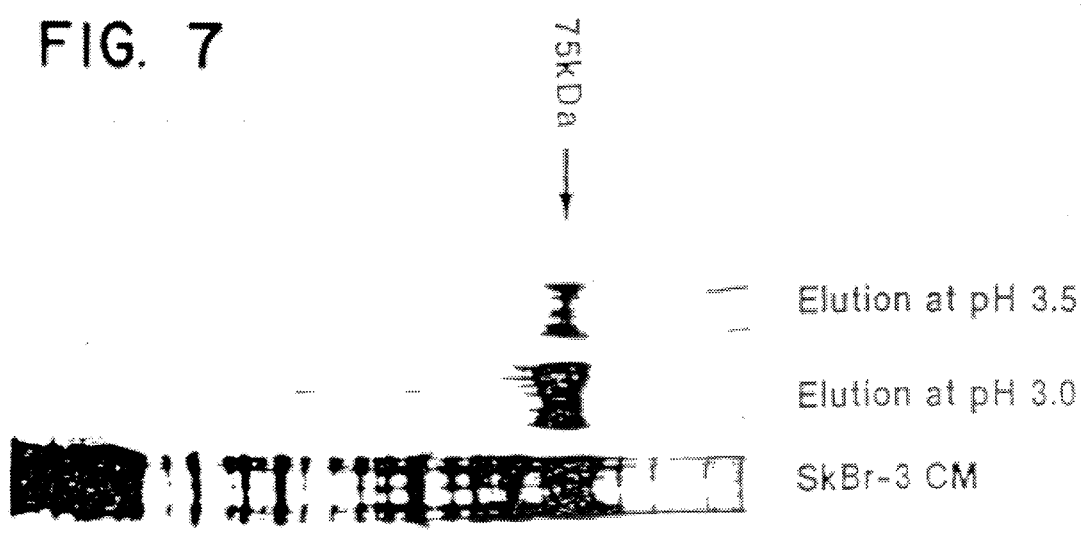
FIG. 7 shows SDS-polyacrylamide gel electrophoresis of samples eluted from an affinity column coupled to p185$^{erbB-2}$ extracellular domain.

A single purification yielded an apparent homogeneous polypeptide of 75 kilodaltons at 3.0–3.5 elution pH. The homogeneity of the sample was confirmed by analysis on a SDS-PAGE (Laemmli U. K., Nature, 227:680 (1970)) by silver staining (Morissey, J. H., Anal. Biochem., 177:307 (1981)) (FIG. 7). Lane 3 shows unconcentrated conditioned media from SK-Br-3 cells (clones 21, 22). Lane 2 represents the elution at pH 3.0, lane 1 represents the elution at pH 3.5. Sizes are shown in kilodaltons. This preparation was the source used for further experiments.

To confirm that the 75 kDa polypeptide (p75) obtained from the ECD affinity column at pH 3.0–3.5 elution of SK-Br-3 conditioned media was indeed a ligand for the erbB-2 oncoprotein we used two independent assays. We first confirmed, with the 4D5 radioreceptor assay, that p75 (eluted at pH 3.0–3.5) binds specifically to the erbB-2 receptor in SK-Br-3 cells, while material from other chromatography fractions or flow-through did not show such activity (Table 2). The binding of iodinated 6E9 antibody to p185$^{erbB-2}$ was not altered by p75, suggesting that the eluted material was not p185$^{erbB-2}$ ECD.

TABLE 2

Binding of chromatography fractions from SKBr-3 cell conditioned medium (p75) to p185$^{erbB-2}$ and EGFR.

|  | % p185$^{erbB-2}$ binding | % EGFR binding |
|---|---|---|
| Control | 100 | 100 |
| Flow-Through | 99 | 96 |
| pH 2 | 99 | 95 |
| pH 2.5 | 91 | 95 |
| pH 3 | 9 | 95 |
| pH 3.5 | 18 | 99 |
| pH 4 | 63 | 98 |

SK-Br-3 and MDA-MB-468 cells were plated (100,000 cells/well) in 24-well plates in 5% FCS IMEM (Biofluids). Binding studies were performed as described (Lupu, et al., Science 249: 1552–1555 (1990)). 50 ml of 100x conditioned media from SK-Br-3 cells were loaded into a p185$^{erbB-2}$ extracellular domain affinity chromatography column. Flow-through and fractions eluted with 1 citric acid (pH gradient from 4 to 2) were collected. After neutralization (pH 7.4) and desalting with PBS, the fractions were tested for p185$^{erbB-2}$ and EGFR binding activity. Iodinated 4D5 antibody was used to assess p185$^{erbB-2}$ binding in SK-Br-3 cells, and iodinated EGF was used to assess EGFR binding in MDA-MB-468 cells. Results are shown as percent of control (no treatment) binding. Each experiment was performed in triplicate, and the SD were less than 15% in all cases.

Since gp30 had been identified as a ligand common to both the EGFR and p185$^{erbB-2}$, we also tested the activity of all the eluted fractions from SK-Br-3 conditioned media in a EGFR binding assay using MDA-MB-468 cells and iodinated EGF. In this assay EGF and gp30, used as controls, displaced the binding of iodinated EGF in a dose dependent manner. In contrast, none of the eluted fractions derived from SK-Br-3 conditioned media showed activity, indicating that p75 does not bind to the EGFR (Table 2).

EXAMPLE 5

The TGFα-like Polypeptide (erbB-2 Ligand) Is Glycosylated

The apparent heterogeneity in size of the larger TFGα species and the potential for N-linked glycosylation of the TFGα precursor at Asn 25 led to the consideration of whether the high molecular weight TGFa-like polypeptide secreted from MDA-MB-231 cells was a glycosylated form of TGFα.

Tunicamycin Treatment

Tunicamycin (Sigma, St. Louis, Mo.) was dissolved in 50 mm sodium carbonate (pH 10.0) and falter-sterilized with a 0.22 m filter. Confluent monolayers of MDA-MB-231, MCF-7 and Hs578T cells were grown in IMEM in the presence of 20 g/ml tunicamycin (unless otherwise specified) for 4 hours prior to metabolic labelling. Metabolic labelling was then performed as described above with continued tunicamycin treatment.

When MDA-MB-231 cells were incubated with tunicamycin, an inhibitor of co-translational N-linked glycosylation, and the media was immunoprecipitated with the anti-TGFα polyclonal antibody, a species of 22 kDa replaced the previously observed 30 kDa species.

These proteins were subjected to enzymatic treatment with N-glycanase and elastase.

Elastase Treatment

The samples containing TGFα-like activity were incubated with 20 g porcine pancreatic elastase (Sigma) dissolved in 50 mM glycylglycine, pH 7.9, for 1 hour at 22° C. The samples were then subjected to immunoprecipitation and SDS-PAGE analysis.

Additional cleavage of the 22 kDa polypeptide with elastase yielded an apparent 11 kDa product, different from the mature 6 kDa TGFα that was observed in Rat-FeSrV labelled media. The 11 kDa product had a higher immunoreactivity with the R399 antibody than the 30 kDa and the 22 kDa polypeptides. Shorter exposure of the gel showed clearly a precipitated band near the 11 kDa molecular weight. Tunicamycin treatment did not significantly affect the levels of secreted TGFα activity as determined by both RIA and EGF receptor binding assays.

N-Glycanase Digestion

The purified 30 kDa TGFα-like protein was subjected to digestion with N-glycanase. Samples equivalent to 100 ng were incubated with 50 l of 0.2M sodium phosphate (pH 8.6), 1.25% NP40 and 2–6 g N-glycanase (Genzyme Corp., Boston, Mass.) were subsequently added to each sample and incubated at 37° C. for 16 hours. 50 μl of 3-fold concentrated loading buffer was added before electrophoretic analysis, performed as outlined above. The gel was silver stained.

When the purified 30 kDa polypeptide was treated with N-glycanase, a 22 kDa product was detected by silver staining. The absence of cleavage of the purified 30 kDa polypeptide after O-glycanase treatment suggests that no O-glycosylation occurs in this system.

EXAMPLE 6

Peptide Mapping

In order to determine the degree of homology between the novel 30 kDa TGFα-like growth factor and mature TGFα, peptide mapping was performed using the method of Clevand. Immunoprecipitation of metabolically labelled conditioned media from MDA-MB-231, H8, and Rat-FeSrV cells was carried out with the R399 anti-TGFα polyclonal antibody. Precipitates were analyzed on SDS-PAGE and the specific bands were electroeluted (30 kDa from MDA-MB-231 cells, 6 kDa from H8 cells, and 18 kDa from the Rat-FeSrV cells).

Electrophoretic Elution Of Radiolabelled Protein from Gels

After fluorography of an SDS-PAGE, bands of interest were excised and the protein eluted by electrophoresis into a dialysis tubing over 16 hrs at 120 volts. The contents of the dialysis bag were cooled at 4 C. and then precipitated by the addition of trichloroacetic acid to a final concentration of 20%. The precipitates were pelleted by centrifugation, washed twice with ethyl ether, and resuspended in loading buffer.

Digestion Procedure for Purified Eluted Proteins

Electroeluted proteins were dissolved at approximately 0.5 mg/ml in loading buffer which contained 0.125M Tris-HCl (pH 6.8), 0.5% SDS, 10% Glycerol and 0.001% Bromophenol Blue. The samples were then heated at 100° C. for 5 minutes. Proteolytic digestion were carried out at 37° C. for 30 minutes by the addition of Staphylococcus aureus Protease V8 (Sigma, St. Louis, Mo.) to a final concentration of 25 g/ml according to methods. β-mercaptoethanol and SDS were subsequently added to final concentrations of 20% and 2%, respectively. Proteolysis was stopped by boiling for 2 min. The samples were then injected on a C18 Reversed Phase HPLC column.

The products were then subjected to a peptide digestion using 25 g/ml V8-protease. After complete digestion, the samples were analyzed by C18 reversed phase chromatography. Three major peptide peaks eluted at different acetonitrile concentrations by reversed phase chromatography. However, the concentrations at which those peptides isolated from MDA-MB-231 cells eluted (16%, 18.7%, and 21.7% ) were different from the peptides isolated from H8 and FeSrV cells (24%, 29%, and 32.6%). The peptide elution pattern of the TGFα (6 kDa) derived from H8 cells and Rat-FeSrV cells was essential identical. The same results were obtained with 40 g of V8 protease, indicating that concentration of the enzyme was not responsible for the differential peptide cleavage.

RNA Extraction

Moreover, in vitro translation of mRNA derived from MDA-MB-231 cells and H8 cells was done. Total cellular RNA was extracted from cells by homogenizing in guanidine isothiocyanate followed by centrifugation over a cesium chloride cushion. Poly $(A)^+$mRNA was eluted in 10 mM Tris after passing total cellular RNA over an oligo (dT) cellulose column (Pharmacia, Piscataway, N.J.) equilibrated with 10 mM Tris-0.5M NaCl pH 8.0. After precipitation in ethanol (66% vol/vol) and 0.1M acetic acid, both total and poly$(A)^+$selected RNA were resuspended in 10 m Tris-1 mM EDTA buffer and separated on 1% agarose, 6% formaldehyde gels. Electrophoresis was carried out at 20 volts over 14–16 hours in: 5 mM NaAc 1 mM EDTA, 20 mM 3-[N-morpholino] propane sulfonic acid pH 7.0 (MOPS-Sigma). The gels were stained with ethidium bromide 2.0 g/ml to allow inspection of the quality and quantity of RNA ( ). In vitro translation assays were performed using Wheat Germ kit according to the manufacturer's instructions (Promega).

The resulting polypeptide had the same peptide mapping profile than the purified 30 kDa factor after treatment with N-glycanase and elastase. These results provide evidence that a precursor different than the "normal" TGFα precursor is translated from the mRNA of MDA-MB-231 cells. Moreover, the above results indicate that the MDA-MB-231 derived TGFα-like polypeptide shares very few, if any, common peptide sequences with mature TGFα.

EXAMPLE 7

Receptor Binding Activity

Figure 5A:
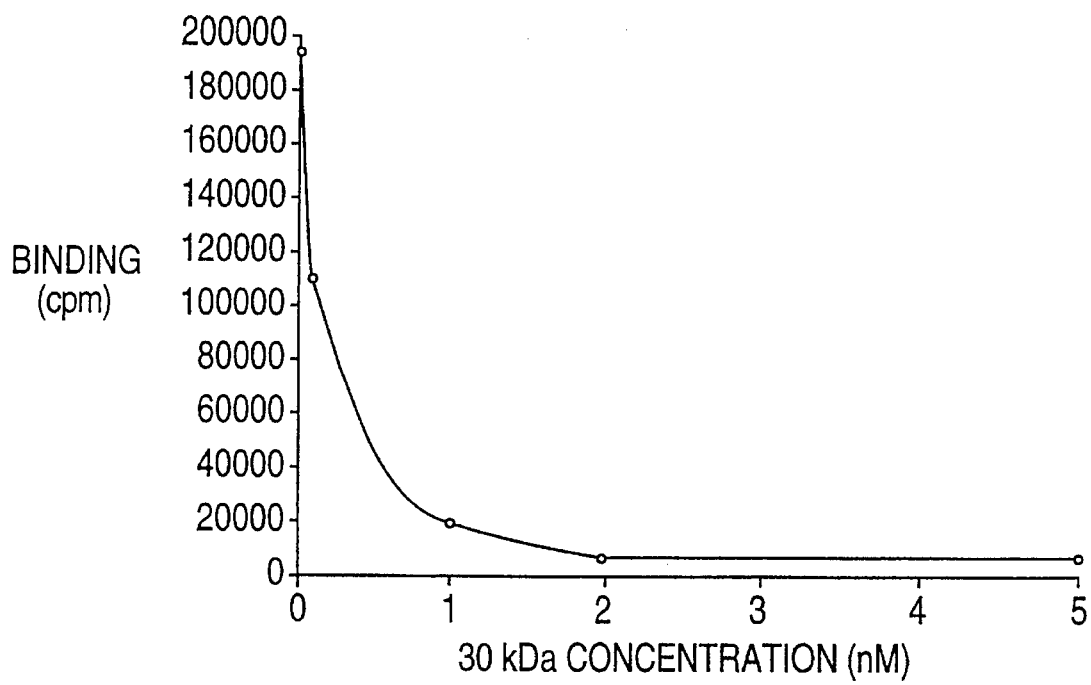
FIG. 5 illustrates a p185$^{erbB-2}$ receptor competition assay in SK-Br-3 cells.
Figure 5B:
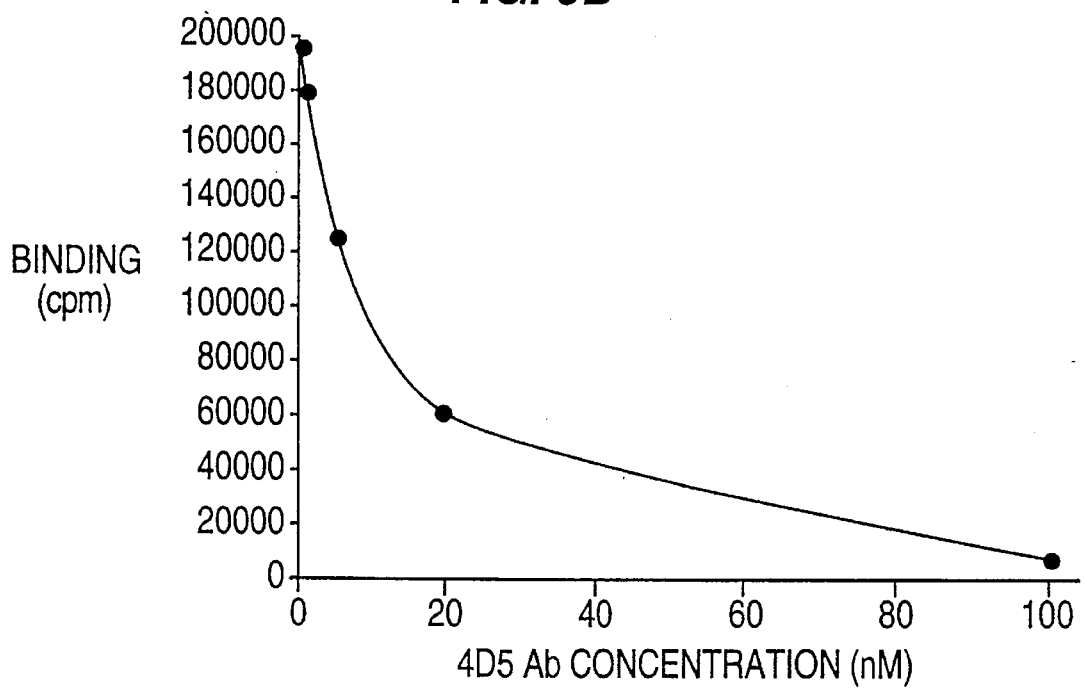

The EGF receptor binding activity of the 30 kDa TGFα-like protein was compared with that of EGF in a radioreceptor assay. Both growth factors competed with $[^{125}I]$ EGF for receptor sites on A431 membranes. The specific EGF-competing activity of the purified TGFα-like polypeptide was found to be $1-1.5\times10^6$ units/ng; 1.1 ng of TGFα-like polypeptide was required to inhibit EGF binding by 50%. TGFα-like polypeptide was as effective as EGF in EGF receptor binding.

p185$^{erbB-2}$ receptor binding was studied by competition assay in SK-Br-3 cells. SK-Br-3 cells were plated in 24 well plates in IMEM (Biofluids) supplemented with 5% FCS. After a wash with binding buffer (DMEM/F12 pH 7.4, containing 1 mg/ml BSA, 10 Mn hepes and 20 Mm glutamine) cells were incubated for 30 minutes at 37° C. with binding buffer. The EGFR were saturated with 30 nM EGF for 2 hours at 4° C. p185 binding studies were then performed for 3 hours at 4° C. with 1 nM iodinated 4D5 in the presence of various concentrations of unlabeled gp30 or 4D5. After the incubation, cells were washed 3 times with binding buffer and then solubilized with 1% SDS. The results are shown in FIG. 5. No specific binding was determined with excess (100 nM) of unlabeled antibody. Each group was assayed in triplicate. The experiments were performed five times and the results were reproducible.

EXAMPLE 8

Biological Characterization of the TGFα-like Material

In order to characterize the cellular effects of the present 30 kDa glycoprotein, various experiments were conducted. The purified 30 kDa TGFα-like polypeptide stimulated the growth of serum NRK fibroblasts and induced colony formation of these cells in soft agar using the procedure taught in Example 3.

Figure 12:
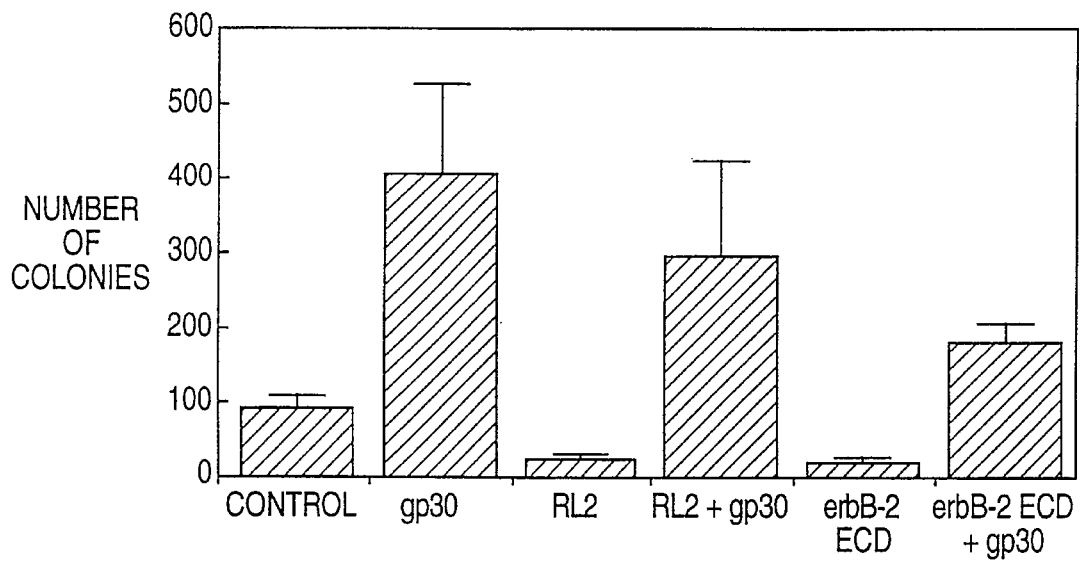
FIG. 12 illustrates the effect of gp30 on soft agar colony formation of SK-Br-3 cells.

FIG. 12 illustrates the effect of gp30 on soft agar colony formation of SK-br-3 cells.

Figure 13:
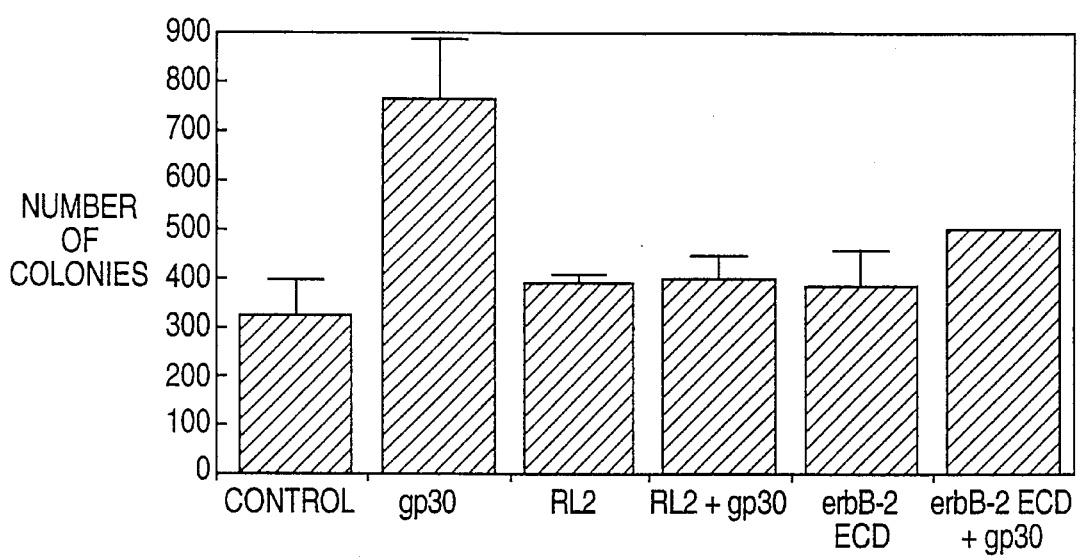
FIG. 13 illustrates the effect of gp30 on soft agar colony formation of MDA-468 cells.

FIG. 13 illustrates the effect of gp30 on soft agar colony formation of MDA-MB-468 cells.

Figure 14:
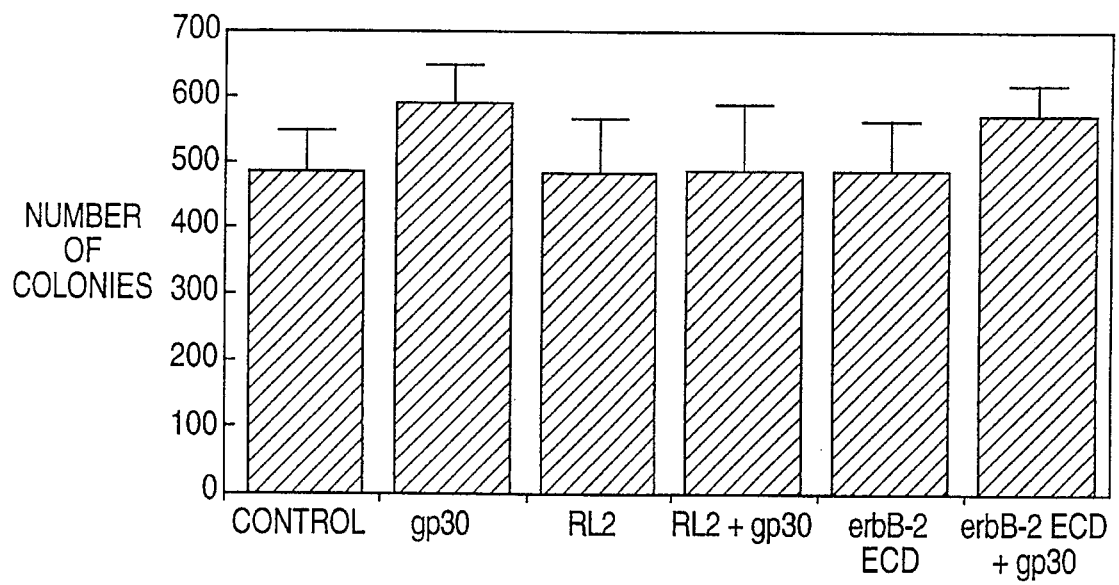
FIG. 14 illustrates the effect of gp30 on soft agar colony formation of MCF-7 cells.

FIG. 14 illustrates the effect of gp30 on soft agar colony formation of MCF-7 cells.

Figure 15:
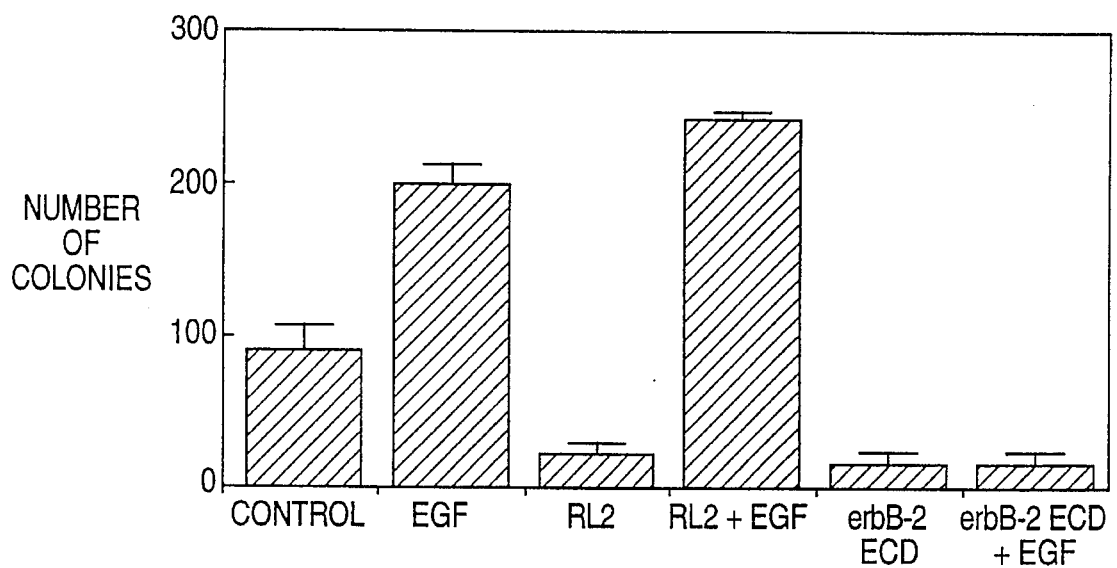
FIG. 15 illustrates the effect of EGF on soft agar colony formation of SK-Br-3 cells.

FIG. 15 illustrates the effect of EGF on soft agar colony formation of SK-br-3 cells.

Figure 16:
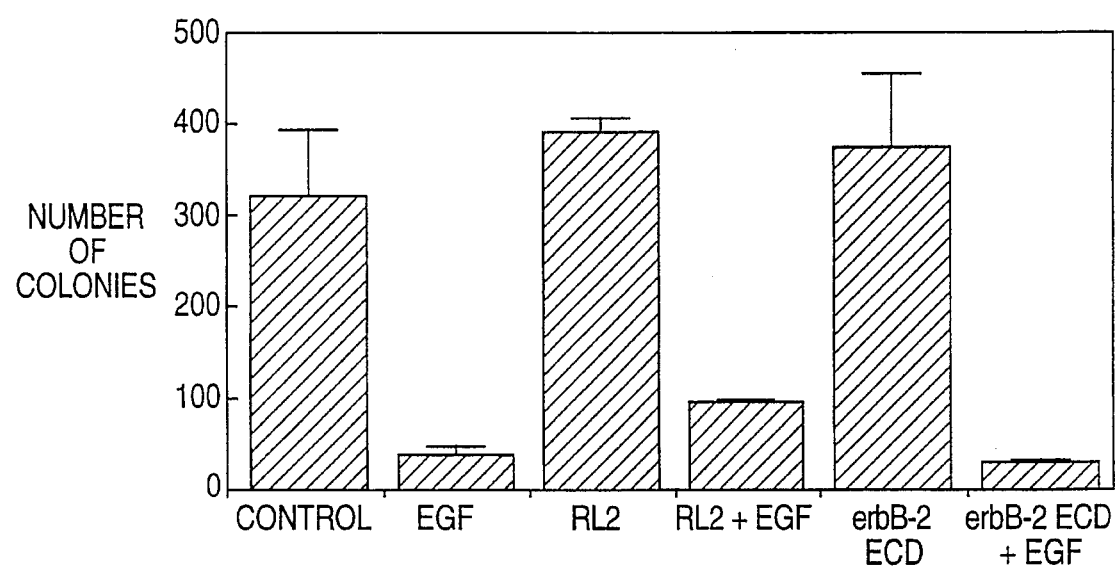
FIG. 16 illustrates the effect of EGF on soft agar colony formation of MDA-MB-468 cells.

FIG. 16 illustrates the effect of EGF on soft agar colony formation of MDA-MB-468 cells.

The bioactivity of the purified TGFα-like polypeptide was also tested by anchorage-dependent growth assays of the carcinogen-immortalized human mammary epithelial cells 184A1N4 and anchorage-independent growth assays of 184A1N4-derived cells partially transformed by SV40 T antigen, 184A1N4T.

Anchorage-Dependent Growth Assay

Cells were grown in IMEM containing 5% FCS. Upon confluence cells were detached using trypsin-versene (Biofluids, Rockville Md.) and passed at 1:20 to 1:50 dilutions. Cells were seeded in 12-well plates at 4,000–10,000 cells/well, depending on the cell type (MDA-MB-231-8,000 cells/well in serum free IMEM). After 24 hours the media was changed and the cells were treated with EGF, TGFα or TGFα-like protein were harvested at 1, 2 and 4 days using trypsin-versene. The cells were counted using a coulter counter. Dose response curves of TGFα-like polypeptide on these cells were similar to those observed with EGF and TFFα.

EXAMPLE 9

The biological activity of the purified 30 kDa TGFα-like factor was further assessed by examining its ability to induce autophosphorylation of the EGF receptor. A431 cells, which overexpress the EGF receptor, were incubated with various concentrations of EGF, TGFα or TGFα-like growth factors. Each of the three peptides similarly stimulated phosphorylation of the EGF receptor.

Phosphorylation of the EGF Receptor

Subconfluent A431 cells were cultured in IMEM for 10–12 hours. The cells were treated with 10–30 nM TGFα, EGF or TGFα-like growth factor for 30 minutes at 37° C. Cells were lysed in 20 mM Tris-HCl (pH 7.4), 150 mM NaCl, 1% NP40, 1 mM EDTA, 2 mM PMSF, 42 mM leupeptin and immunoprecipitated as described above using monoclonal antibody 225 directed against the EGF receptor (Oncogene Science, Manhasset, N.Y.). The immuno-precipitates were washed three times with RIPA buffer and resuspended in 40 l TNE (0.01M Tris-HCl, pH 7.5, 0.15M NaCl, 1 mM EDTA). Five Ci of $[\lambda-^{32}P]$ ATP was added to the immunoprecipitates and the total ATP concentration was adjusted to 15 mM (final) in a volume of 60l. The reaction mixture was incubated for 5 minutes on ice before addition of 20 1 of 3×sample buffer. The samples were boiled for 5 minutes and analyzed by denaturing 7.5% SDS-PAGE.

EXAMPLE 10

In order to characterize the cellular effects of the present 30 kDa glycoprotein ligand, its induction of tyrosine phosphorylation was assessed in the human breast cancer lines MDA-MB-468 and SK-Br-3. Notably, MDA-MB-468 cells have amplification and over expression of the EGFR gene and do not express erbB-2 receptor-like protein. SK-Br-3 cells have amplification and over expression of the erbB-2 gene as well as relatively elevated levels of EGFR.

Detection of Phosphorylated Proteins in SK-Br-3 Cells

Figure 2:
FIG. 2 illustrates the detection of phosphorylated proteins in SK-Br-3 cells.

SK-Br-3 cells were grown in 90% confluence in 24-well plates (Costar). Cells were treated at 30° C. with IMEM (FIG. 2, lanes 1 and 2), IMEM containing 25 nb/ml recombinant TGFα (Genentech, Calif.) (FIG. 2, lanes 3 and 4), and IMEM containing 5 ng/mi of gp30 (FIG. 2, lanes 5 and 6), all of these in the presence (FIG. 2, lanes 1, 4, 5) and the absence (FIG. 2, lanes 2, 3, 6) of an anti-EGF receptor blocking antibody (Genetech, Calif.). After 20 minutes the media was removed and cells were lysed in 100 μl of sample buffer containing 1% SDS, 0.1% β-mercaptoethanol, 0.15M Tris-HCl (pH6.8), 10% glycerol, 0.02% bromophenol-blue, 1 mM EDTA, 2 mM PMSF and 42 mM leupeptin. After 5 minutes at 95° C., 50 μg of protein were loaded in a 7.5% SDS-PAGE. Proteins were then transferred to nitrocellulose membrane for immunoblotting (Hoefer Scientific Instruments, California) by electrophoresis in a modified method of Towbin, et al., using an electrophoretic transfer unit (Hoefer, TE 22). Electrophoretic transfer was carried out at room temperature for one hour at 125 mA in a buffer containing 25 Mm glycine, 129 Mm Tris (Ph 8.3) and 20% methanol. Following transfer, the filter was blocked with 5% BSA in Tris-Buffered Saline containing 0.5% Tween 20. An antiphosphotryosine antibody (Amersham) was reacted with the immobilized proteins in 5% BSA (Sigma RIA Grade). Immunocomplexes were detected by a goat anti-mouse antibody conjugated to alkaline phosphatase. Blots were then incubated with a color development substrate solution containing NBT and BCIP (Promega).

Alternatively, cells were grown to 80% confluence in a 35 mm dish (Costar). FCS was removed 16 hours prior to the labelling. Cells were rinsed with [PO$_4$] free DMEM (GIBCO) and then incubated for 3 hrs at 37° C. with 1.0 mCi/ml of [$^{32}$Pi]/dish (32-orthophosphate Amersham). After 3 hrs, cells were treated for 20 minutes at 37° C. with different samples (which includes gp30). Following the incubation the culture dishes were placed over an ice-bath and the cells were washed twice with PBS. Lysates were prepared with a modified Ripa buffer, containing 1% Triton X100, kinase, protease and phosphatase inhibitors, at 4° C. The cell lysate was centrifuged at 10,000 xg for 15 minutes at 4° C. The supernatant was incubated with 10 μl of normal mouse immunoglobulin for 1 hr at 4° C., and the nonspecific complexes were clarified using protein A-sepharose (Sigma). The supernatant was incubated with a monoclonal anti-phosphotyrosine antibody IG2 (Kindly provided by Frackelton A. R.) and specifically eluted using 1 mM phenylphosphate. A second immunoprecipitation was then performed using a polyclonal antibody against the erbB-2 C-Terminal sequence or with a polyclonal antibody against the EGFR (Oncogene Science, N.Y.). The specific complexes were precipitated with 5 mg/sample protein A-sepharose (Sigma) and the pellets were washed three times with lysis buffer and the pellet was then resuspended in 50 μl sample buffer (50 mM Tris- HCl (pH 6.8), 2% SDS, 10% Glycerol, 0.1% bromophenol blue and 5% beta-mercaptoethanol). After 5 minutes at 95° C., the samples were loaded onto a 7.5% SDS-PAGE.

Phosphoaminoacid analysis

Phosphoproteins in individual bands were extracted from polyacrylaminide gels and then subjected to partial acid hydrolysis and two dimensional thin-layer electrophoresis using HTLE-7000 (CBS Scientific C.O.), using a well known procedure.

The 30 kDa ligand, TGFα and EGF were found to induce tyrosine phosphorylation in both cell lines, and EGFR blocking antibody abolished the phosphorylation induced by the three growth factors in MDA-MB-468 cells. This antibody did not, however, completely block the phosphorylation induced by the present 30 kDa ligand in SK-Br-3 cells. However, it did block the phosphorylation induced by TGFα.

From the above result, it appears that tyrosine phosphorylation of a protein is different from EGFR occurs in SK-Br-3 cells treated with 30 kDa factor. No phosphorylation was observed in untreated SK-Br-3 cells, and cells treated with the anti-EGFR antibody alone.

EXAMPLE 11

Detection of Phosphorylated Proteins in MDA-MB-453 Cells

Figure 3:
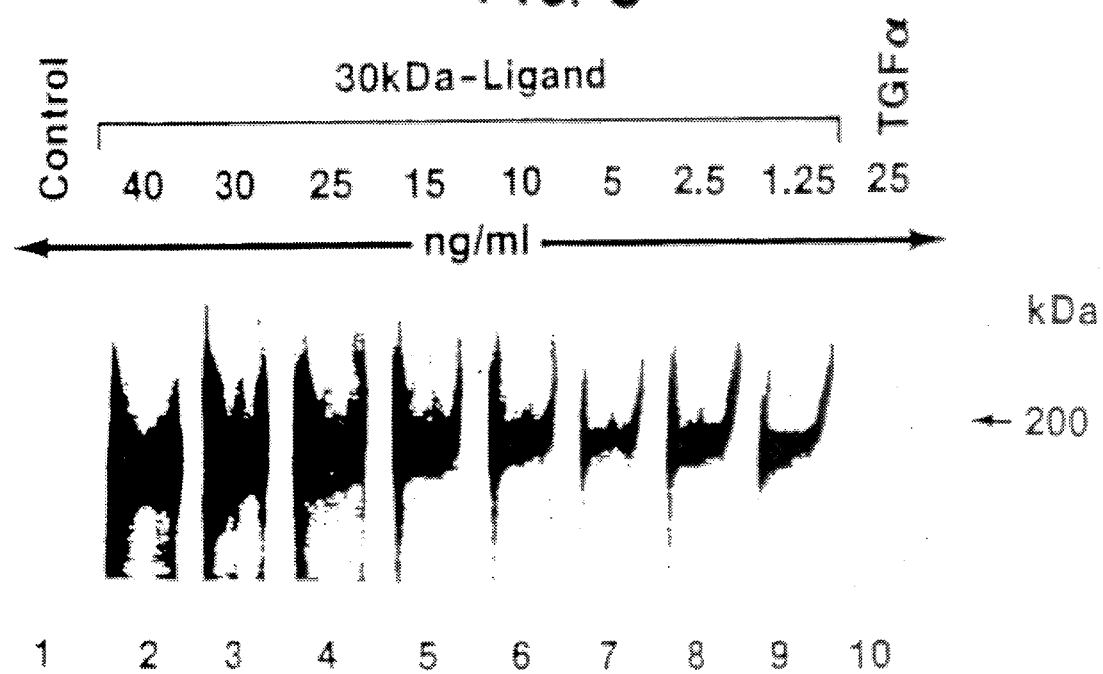
FIG. 3 illustrates the detection of phosphorylated proteins in MDA-MB-453 cells.

MDA-MB-453 cells were grown to 90% confluence in 24-well plates (Costar) and treated at 37° C. with IMEM (FIG. 3, lane 1), IMEM containing 25 ng/ml of recombinant TGFα (Genetech, Calif.) (FIG. 3, lane 10), or IMEM containing 1.25–40 ng/ml of gp30 (FIG. 3, lanes 2–9). After 20 minutes media was removed and cells were lysed in 100 μ1 of sample buffer as described in Example 10. After 5 minutes at 95° C., 50 μg of protein was loaded in a 7.5% SDS-PAGE. Proteins were then transferred to nitrocellulose membrane for immunoblotting with an antiphosphotryosine antibody (Amersham) as described in Example 10.

In human mammary carcinoma cell line MDA-MB-453, which over expresses erbB-2, but which has undetectable levels of the EGF receptor protein or mRNA, the 30 kDa ligand was observed to induce a significant increase in tyrosine phosphorylation in a dose dependent manner at concentrations ranging from 1.25 mg/ml to 50 mg/ml. By contrast, EGF and TGFα were unable to induce tyrosine phosphorylation in the 185 kDa range, at a concentration of 25 mg/ml. No phosphorylation was observed in untreated cells. Hence, from the above, a direct interaction between the 30 kDa ligand and the 185 kDa glycoprotein appears to occur.

EXAMPLE 12

Phosphorylation of p185 Protein in Intact CHO/DHFR and CHO/erbB-2 Cells

Figure 4:
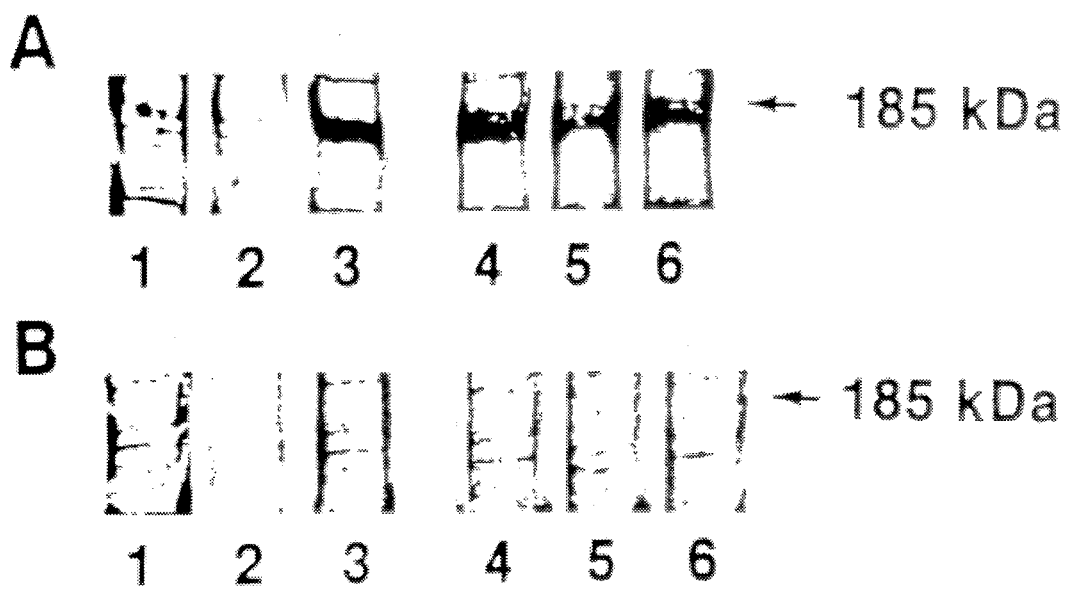
FIG. 4 illustrates the phosphorylation of p185$^{erbB-2}$ protein in intact CHO/DHFR and CHO/erbB-2 cells.

Cells were grown to 90% confluence in 24-2311 plates (Costar) in αMEM (Biofluids) supplemented with 10% dialyzed FCS, 0.75 mg/ml G418, and Methotrexate (MTX) at concentrations of 50 nM (CHO parental and CHO-DHFR) or 250 nM (CHO-erbB-2). CHO-DHFR (FIG. 4A) and CHO-erbB-2 (FIG. 4B) cells, were treated at 37° C. with control media supplemented with 20 Mm Hepes (pH 7.4) (FIGS. 4A and B, lanes 1 and 4), with 10 ng/ml of recombinant TGFα (Genetech, Calif.) (FIGS. 4A and B, lanes 2 and 5), and control media supplemented 2.0 ng/ml of gp30 (FIGS. 4A and B, lanes 3 and 6). After 20 minutes, media was removed and cells were lysed in 100 µl of sample buffer (as described in Example 10). An anti-phosphotyrosine antibody (FIGS. 4A and B, lanes 1 to 3) (Amersham) and an anti-erbB-2 antibody (FIGS. 4A and B, lanes 4 to 6) (NEN), were reacted with the immobilized proteins in 5% BSA (Sigma RIA Grade). Immunocomplexes were detected as described for Example 10.

EXAMPLE 13

Inhibition of P185 Cross-linking With 4D5 Antibody of gp30

Figure 6:
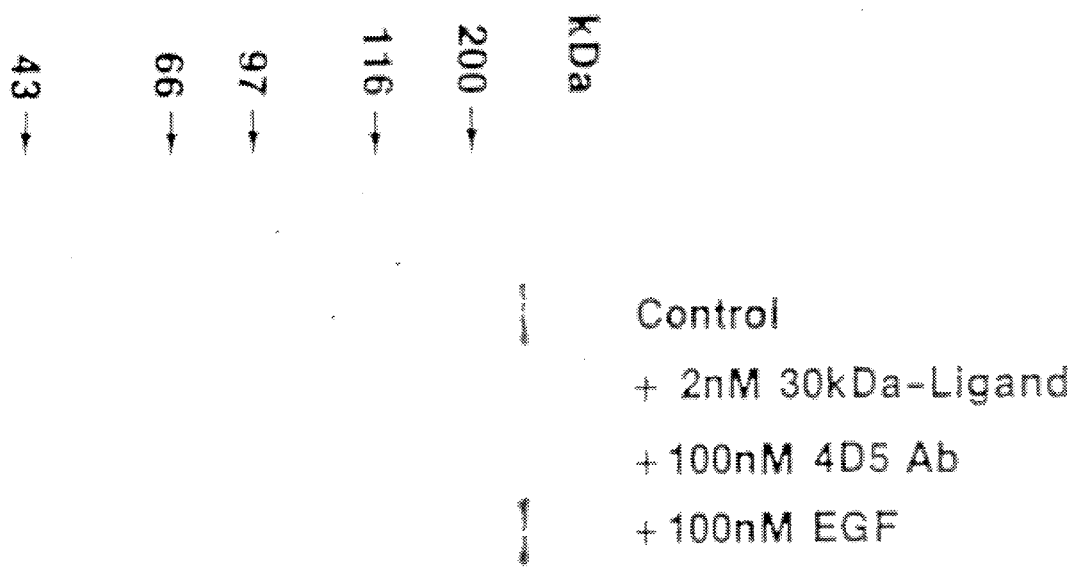
FIG. 6 illustrates the inhibition of p185$^{erbB-2}$ cross-linking with 4D5 antibody by gp30.

The binding assays were performed as described in Example 5. Binding was performed with iodinated 4D5 (1 nm) alone (FIG. 6, lane 1), in the presence of 100 nM unlabeled 4D5 (FIG. 6 lane 2) and in the presence of 2 nM gp30 (FIG. 6, lane 3). 100 nM EGF were used as a control (FIG. 6, lane 4). Cells were then treated with a cross-linking agent EGS for 45 minutes at 4° C., then quenched by adding 0.1 ml of 20 mM $NH_4Cl$. The solubilized cells were immunoprecipitated with a polyclonal antibody to the C-terminal domain of erbB-2 (Genetech, Calif.). The precipitates were analyzed on a 5% SDS-PAGE.

EXAMPLE 14

In order to determine the effects of the present 30 kDa ligand on the proliferation in colony formation of breast carcinoma cell lines, the following experiment was conducted.

Cells were treated with the present 30 kDa growth factor, EGF, TGFα and anti-erbB-2 antibody in order to inhibit the proliferation of SK-Br-3 cells.

It was observed that the anti-erbB-2 antibody inhibited the proliferation of the SK-Br-3 and MDA-MB-453 cells by 60–70% but did not inhibit the proliferation of MDA-MB-468 cells. Surprisingly, by exposing SK-Br-3, MDA-MB-453 MB-453 and MDA-MB-468 cells to the 30 kDa ligand protein of the present invention, a 60–70% inhibition of cell growth was observed for all cell lines.

Inhibition of growth by the 30 kDa ligand protein was reversed by an EGFR blocking antibody in MDA-MB-468 cells, but not in SK-Br-3 or MDA-MB-453 cells. This is an indication that the effects of the 30 kDa protein on SK-Br-3 and MDA-MB-453 cells are not mediated through EGFR.

By contrast, the present 30 kDa glycoprotein exhibited no effect on MCF-7 cells, which have normal levels of EGFR and erbB-2. Additionally, EGF and TGFα inhibited the anchorage dependant growth of MDA-MB-468 cells and SK-Br-3 cells, but not that of MDA-MB-453 or MCF-7 cells. EGF-induced anchorage dependant growth inhibition of SK-Br-3 and MDA-MB-468 cells was reversed by an anti-EGFR blocking antibody. In the presence of the 30 kDa glycoprotein, the growth inhibition of SK-Br-3, MDA-MB-453 and MDA-MB-468 cells was nearly complete.

The growth inhibitory property of the present 30 kDa ligand appears to be similar to that described for EGF on cells which express EGFR such as A431 cells and MDA-MB-468 cells.

EXAMPLE 15

Further, the growth of CHO/erbB-2 transfected cells was inhibited by 70–80% after treatment with the present 30 kDa glycoprotein. No effect was observed on the CHO/DHFR control transfectants and the parenteral CHO line. TGFα at the same molar concentration did not exhibit any effect on the proliferation of any of the three lines. Tyrosine phosphorylation and cell proliferation of the CHO/DHFR cells and the parenteral CHO cell line is not effected after treatments by the present 30 kDa ligand or TGFα.

EXAMPLE 16

Cell Growth Inhibition by gp30

Sk-Br-3, MDA-MB-453, MDA-MB-468 and MCF-7 cells were plated in 24 well plates in IMEM (Biofluids) supplemented with 5% FCS. Parental CHO cells, and CHO cells transfected with the DHFR gene or the erbB-2 gene were plated in 24 well plates (Costar) in α-MEM (Biofluids) supplemented by 10% dialyzed FCS, 0.75 mg/ml G418 and Methotrexate (MTX) 50 nM for the CHO parental and CHO-DHFR CELLS for 250 nm for the CHO-erbB-2. After 24 hours media was removed and replaced with control serum free media (SFM) containing fibronectin, transferrin, hepes, glutamine, trace elements, and BSA, or SFM with the addition of 2.0 ng/ml gp30, 10 ng/ml recombinant TGFα (Genetech), or with 2.5 µg/ml 4D5 specific anti-p185$^{erbB-2}$ monoclonal antibody. Cells were grown in 90% confluence of control and counted. Each group was assayed in triplicate. The results are shown below in Table 3 as growth relative to control. The experiments were performed three times and the results were reproducible.

TABLE 3

|  | SK-BR-3 | MDA-MB-453 | CHO/erbB-2 | CHO/DHFR | MDA-MB-468 | MCF-7 |
| --- | --- | --- | --- | --- | --- | --- |
| gp30 | 31 | 24 | 20 | 99 | 18 | 100 |
| 4D5 antibody | 32 | 34 | 22 | 98 | 104 | 92 |
| TGFα | 73 | 91 | 89 | 95 | 79 | 105 |
| Control antibody | 87 | 91 | 87 | 94 | 92 | 99 |

EXAMPLE 17

Figure 8A:
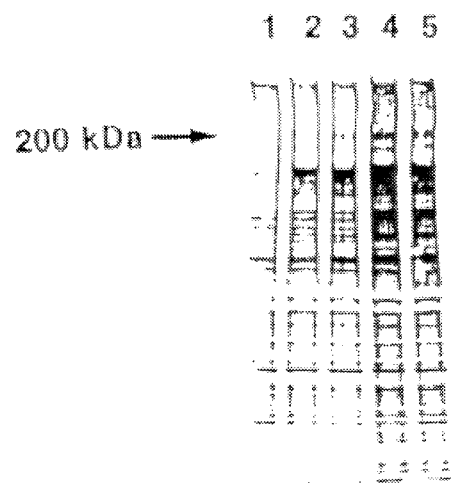
FIGS. 8A–C show detection of phosphorylated proteins from cells incubated in the presence of gp30 or p75. Control media did not contain these ligand molecules.

Since p75 interacted with the erbB-2 oncogene product, we next explored whether p75 activated p185$^{erbB-2}$. We studied the ability of p75 to phosphorylate p185$^{erbB-2}$ using MDA-MB-453 human breast cancer cells, which overexpress the erbB-2 oncoprotein but do not express detectable levels of EGFR. First we determined that p75 activated tyrosine phosphorylation in MDA-MB-453 cells, using an anitphosphotyrosine monoclonal antibody in a Western blot analysis Towbin, et al., *Proc. Natl. Acad. Sci. USA*, 76:4350 (1979)) (FIG. 8A).

MDA-MB-453 cells were growth to 90% confluence in 24-well plate (Costar). Cells were treated for 20 minutes at 37° C. with control media containing 20 mM Hepes, pH 7.4 (lane 1), control media containing 5 ng/ml of gp30 (lanes 2), control media containing 4 ng/ml p75 (lane 3), control media containing 8 ng/ml p75 (lane 4), and control media containing 2 ng/ml p75 (lane 5). The media was removed and cells were lysed in 100 µl of sample buffer containing 1% SDS, 0.1% β-mercaptoethanol, 0.15 M Tris-HCl (pH 6.8), 10% glycerol, 20.0% bromophenol-blue, 1 mM EDTA, 2 mM phenylmethyl sulphonyl fluoride (PMSF) and 24 mM leupeptin. After 5 minutes at 95° C., 50 µg of protein were loaded in a 7.5% SDS-PAGE. Proteins were then transferred to a nitrocellulose membrane for immunoblotting (Heofer Scientific Instruments, California) by electrophoresis in a modified method of Towbin, et al., *PNAS,* 76:4350 (1987), using a Hoeffer electrophoretic transfer unit (Hoeffer, Model number TE 22). Electrophoretic transfer was carried out at room temperature for one hour in a buffer containing 25 mM glycine, 129 mM Tris (pH 8.3) and 20% methanol. Following transfer, the filter was blocked with 5% BSA in Tris-Buffered Saline containing 0.5% Tween 20. An antiphosphotyrosine antibody (Amersham) reacted with the immobilized proteins in 5% BSA (Sigma RIA Grade). Immune-complexes were detected by a goat anti-mouse antibody conjugated to alkaline phosphatase. The blots were then incubated with a color development substrate solution containing NBT and BCIP (Promega).

Figure 8B:
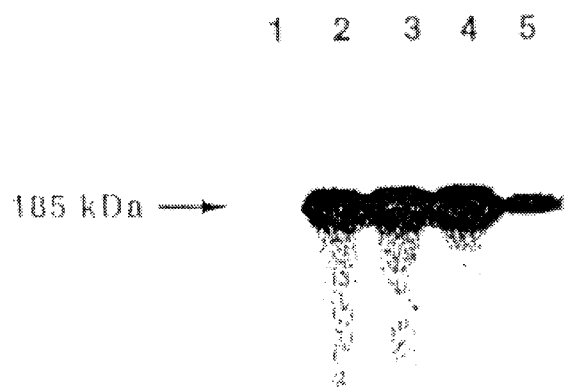

The specificity of the tyrosine phosphorylation for $p185^{erbB-2}$ was confirmed by labeling MDA-MB-453 cells with [$^{32}$P] and immunoprecipitating the $p185^{erbB-2}$ oncoprotein with a polyclonal antibody that reacts with the C-terminal domain of $p185^{erbB-2}$ but does not show cross-reactivity with EGFR (Hudziak, et al., *Proc. Natl. Acad. Sci. USA,* 84:7159 (1987)) (FIG. 8B). MDA-MB-453 cells were growth to 80% confluence in 24-well plates (Costar). The cells were washed then twice with $PO_4$ free culture media [$PO_4$] free MEM (GIBCO), with 10% $PO_4$ free dialyzed fetal calf serum (FCS) and 2 mM glutamine. The cells were then grown in 3 ml/well of $PO_4$ free culture media for 24 hrs., subsequently the column of medium was adjusted to 1.0 ml/well and 0.5 mCi of [$^{32}$Pi]/well was added and the cells were incubated for 6 hrs.

Cells were treated for 20 minutes at 37° C. with control media (lanes 1), control media containing 2.0 ng/ml of gp30 (lanes 2), control media containing 4.0 ng/ml p75 (lane 3), control media containing 8.0 ng/ml p75 (lane 4), and control media containing 2.0 ng/ml p75 (lane 5). Following the incubation, the culture dishes were placed over ice-bath and the cells were washed twice with PBS at 4 ° C. for 10 minutes with 200 µl/well lysis buffer (50 mM Hepes, 150 mM NaCl, 1.0% Triton x-100, 1 mM EGTA, 5 mM EDTA, 10% glycerol, 0.2 mM sodium orthovanadate, 0.5 mM PMSF, 20 µg/ml leupeptin, and 5 mM ATP, final pH 7.5). The cell lysate was centrifuged at 10,000 g for 1 minute at 4° C. The supernatant was incubated with 10 µl of normal rabbit serum (NRS) for 1 hr at 4° C. and the non specific complexes were clarified using protein A-sepharose (Sigma). The supernatant was incubated with a polyclonal antibody against the erbB-2 C-terminal sequence (Hudziak, et al., *Proc. Natl. Acad. Sci. USA,* 84:7159, 1987). The specific complexes were precipitated with protein A-sepharose (Sigma) and the pellets were washed three times with lysis buffer and the pellet was then resuspended in 50 µl sample buffer (50 mM Tris- HCl (pH 6.8), 2% SDS, 10% glycerol, 0.1% bromophenol blue and 5% betamercaptoethanol). After 5 minutes at 95° C., the samples were loaded in a 7.5% SDS-PAGE. No phosphorylation was observed when MDA-MB-453 cells were treated with EGF.

In control experiments, phosphorylated EGFR was precipitated from MDA-MB-468 cells with an anti-EGFR antibody after treatment with gp30, EGF and TGFα. MDA-MB-468 cells were grown to 80% confluence in 24-well plate (Costar). The cells were washed twice with $PO_4$ free culture media [$PO_4$] free MEM (GIBCO), with 10% $PO_4$ free dialyzed fetal calf serum (FCS) and 2 mM glutamine. The cells were then grown in 3 ml/well of $PO_4$ free culture media for 24 hrs. Subsequently the volume of medium was adjusted to 1.0 ml/well and 0.5 mCi of [$^{32}$Pi ]/well was added and the cells were incubated for 6 hrs.

Figure 8C:
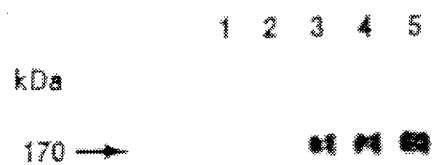

Cells were treated for 20 minutes at 37° C. with control media (FIG. 8C, lane 2), control media containing 10.0 ng/ml of p75 (FIG. 8C, lane 1), control media containing 4.0 ng/ml TGFα (FIG. 8C, lane 3), control media containing 4.0 ng/ml EGF (FIG. 8C, lane 4), and control media containing 2.0 ng/ml gp30 (FIG. 8C, lane 5). Following the incubation the culture dishes were placed over an ice-bath and the cells were washed twice with PBS at 4° C. Then, cells were lysed at 4° C. for 10 minutes with 200 µl/well lysis buffer (50 mM Hepes, 150 mM NaCl, 1.0% Triton X-100, 1 mM EGTA, 5 mM EDTA, 10% glycerol, 0.2 mM sodium orthovanadate, 0.5 mM PMSF, 20 µg/ml leupeptin, and 5 mM ATP, final pH 7.5). The cell lysate was centrifuged at 10,000 g for 1 minute at 4° C.

The supernatant was incubated with 10 µm of normal rabbit serum (NRS) for 1 hr at 4° C. and the non specific complexes were clarified using protein A-sepharose (Sigma). The supernatant was incubated with a polyclonal antibody against the EGFR (Oncogene Science, N.Y.). The specific complexes were precipitated with protein A-sepharose (Sigma) and the pellets were washed three times with lysis buffer and the pellet was then resuspended in 50 µl sample buffer (50 mM Tris-HCl (pH 6.8), 2% SDS, 10% Glycerol, 0.1% bromophenol blue and 5% beta-mercaptoethanol). After 5 minutes at 95° C., the samples were loaded in a 7.5% SDS-PAGE.

p75 did not induce phosphorylation of the EGFR in these cells (FIG. 8C). These observations supported the hypothesis of an exclusive interaction between p75 and its receptor $p185^{erbB-2}$.

EXAMPLE 18

Cellular Response to erbB-2 Ligand

Figure 9:
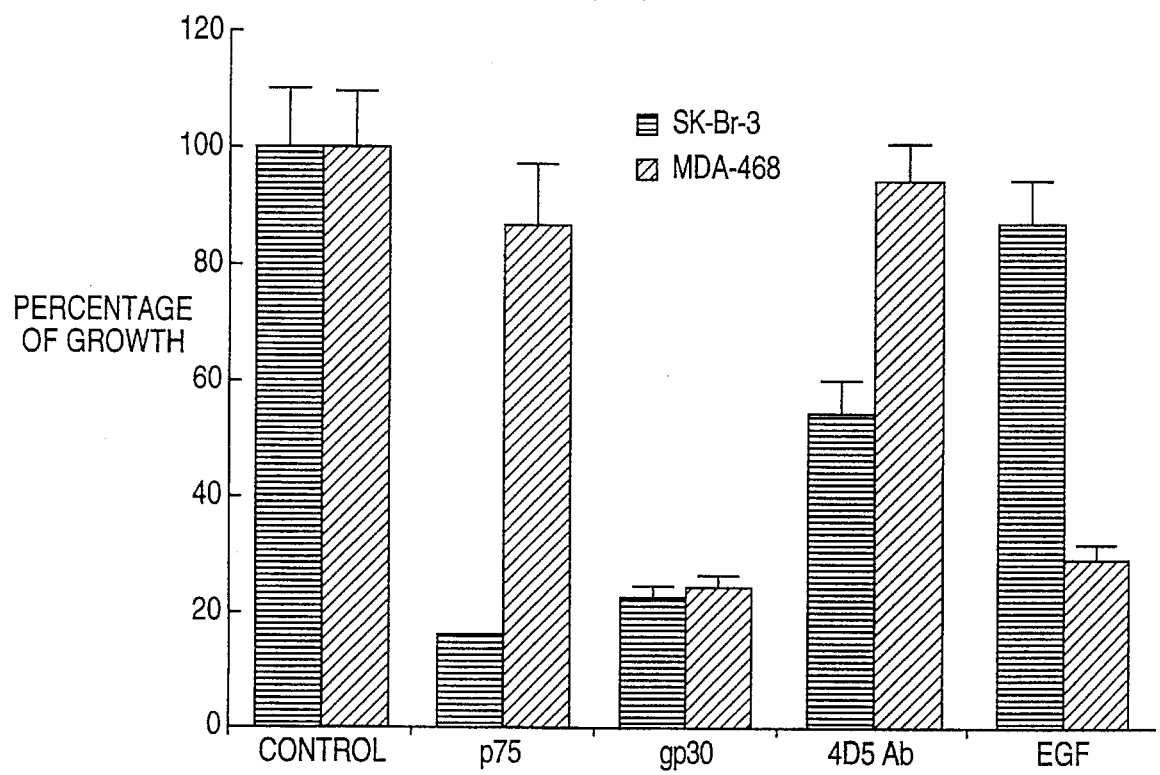
FIG. 9 depicts the effect of p75 on the growth of human breast cancer cells.

We examined the biological effects of p75 in breast cancer cells, using anchorage-dependent and anchorage-independent growth assays. SK-Br-3 and MDA-MB-468 cells were plated (30,000 cells/well) in 24 well plates in IMEM (Biofluids) supplemented with 5% FCS. After 24 hrs the media was removed and replaced with control serum free media containing fibronectin, transferrin, hepes, glutamine, trace elements, and BSA (SFM+), or SFM+ with the addition of purified p75 (4 ng/ml), purified gp30 (2.0 ng/ml) or with EGF (10 ng/ml). Cells were grown to 90% confluence of control and counted. Each group was assayed in triplicate. Results are shown as growth relative to control. The experiments were performed three times and the results were reproducible.

p75 inhibited the cellular proliferation of the overexpressing cells SK-Br-3, BT-474 and MDA-MB-453 by 70–80% at a concentration of 4 ng/ml (The concentration of p75 polypeptide was determined by 4D5 binding assay). No inhibition was observed in MDA-MB-468 cells, which overexpress the EGFR, or in MCF-7 cells which do not overexpress $p185^{erbB-2}$ or EGFR. gp30, used as control, inhibited the proliferation of SK-Br-3 and MDA-MB-468 cells (FIG. 9). In an anchorage-independent growth assay, p75 inhibited the soft agar colony formation of SK-Br-3 and MDA-MB-453 cells by 60–70%.

Since our initial experiments p75 inhibited the growth of breast cancer cells, we speculated that either p75 was an inhibitory ligand or the inhibitory function of p75 resulted from hyperstimulation of the erbB-2 receptor. SK-BR-3 cells were plated in 35 mm tissue culture dishes (Costar, Cambridge, Mass.). A bottom layer of 1.0 ml IMEM (Biofluids) containing 0.6% agar and 10% fetal calf serum (FCS) was prepared. After the bottom layer was solidified, 10,000 cells per dish were added in a 0.8 ml top layer containing the cells, 0.4% Bacto agar (Difco, Detroit, Mich.) with 10% FCS alone and with increasing concentrations of p75 (0–132 pM), and gp30 (0–330 pM). All samples were run in triplicate and experiments were carried out in FCS that had been tested for optimal cloning efficiency. Cells were incubated 7–9 days at 37° C. in 5% $CO_2$. Colonies larger than 60 µm were counted in a colony counter. The experiments were performed three times and the results were reproducible.

Figure 10:
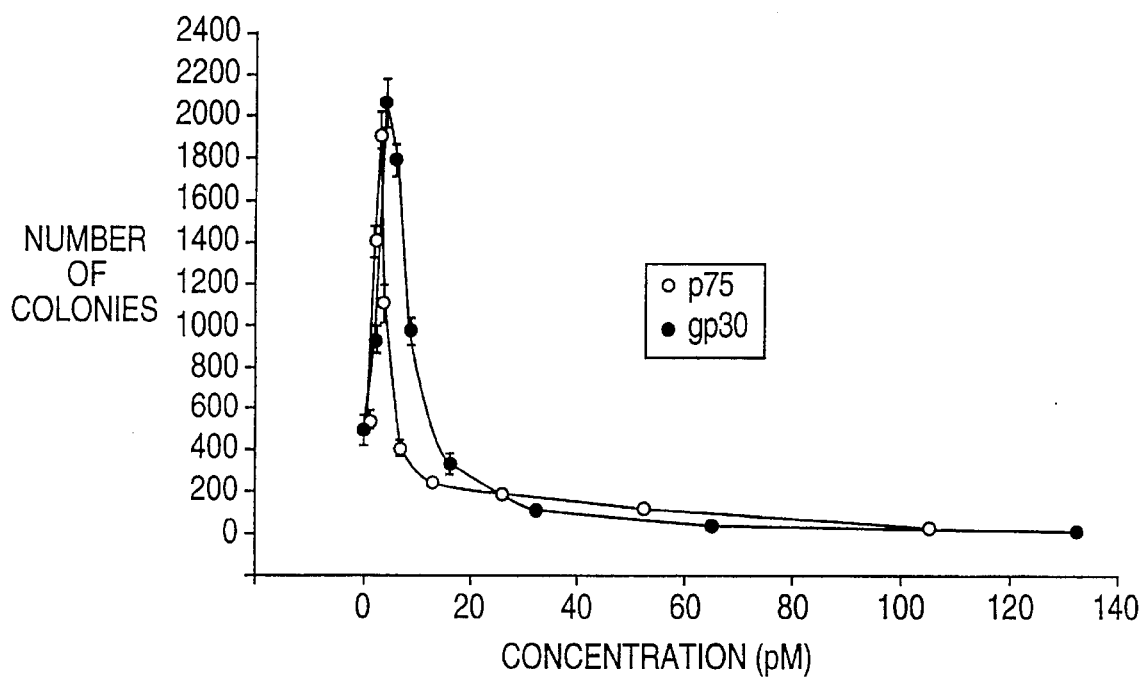
FIG. 10 shows the effect of p75 on the soft agar colony formation of human breast cancer cells.

We observed that p75 at very low doses (3.3 pM, 0.25 ng/ml) had a stimulatory growth effect on SK-Br-3 (FIG. 10). The proliferative effects of gp30 at equimolar concentrations were similar to those of p75 (FIG. 10). As an additional control, EGF at concentrations from 1–100 nM had no significant effects on the growth of SK-Br-3 cells. The results obtained with p75 argued against the possibility of an inhibitory ligand. Dose-related paradoxical effects of growth factors on cellular proliferation have been reported in the literature.

Low concentrations of gp30 stimulated the growth of SK-Br-3 cells, while high concentrations were growth inhibitory (Lupu, et al., Science, 249:1552 (1990)). EGFR-overexpressing breast cancer cells MDA-MB-468, as well as the A431 cancer cells, are growth-inhibited by high doses of EGF but are stimulated by very low doses of EGF (Kawamoto, et al., J. Biol, Chem., 249:7761 (1984); Ennis, et al., Molec. Endocr., 3:1830 (1989)). It has also been reported that cells overexpressing the estrogen receptor are growth-inhibited by physiological doses of estrogen (Kushner, et al., Molec. Endocr., 4:1465 (1990)).

EXAMPLE 19

Interaction of p75 with p185$^{erbB-2}$ Extracellular Domain

In additional experiments, we explored the interaction of p75 and p185$^{erbB-2}$ soluble extracellular domain. SK-Br-3 cells were plated in 35 mm tissue culture dishes (Costar, Cambridge, Mass.). A bottom layer of 1.0 ml IMEM (Biofluids) containing 0.6% agar and 10% FCS was prepared after the bottom layer was solidified. The indicator cell, 10,000 cells per dish were added in a 0.8 ml top layer containing the sample, 0.4% Bacto agar (Difco, Detroit, Mich.) and 10% FCS. The samples were p75 (0.15 ng/ml), soluble recombinant ECD (12 µg/ml) and p75 in the presence of EDC. All samples were run in triplicates and experiments were carried out in FCS that had been tested for optimal cloning efficiency. Cells were incubated 7–9 days at 37° C. in 5% $CO_2$. Colonies larger than 60 µm were counted in a colony counter. The experiments were performed three times and the results were reproducible.

Figure 11:
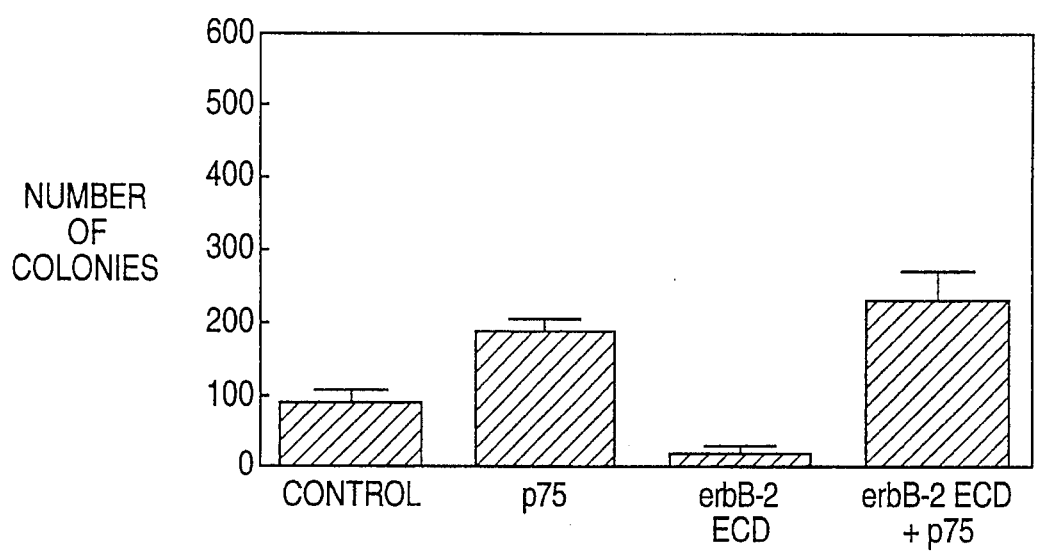
FIG. 11 shows the effect of soluble p185$^{erbB-2}$ extracellular domain on the soft agar colony formation of human breast cancer cells.

As might have been expected, addition of soluble p185$^{erbB-2}$ ECD to SK-Br-3 cells inhibited their soft agar colony formation. The inhibitory effect of this ECD may be due either to dimerization of the soluble domain with the cellular p185$^{erbB-2}$ receptor, or to binding and neutralization of p75, which is essential for their growth, therefore leading to inhibition of cell proliferation. ECD inhibited colony formation exclusively in those cells overexpressing p185$^{erbB-2}$ (FIG. 11). No inhibition was observed in MDA-MB-468 and MCF-7 cells. In order to understand the mechanism by which erbB-2 ECD inhibited colony formation of SK-Br-3 cells, growth-stimulatory doses of p75 were added to ECD-treated cells. The inhibitory effect of the ECD was reversed by the addition of stimulating doses of p75, suggesting that complex regulatory pathways may exist for p185$^{erbB-2}$ (FIG. 11).

EXAMPLE 20

Large scale purification and partial amino acid Sequence of gp30

The following scheme of purification defines a preferred sequence of steps for gp30 recovery in different systems.

Heparin affinity Chromatography: Media conditioned by MDA-MB-231 or SKBr-3 cells are clarified by centrifugation for 20 minutes at 2,000 rpm at 4° C. The supernatant is collected and stored at −70° C. After allowing heparin-sepharose beads to expand in PBS, 2 ml of gel beads are loaded on an Econo column and washed with about 100 bed volumes of PBS. Conditioned media are run through the beads by gravity (flow rate 20 to 50 ml/hr). Gradient steps of 0.4M-2.0M NaCl are used until the 280 nm absorption during each step returns to baseline. Purification of 200 liters of conditioned media was performed, and sufficient material was obtained to perform a partial tryptic digestion.

Extraction of polypeptides from SDS-PAGE: After obtaining approximately 5 µg of purified protein (gp30), extraction with acetonitrile was performed. After the extraction, amino acid analysis was determined to evaluate the amounts of protein in the sample. The purified material was subjected to conventional N-terminal sequencing. After several trials it was concluded that gp30 was N-terminally blocked.

Figure 17A:
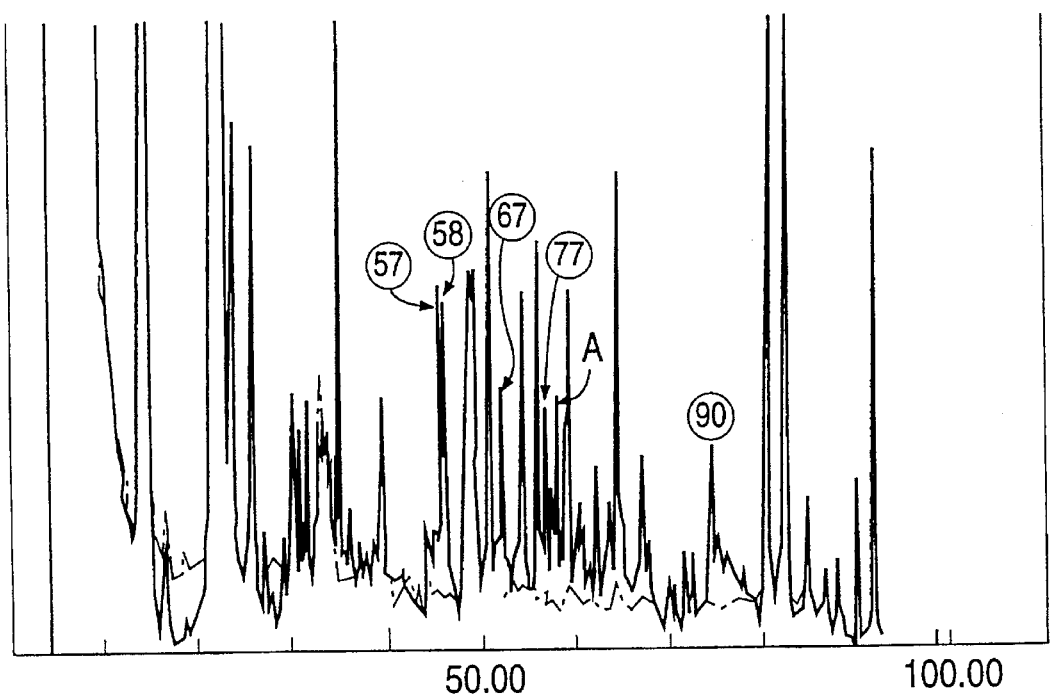
Figures 17B, 18C:

Further amino acid sequencing was done by treating gp30 with trypsin (partial tryptic digestion). After the digestion, peptides were separated on HPLC on a C18-Reversed-phase column, single peptides were collected as shown in FIG. 17A, and several peaks were subjected to protein sequence analysis. Five independent fragments were sequenced as shown in FIG. 17B.

EXAMPLE 21

Isolation of a cDNA clone that encodes gp30

In order to allow identification of gp30-specific cDNA clones by nucleic acid hybridization, several oligonucleotides were designed based on the amino acid composition of the tryptic peptides. All the possible codons were used in designing the shorter probe (16–48 combinations). End-labeled synthetic oligonucleotides were used to screen a cDNA library that was prepared with mRNA isolated from MDA-MB-231 cells by standard procedures. cDNA was synthesized with the superscript kit (Stratagene). Column-fractionated double stranded cDNA was ligated into an EcoRI site in a phage vector. Approximately three hundred thousand plaques were plated at a density of 30,000 plaques per 150 mm petri dish. The screening procedure used Y1090 (r$^-$) as the host bacteria. Areas containing plaques that resulted in positive hybridization were selected and placed into a lambda diluent (10 mM Tri-pH:7.5, 10 mM $MgCl_2$). The phage lysate was used to reinfect Y1090 (r$^-$) cells which were then replated at densities that allowed subsequent isolation of a single positive plaque and the detection procedure was repeated. To analyze the positive clones, a phage DNA preparation was performed using a mini preparation technique followed by a digestion with EcoRI restriction enzyme, to get an estimate of the size of the cDNA insert. Initial sequencing reactions were performed using miniprep phage DNA with lambda-zap forward and reverse primers (New England Biolabs).

Sixteen cDNA clones, which independently hybridized with both probes, were detected. After four screenings, 9 clones remained positive. To facilitate subsequent sequencing and further expression analysis, the complete cDNA inserts were amplified using the Polymerase Chain Reaction (PCR) technique with lambda-zap forward and reverse primers. The PCR amplified material was then subcloned into the EcoRI site of the TA-cloning vector (Invitrogen) and were sequenced using oligonucleotides complementary to the SP6 and T7 promotor binding sites as primers. We obtained several positive clones. After extensive sequencing analysis and deduced amino acid sequence we determined the full length cDNA of gp30 as shown in FIG. 18A. The sequence was computer-analyzed for the presence of an eukaryotic secretory signal and the presence of the initiation codons that confirm the Kozak consensus.

In addition to the full length cDNA clone shown in FIG. 18A that encodes gp30 ($\alpha$1), three other cDNA's were obtained from the same expression library. These clones appear to be highly homologous to the cDNA sequence of gp30 ($\alpha$1) but probably are alternatively spliced molecules. The size of these molecules are different from each other: $\alpha$1:2165 oligonucleotides, $\beta$2:1861 oligonucleotides, $\beta$3:2260 oligonucleotides and $\beta$4:1681 oligonucleotides. The sequence of one of these clones (gp30/$\beta$1) is shown in FIG. 18B.

RNAse protection assay:

gp30 expression may be detected by RNAse protection assays, for which we have generated several riboprobes (to the different forms of the original gp30 cDNA). These riboprobes generate a different protected size that correlates with the gp30 cDNA, or its alternative spliced molecules. Total RNA is hybridized with 120,000 cpm of labeled probe for 12–16 hours at 50° C. Samples are then digested with 40 µg/ml of RNAse A and 2 µg/ml of RNAse T1 for 30 min at 28° C. The RNAse digestion is terminated by the addition of both proteinase K 1 µg/ml and 1% SDS. Following one extraction with phenol/chloroform/isoamylalcohol (25:24:1), the samples are precipitated with 2 µg tRNA in absolute ethanol. Pellets are boiled in loading buffer, and the sample is electrophoretically fractionated in 6% polyacrylamide gels containing 8M urea. The gels are dried and exposed at −70° C. to Kodak XAR5 film between Chronex Quanta III intensifying screens.

Figure 18D:
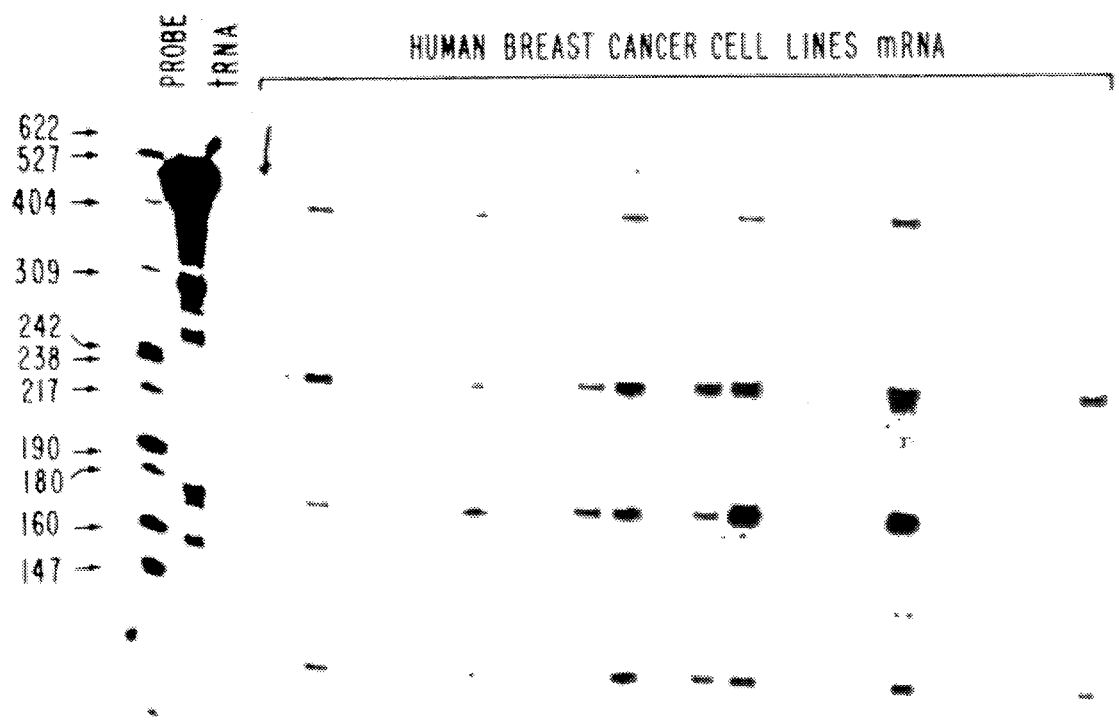

We have generated a 432 bp riboprobe derived from the gp30 $\beta$1 sequence (605–1073) that can specifically protect the different forms of the ligands. The probe contains the specific sequence for the $\beta$1 form. As shown in FIG. 18C, using the µ1 probe, four different fragments will be protected: $\beta$1:432 bp, $\alpha$:124 and 229 bp, $\beta$2:178 and 229 bp and $\beta$3:178 bp. Expression of the erbB-2 ligands in breast cancer cell lines is shown in FIG. 18D.

EXAMPLE 22

Transfection of gp30 cDNA into host cells

Figure 19:
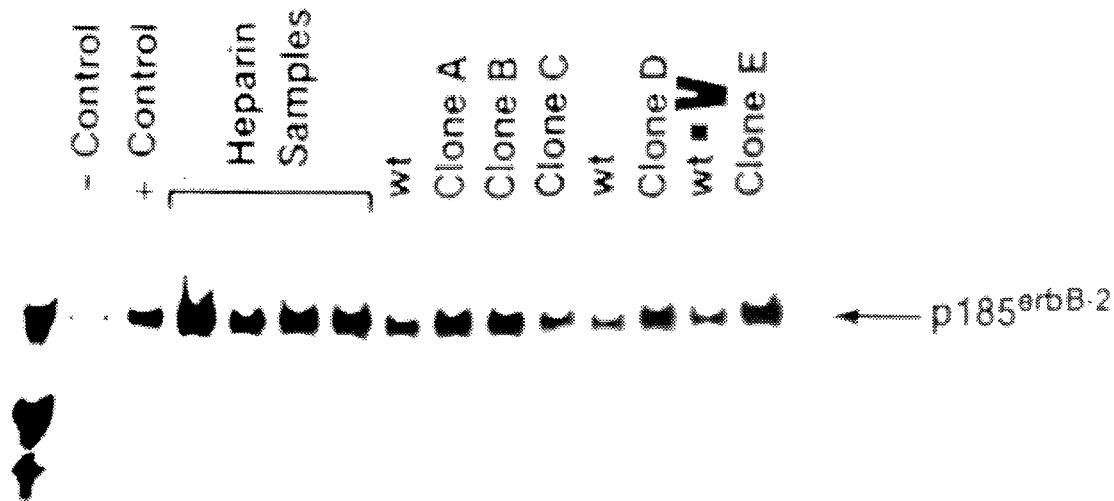
FIG. 19 shows induction of erbB-2 tyrosine phosphorylation using media from MCF-7/ligand expressing cells.

Full cDNA (approximately 2.4 kb) of the al form of gp30 was inserted into a pCHC6 expression vector. Then the erbB-2 ligand $\alpha$1 form was transfected into a variety of breast cancer cells including MCF-7 cells. After collecting media from the stable transfected cells, we performed erbB-2 phosphorylation assays using MDA-MB-453 cells as shown in FIG. 19. MDA-MB-453 cells were grown to 90% confluence in 24-well plate and treated at 37° C. with conditioned media from: untreated cells (−control); 100 µl of conditioned media×100 from MDA-MB-231 cells (+control); several batches of purified gp30 from conditioned media derived from MDA-MB-231 cells (heparin sepharose fractions); 100 µl of media from different clones from the MCF-7/ligand transfected cells (clone A, B, C, D and E); 100 µl of media from the MCF/-7 wild type cell line (wt); and 100 µl of media derived from MCF-7/vector alone cells (wt-V). After 30 minutes media was removed and cells were lysed in 100 µl of sample buffer. Proteins were then transferred to Hybond/ECL membrane for immunoblotting with an anti-phosphotyrosine antibody (UBI) and developed by the ECL method (Amersham).

As can be seen, un-concentrated media from the stable transfected cells induced tyrosine phosphorylation of the erbB-2 receptor. No phosphorylation was observed when conditioned media from MCF-7/WT or MCF-7/vector was used. Furthermore, we have shown that the secreted protein can bind to heparin as well as the secreted form from MDA-MB-231 cells. In conclusion, we have been able to construct a full length cDNA clone that translates into a biologically active ligand form.

EXAMPLE 23

Binding of gp30 to p185$^{erbB-2}$

The gp30 molecule may be purified using as a detection marker its ability to increase the level of tyrosine phosphorylation of p185$^{erbB-2}$ in living cells. The specificity of gp30 binding to p185$^{erbB-2}$ was demonstrated in several ways.

First, Scatchard analysis was performed using MDA-MB-453 cells and iodinated gp30. The incubation was performed in the presence of increasing concentrations of unlabelled gp30. Unbound [$^{125}$I]-gp30 was removed by three consecutive washes with binding buffer (DMEM/F12 1:1 and 0.1% BSA) and cells were solubilized in 0.1% SDS. Radioactivity was determined by using a gama-counter. The analysis showed a single class of high affinity binding sites ($K_d$=112 pM) on the surface of the cells.

Second, to examine the presumed direct interaction between the purified factor and p185$^{erbB-2}$, the method of covalent cross-linking was employed. The isolated gp30 was radiolabeled with iodine and separated from the free $^{125}$I by gel-filtration. The iodinated gp30 was incubated with MDA-MB-453 cells, and the bifunctional reagent ethylene glycolbis (EGS) was used to covalently cross-link gp30 to its receptor.

Figure 20A:
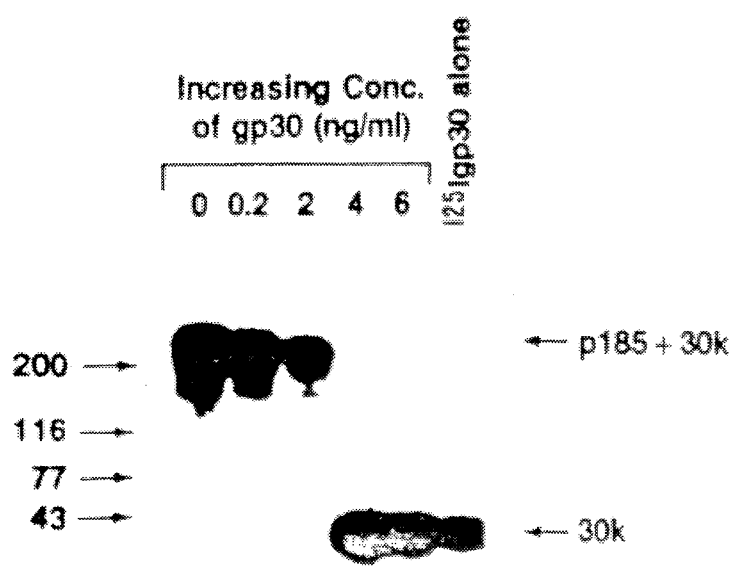
FIGS. 20A–B show binding and covalent cross-linking of radiolabeled gp30 to p185$^{erbB-2}$.

For the cross-linking experiments (FIG. 20), monolayers of MDA-MB-453 cells (300,000 cell/well) were used. Control cultures received an unlabelled gp30 in a dose dependent manner (0.1–10 nM). A control without cells, containing iodinated gp30 alone was performed as indicated (−) p185$^{erbB-2}$. After 1 hr at 4° C. the cells were transferred to incubation at room temperature and a chemical cross-linker (EGS) was added to some plates as indicated. Cell lysates were prepared after 45 minutes at 22° C. and subjected to immunoprecipitation with an anti-erbB-2 C-terminal polyclonal antibody and the precipitates were analyzed on a 6% SDS-PAGE. As shown in FIG. 20A, the results of this analysis showed that cross-linking of iodinated gp30 labeled one single band at an apparent molecular weight of 220 kDa which was immunoprecipitated with a specific anti-erbB-2 antibody.

Figure 20B:
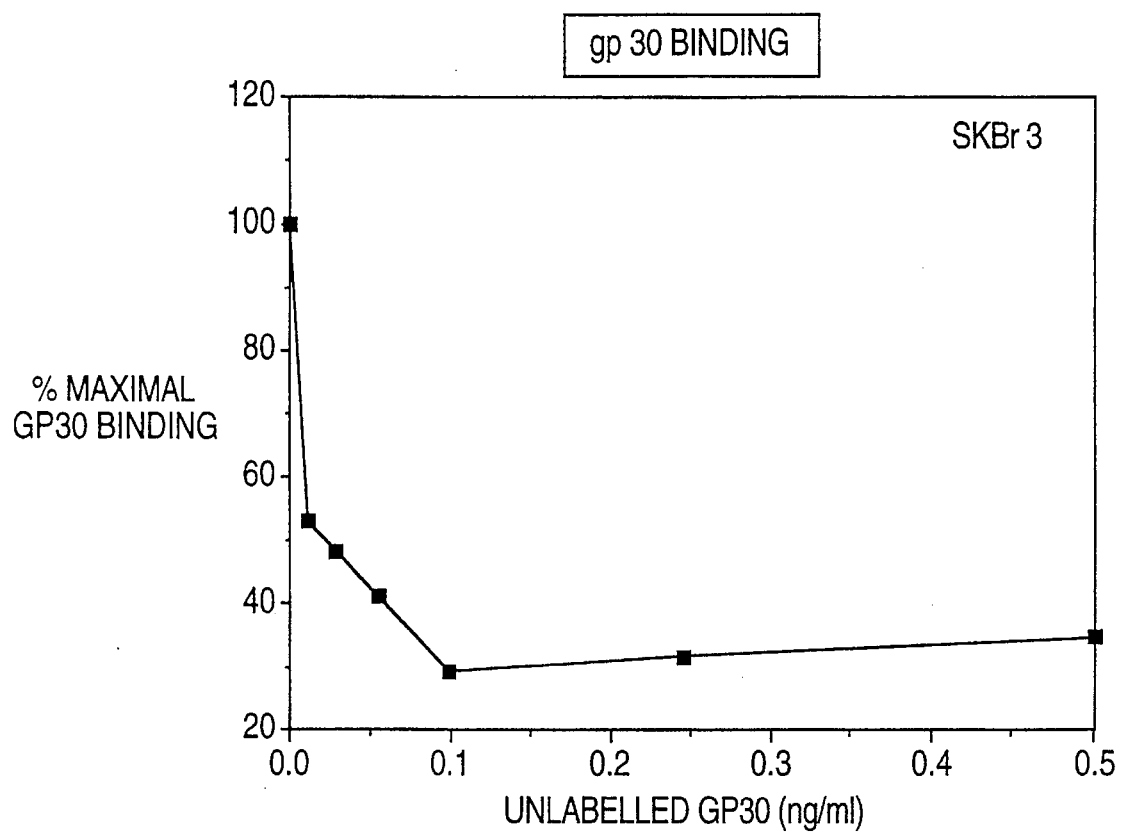
Figure 22A:
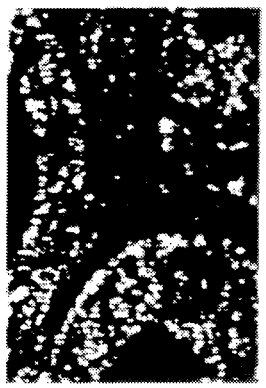
FIGS. 22A–F show immunostaining for the erbB-2 ligands in breast cancer tissue.
Figure 22B:
Figure 22C:
Figure 22D:
Figure 22E:
Figure 22F:

To determine the specificity of the cross-linking, unlabeled gp30 was added in a dose-dependent fashion, as shown in FIG. 20B. The results suggested that the 220 kDa protein is a 1:1 ratio complex of gp30 and p185$^{erbB-2}$. In the absence of the cross-linker no protein was detected, thus excluding the possibility of a non-covalent nature of interaction.

EXAMPLE 24

Antibodies to gp30 protein

Figure 21:
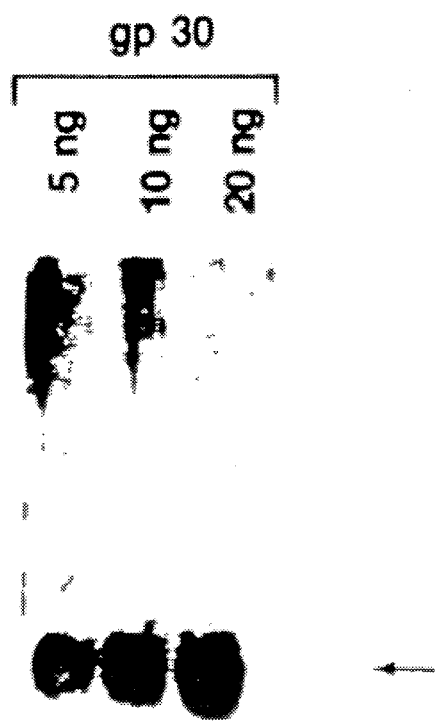
FIG. 21 shows Western Blot analysis of partially purified ligand.

Western blot analysis:

Western blots may be used to determine levels of gp30 protein. Several anti-peptide polyclonal antibodies have been generated, and the ability of those antibodies to recognize the ligand protein is shown in FIG. 21. Different concentrations of partially purified ligand were loaded into a 4–20% SDS-PAGE, in a dose fashion (5, 10 and 20 ng/well). The gel was transferred to the Hybond/ECL membrane. After transfer, the blot was blocked using 5% BSA (RIA grade). The specific antibody was added (1:10000) for 1–2 hrs at RT. After the incubation with a second antibody, the reaction was developed using the ECL method (Amersham). No cross-reactivity was observed when pre-immune serum was used after each treatment. Using this technique, cells may be tested for the presence of gp30 and the levels of gp30 in both conditioned media and cell lysates may be determined.

Two specific monoclonal anti-gp30 antibodies have been generated. These antibodies were developed by immunization of Balb/c mice with gp30 protein. Several hybridomas were identified and two were determined to be specific to gp30. This was determined by using several synthetic peptides derived from gp30 protein sequence. One of the monoclonal antibodies not only recognized gp30 protein but also recognized one of the synthetic peptides. The antibodies are specific for the erbB-2 ligands and do not cross-react with TGFα, EGF, Amphiregulin and the HB-EGF.

EXAMPLE 25

Development of an ELISA assay using anti-gp30 antibodies

We have preliminary evidence that gp30 and erbB-2 can interact in a paracrine fashion. We have shown that fibroblasts derived from human breast tumors (stroma) express gp30. Therefore, we can postulate a paracrine loop. Determination of the circulation levels of gp30 in breast cancer patients is important for the confirmation of the paracrine loop. ELISA and RIA assays may be used for detection of gp30 in serum samples from breast cancer patients. Both assays are a solid phase type assay (easy for large screening).

An ELISA assay has been developed in which two different polyclonal antibodies are used, one of them being biotinylated. For this assay, a 96 well plate is coated with one of the antibodies, and incubated with increasing concentration of ligand as a standard curve and/or serial dilutions of serum samples from patients. A second anti-ligand biotinylated antibody is used to determine the amount of ligand in each sample. The assay is developed by streptavidin-horseradish peroxidase.

EXAMPLE 26

Immunohistochemical staining for gp30 using different anti-peptide antibodies termed α1, α2 and α3

FIG. 22 shows imaging analysis on confocal microscopy of immunostaining of breast cancer paraffin sections using anti-erbB-2 ligand antibodies: FIG. 22A was immunostained with a polyclonal α1 antibody (Affinity purified antibody 1 µg/ml). FIG. 22B was immunostained with a monoclonal antibody (7B3-strait hybridoma supernatant. The antibody used in FIG. 22D was monoclonal antibody (10F10)-strait hybridoma supernatant. The slide shown in FIG. 22E was stained using 10F10 antibody in the presence of a blocking peptide (1 µg/ml). FIGS. 22C and F represents phase staining. An anti-rabbit or anti-mouse FITC conjugated second antibody was used to develop the staining.

As shown in FIG. 22, we have been able to obtain positive staining using several of the anti-ligand antibodies. Furthermore, we have shown that the staining was specific to ligand, since it was completely abolished by the addition of the respective peptides. Staining was observed intracellular in breast cancer epithelial cells and also in some adjacent fibroblasts.

EXAMPLE 27

In situ Hybridization To Detect gp30 Expression

In situ hybridization to gp30 mRNA is performed according to previously described protocols developed for other growth factors, using different riboprobes as described above to determine the expression of gp30 and/or the alternative spliced molecules. In brief, a pretreatment step for a paraffin embedded section is performed. All pre-ribonuclease washing steps are done with autoclaved polypropylene staining dishes. Sections are deparaffinized and rehydrated through alcohol series. Basic proteins are removed by incubation for 20 minutes in 0.2M HCl. Sections are treated with proteinase K and then incubated with glycine, washed and then acetylated in fresh acetic anhydride. Sections are washed and dehydrated through ethanol. Hybridization mix is added containing 5×10$^7$ cpm/ml of probe. Washes are performed and sections are exposed to NBT-2 emulsion for 1 to 3 weeks. After fixation sections are stained with hematoxylin-eosin and examined under the microscope.

EXAMPLE 28

RT-PCR from mRNA extracted from paraffin-embedded human tissues

In order to determine the level of gp30 expression and to compare between the different forms of the erbB-2 ligands (alternatively spliced molecules), PCR may be performed on RNA isolated from fixed sections. It has been previously shown that RNA extracted from formalin-fixed and paraffin embedded tissues can be reproducibly used as a substrate for PCR amplification. The hospital archives of human pathological tissues of biopsy or surgical origin are thus amenable to the analysis of expressed gp30.

In brief, RNA is prepared from the embedded tissue and cDNA fragments generated using reverse transcriptase and random hexamers. Specific primers covering a fragments of 900 nucleotides from the 5' and 3' end of gp30 cDNA may be used to search for specific cDNA by 30–35 rounds of PCR amplification. Southern blotting of selected negative and positive samples may be used to monitor the sensitivity of the assay.

PCR analysis:

Cells are treated and RNA is isolated. Primers located in the 5' and the 3' end of the cDNA are used, depending upon the sequence of interest. Sets of primers that can amplify fragments from 1.3 kb to 400 bp can easily be designed by the skilled worker from the sequences disclosed herein. Preferably, these sets cover the open reading frame of the active site of gp30 (the EGF-like domain). In addition some of the combinations may include the Immunoglobulin domain and the transmembrane domain. A test for specificity may be performed by cutting the product with a restriction enzyme that should yield two fragments of known size. XhoI will serve as a restriction enzyme for this purpose, since it is a unique restriction site present in all combinations of primers for gp30.

The primers shown in FIG. 23A have been derived from the α1 sequence and used to determine gp30 expression based on amplification of the sequence shown in FIG. 23B. A control is necessary to validate the results. A unique XhoI restriction site (shown in the sequence in FIG. 23B) that will generate two distinctive fragments from the product amplified with all the possible combinations of primers makes it possible to determine that the amplified fragment represents the specific gene of interest (gp30). An example of the results obtained are shown in FIG. 23C.

FIG. 23C shows amplification of a specific ligand PCR product from 20 μparaffin section from breast cancer cell lines. MCF-7 cells (A=negative control) and MDA-MB-231 cells (B=positive control), were used to determine the conditions of the isolation and the RT-PCR. After the isolation, RT-PCR was performed using two different sets of primers as described earlier. As can be seen in FIG. 23C (left panel), amplification using specific/β-actin probes (C) a band at 650 bp was obtained from both extractions, whereas with the erbB-2 ligand primers (D), amplification was seen at 900 bp only from the mRNA derived from the MDA-MB-231 cells. In addition, mRNA was isolated from different breast cancer tumor samples as shown in FIG. 23C (right panel), and a specific 900 bp fragment was amplified from a tumor sample (E) that was determined by RNAse protection assay to be positive. In order to determine that the amplified fragment was the gene of interest, a restriction enzyme digestion using Xho I was performed, and two expected fragments were generated (F), showing the specificity of the assay.

EXAMPLE 29

Modulation of the Invasive Phenotype of Breast Cancer Cells

Figure 24:
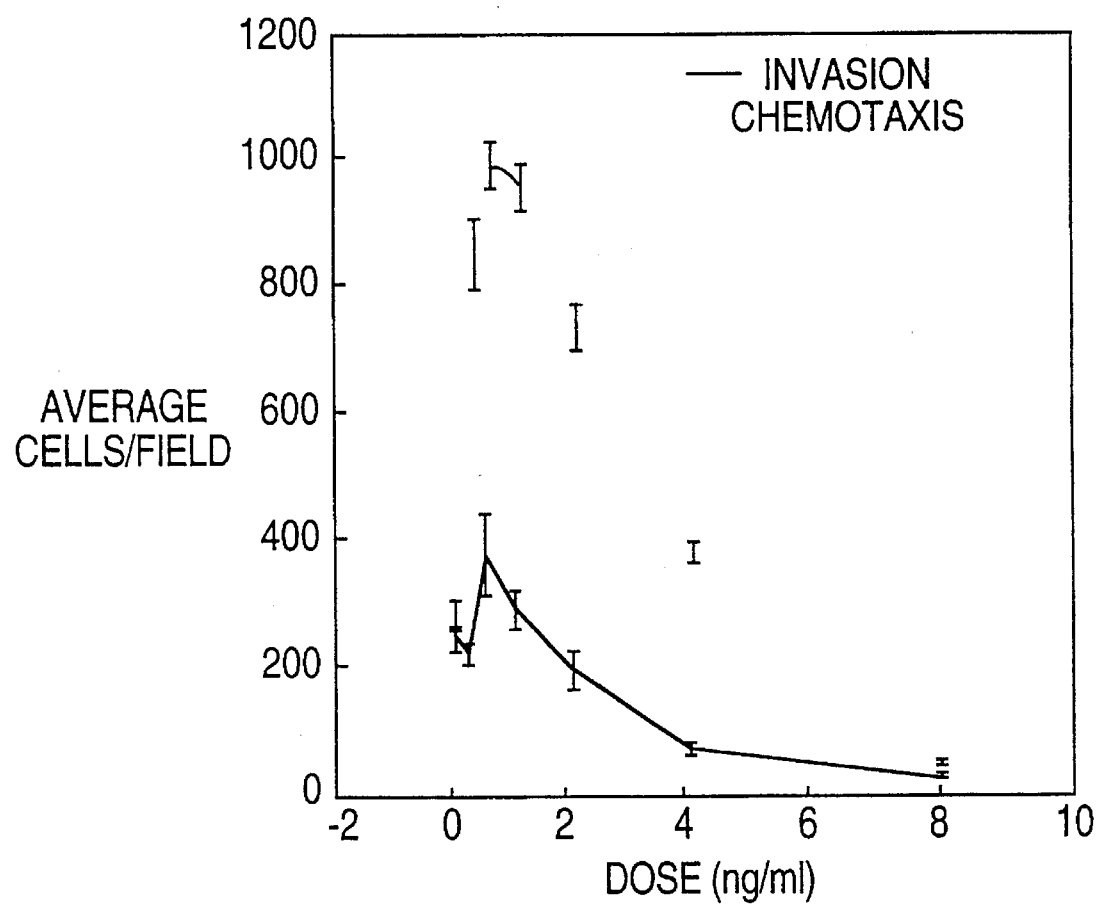
FIG. 24 shows gp30 effects on SKBR-3 cell invasion and migration in the Boyden chamber.

The constitutive effect of erbB-2 overexpression on human breast cancer cell invasiveness was examined for possible contribution to the poorer prognosis associated with this factor. erbB-2 positive cell lines (SKBR-3, BT-474 and MDA-MB-453) are all vimentin-negative, and accordingly show low constitutive invasiveness in the Boyden chamber assays for chemoinvasion and chemotaxis toward fibroblast conditioned media, as well as the Matrigel outgrowth assay. When these cells were treated with low concentrations of gp30, it was observed that induction of chemotaxis and chemoinvasion occurred in a dose-dependent manner which is similar to the growth response. FIG. 24 shows this effect for SKBR-3 cells. Cells were treated in the chamber with increasing concentrations of gp30, and incubated for 16 hours. Data points represent the mean ±SEM from triplicate filters in a representative experiment. Similar dose response curves have been obtained on at least two other occasions. gp30 effects on chemoinvasion and chemomigration were seen to various extents in the SKBR-3 and MDA-MB-453 cells, all of which contain erbB-2 receptors, the latter lacking measurable EGF-receptor. The specificity of this effect to the presence of gp30 was ascertained by blocking the effect in SKBr-3 cells with the addition of excess soluble erbB-2-ECD (data not shown).

EXAMPLE 30

The proliferation of BT-474 cells is regulated by 17β-estradiol and the erbB-2 ligand gp30

A significant fraction of breast cancer cells exhibit simultaneous expression of estrogen receptor (ER) and erbB-2. It has been reported that 17β-estradiol induces down-regulation of erbB-2 in such cells. In this example, we studied the interaction between these two receptors in tumor progression. As a model we used two cell lines: BT-474 and MDA-MB-361 cells.

In vitro growth effects of 17β-estradiol

To determine the effect of 17β-estradiol, anchorage-dependent growth assays were preformed using medium containing serum as control (fetal calf serum, FCS) or phenol red-free hormone-depleted serum (charcoal-stripped calf serum, CCS), with or without the addition of a $10^{-9}$M of 17β-estradiol. The depletion of hormones from the culture medium resulted in markedly slower cell proliferation, with BT-474 cells undergoing less than 1 doubling after 12 days. When 17β-estradiol was added to the medium the same proliferation rate as cells cultured with unprocessed serum was observed. Similarly, when a serum-free medium containing insulin, transferrin and selenium (HL-1, Ventrex) was used, BT-474 cells did not proliferate, but upon the addition of 17β-estradiol ($10^{-9}$M), the same doubling times as above were observed (data not shown). Similar results were obtained when MDA-MB-361 cells were used; their proliferation was markedly reduced by hormonal deprivation, and the addition of 17β-estradiol induced a dramatic proliferative response. In addition the growth of these cells was modulated when gp30 was used, as previously shown for SKBr-3 cells.

ER expression in BT-474 Cells modulated by erbB-2 ligand:

The effects of estradiol and gp30 on the expression of estrogen receptor and progesterone receptor (PgR) were studied in BT-474 cells. BT-474 cells were grown in IMEM containing 5% FCS. When the cells were 70–80% confluent, the media was changed to IMEM (phenol red-free) supplemented with 5% CCS for two days. Cells were treated for 24 hours with $10^{-9}$M estradiol, 0.02 to 2.0 ng/ml gp30, or 0.04 to 4.0 ng/ml p75. ER and PgR protein were assayed using enzyme immunoassay (Abbot Laboratories).

Figure 25A:
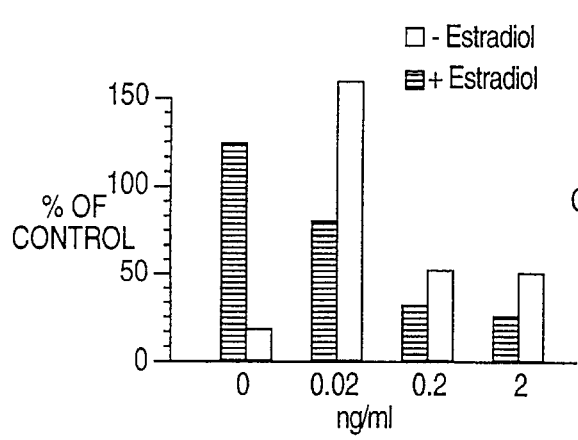
FIG. 25 shows the effects of estradiol and gp30 on estrogen and progesterone receptor expression.
Figure 25B:
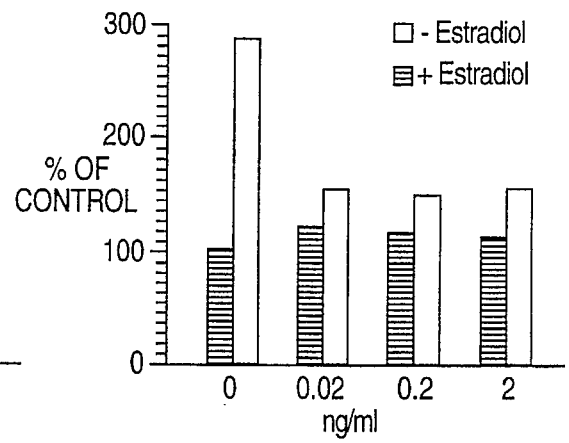

As shown in FIG. 25, treatment of cells with $10^{-9}$M estradiol for 24 hours resulted in a decline in ER protein of approximately 80% from a level of 35 fmol/mg protein in control cells to 6 fmol/mg protein in treated cells (left panel, 0 ng/ml gp30). Treatment of cells with estradiol resulted in 2.5-fold increase in PgR (fight panel, 0 ng/ml gp30). When cells were treated with concentrations of gp30 from 0.02 to 2.0 ng/ml for 24 hours there was a concentration dependent decrease in the level of ER. The higher concentration of gp30 resulted in a decrease in ER to approximately 20% of control values. gp30 had no effect on the level of PgR. When estradiol and gp30 were added simultaneously to cells, gp30 at low concentrations blocked the regulation of ER by estradiol. All concentrations of gp30 blocked estradiol induction of PgR.

Similar results were obtained when MCF-7 and/or MDA-MB-361 cells were used. Furthermore, identical results to those for protein determination, were obtained when mRNA levels were assay by an RNAse protection assay.

erbB-2 receptor expression in BT-474 cells as affected by 17β estradiol and gp30:

The levels of erbB-2 protein were determined using a radio-receptor assay which employs an iodinated antibody that binds to the extracellular domain of erbB-2 ($^{125}$I-4D5 antibody).

BT-474 cells were plated (20,000 cells/well) in 24 well plates in IMEM (phenol red-free) supplemented with 5% FCS. After 24 hrs the media was removed and replaced with media supplemented with 5% CCS with or without the addition of 17β-estradiol $10^{-9}$. After 48 hrs media were replaced with IMEM (phenol-red-free) supplemented with 5% CCS, in the presence or absence of increasing concentrations of gp30 (0.02, 0.2, 2.0 ng/ml) or p75 (0.04, 0.4, 4.0 ng/ml) and EGF (1.0 ng/ml) for additional 24 hrs. The erbB-2 protein levels were assayed using a competition binding assay using ($^{125}$I-4D5 or $^{125}$I-6E9) anti-erbB-2 antibodies against the extracellular domain.

Figure 26:
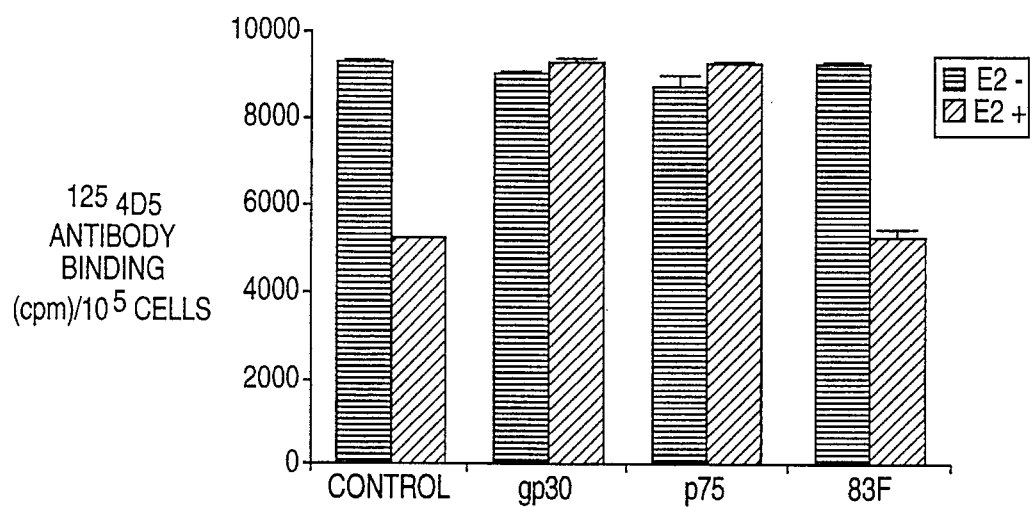
FIG. 26 shows erbB-2 receptor binding in BT-474 cells cultured in the presence of erbB-2 ligands.

Typical results are shown in FIG. 26. Overnight treatment of BT-474 cells with $10^{-9}$M 17β-estradiol, resulted in a decrease in antibody binding to erbB-2 of approximately 45%. 16 hrs treatment with gp30 (2 ng/ml) in hormone-depleted medium did not noticeably change the levels of erbB-2. However, this concentration of gp30 completely abrogated the down-regulating effect induced by 17β-estradiol (FIG. 26). gp30 concentrations as low as 0.02 ng/ml were sufficient to block the effect of 17β-estradiol. Epidermal growth factor (1 ng/ml) did not alter the levels of erbB-2 and, in contrast to gp30, did not interfere with the effect of 17β-estradiol on erbB-2 levels.

Similar results were obtained when MDA-MB-361 and/or MCF-7 cells were used. We have also shown by RNAse protection assays, that modulation at the mRNA level is similar to the modulation of the protein level.

EXAMPLE 31

Time course of erbB-2 down-regulation after estrogen addition and blockage by gp30

The level of the erbB-2 mRNA in gp30/estrogen treated cells, versus untreated cells and estrogen depleted cells may be determined over time. Estrogen is added for a length of time and the mRNA levels determined by Northern blot analysis. The difference observed after 72 hours should be enough to distinguish half-life changes, but shorter times of treatment may also be possible. Actinomycin D may be added to a concentration that has previously been shown to result in greater than 90% inhibition of [$^3$H]uridine incorporation in TCA precipitable material within 1 hour. The precise dose may be determined by the skilled worker, but initially a dose of 5μg/ml may be used. Total RNA is extracted at various intervals after the addition of Actinomycin D and subjected to Northern analysis, using fragments of the erbB-2 oncogene coding sequence as probes. Hybridization may be quantified by densitometry.

When estrogen was added to cultured cells like BT-474 cells, down-regulation at the mRNA level was observed at the first time point tested, i.e. 72 hrs after the addition of estrogen. An effect on erbB-2 mRNA level may be observed at an earlier time period after estrogen addition, and detection of down-regulation can be used to determine the optimal time and dose for gp30 effect. As a control for mRNA loading one may use both the GAPDH gene, which is a non-estrogen-induced transcript, and a pS2 probe which is an estrogen-induced transcript.

Regulation erbB-2 expression after treatment with gp30/estrogen and anti-estrogens may also be investigated by performing nuclear-run-on assays. These assays will detect expression at the mRNA level. The nuclear transcription run-on assay may be performed as follows. Isolated nuclei are incubated with $^{32}$P-UTP and unlabeled ATP, CTP, and GTP. The radiolabeled RNA transcripts are isolated and hybridized to an excess of denatured plasmid DNA immobilized on a nitrocellulose filter. The denatured plasmid used for the detection of specific transcripts will encode erbB-2 receptor, GAPDH and pS2. Autoradiography is analyzed by densitometry and the results are normalized for the number of nuclei or by comparison to the transcriptional level of GAPDH.

Summary

In brief, we have identified a novel polypeptide of 75 kDa that binds to the p185$^{erbB-2}$ receptor. The effects of p75 on cells with very high levels of erbB-2 were similar to the reported effects of the other ligand, gp30. In contrast to gp30, p75 appears to be specific for p185$^{erbB-2}$ receptor. Furthermore, we have provided evidence that cells that overexpress the erbB-2 receptor may also secrete one of its ligands, which is required for their proliferation, therefore implying an autocrine loop. We believe that manipulation of this and other erbB-2 ligands may turn out to have an important biological effect on growth of human neoplasia.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Having now described the invention, it will now be apparent to one of ordinary skill in the art that many changes and modifications can be made to the above embodiments without departing from the scope and spirit of the present invention.

Although the foregoing invention has been described in some detail by way of illustration and example for purposes of clarity of understanding, it will be obvious that certain changes and modifications may be practiced within the scope of the appended claims.

---

We claim:

1. A substantially pure protein, wherein said protein: reverses antiproliferative effect of soluble erbB-2 extracellular domain (ECD); corresponds to a protein which is obtained by elution of SK-BR-3 cancer cell conditioned media from an ECD affinity column at pH 3.0–3.5; inhibits cell proliferation and colony formation of cells which overexpress erbB-2; has apparent molecular weight as measured by SDS PAGE of about 75 kDa; is capable of inducing phosphorylation of p185$^{erbB-2}$; and does not bind EGFR.

2. A method of inhibiting the growth of cells in vitro which overexpress the oncogene erbB-2 or comprising treating said cells in vitro with an amount of the substantially pure protein according to claim 1 which is effective to inhibit the growth of said cells.

3. The method of claim 2, wherein said cells are adenocarcinoma cells.

4. A method of stimulating the growth of normal or malignant erbB-2 over-expressing cells in vitro comprising treating said cells in vitro with an amount of the substantially pure protein according to claim 1 which is sufficient to stimulate the growth of said cells.

5. The method of claim 4, wherein said cells are adenocarcinoma cells.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:1:

```
Lys Gly Lys Gly Lys Lys Xaa Glu Arg Gly Arg Gly Lys Lys Pro Gly
1               5                   10                  15
Ser Ala Ala Xaa Pro Gln Ser Pro Ala Leu Pro
            20              25
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Leu Val Leu Arg Cys Glu Thr Ser Ser Thr Tyr Ser Ser Leu Ala Phe
1               5                   10                  15
Lys Trp Phe Lys Asn Gly
            20
```

( 2 ) INFORMATION FOR SEQ ID NO:3:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Leu Gly Asn Asp Ser Ala Ser Ala Asn Ile Thr Ile Val Glu Ser Asn
1               5                   10                  15
Glu Ile Ile Thr Gly Asn Met Pro Ala
            20              25
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Asp Ser Gly Glu Tyr Met Cys Lys Val Ile Ser
1               5                   10
```

( 2 ) INFORMATION FOR SEQ ID NO:5:

( i ) SEQUENCE CHARACTERISTICS:
        ( A ) LENGTH: 23 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

Leu Val Lys Cys Ala Glu Lys Glu Lys Thr Phe Cys Val Asn Gly Gly
1               5                   10                  15

Glu Cys Phe Met Val Lys Asp
            20

( 2 ) INFORMATION FOR SEQ ID NO:6:

( i ) SEQUENCE CHARACTERISTICS:
( A ) LENGTH: 2164 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:6:

| | | | | | | |
|---|---|---|---|---|---|---|
| CCGATCCGAG | CCCTTGGACC | AAACTCGCCT | GCGCCGAGAG | CCGTCCGCGT | AGAGCGCTCC | 60 |
| GTCTCCGGCG | AGATGTCCGA | GCGCAAAGAA | GGCAGAGGCA | AAGGGAAGGG | CAAGAAGAAG | 120 |
| GAGCGAGGCT | CCGGCAAGAA | GCCGGAGTCC | GCGGCGGGCA | GCCAGAGCCC | AGCCTTGCCT | 180 |
| CCCCGATTGA | AAGAGATGAA | AAGCCAGGAA | TCGGCTGCAG | GTTCCAAACT | AGTCCTTCGG | 240 |
| TGTGAAACCA | GTTCTGAATA | CTCCTCTCTC | AGATTCAAGT | GGTTCAAGAA | TGGGAATGAA | 300 |
| TTGAATCGAA | AAACAAACC | ACAAAATATC | AAGATACAAA | AAAGCCAGG | GAAGTCAGAA | 360 |
| CTTCGCATTA | ACAAAGCATC | ACTGGCTGAT | TCTGGAGAGT | ATATGTGCAA | AGTGATCAGC | 420 |
| AAATTAGGAA | ATGACAGTGC | CTCTGCCAAT | ATCACCATCG | TGGAATCAAA | CGAGATCATC | 480 |
| ACTGGTATGC | CAGCCTCAAC | TGAAGGAGCA | TATGTGTCTT | CAGAGTCTCC | CATTAGAATA | 540 |
| TCAGTATCCA | CAGAAGGAGC | AAATACTTCT | TCATCTACAT | CTACATCCAC | CACTGGGACA | 600 |
| AGCCATCTTG | TAAAATGTGC | GGAGAAGGAG | AAAACTTTCT | GTGTGAATGG | AGGGGAGTGC | 660 |
| TTCATGGTGA | AAGACCTTTC | AAACCCCTCG | AGATACTTGT | GCAAGTGCCA | ACCTGGATTC | 720 |
| ACTGGAGCAA | GATGTACTGA | GAATGTGCCC | ATGAAAGTCC | AAAACCAAGA | AAAGGCGGAG | 780 |
| GAGCTGTACC | AGAAGAGAGT | GCTGACCATA | ACCGGCATCT | GCATCGCCCT | CCTTGTGGTC | 840 |
| GGCATCATGT | GTGTGGTGGC | CTACTGCAAA | ACCAAGAAAC | AGCGGAAAAA | GCTGCATGAC | 900 |
| CGTCTTCGGC | AGAGCCTTCG | GTCTGAACGA | AACAATATGA | TGAACATTGC | CAATGGGCCT | 960 |
| CACCATCCTA | ACCCACCCCC | CGAGAATGTC | CAGCTGGTGA | ATCAATACGT | ATCTAAAAAC | 1020 |
| GTCATCTCCA | GTGAGCATAT | TGTTGAGAGA | GAAGCAGAGA | CATCCTTTTC | CACCAGTCAC | 1080 |
| TATACTTCCA | CAGCCCATCA | CTCCACTACT | GTCACCCAGA | CTCCTAGCCA | CAGCTGGAGC | 1140 |
| AACGGACACA | CTGAAAGCAT | CCTTTCCGAA | AGCCACTCTG | TAATCGTGAT | GTCATCCGTA | 1200 |
| GAAAACAGTA | GGCACAGCAG | CCCAACTGGG | GGCCCAAGAG | GACGTCTTAA | TGGCACAGGA | 1260 |
| GGCCCTCGTG | AATGTAACAG | CTTCCTCAGG | CATGCCAGAG | AAACCCCTGA | TTCCTACCGA | 1320 |
| GACTCTCCTC | ATAGTGAAAG | GTATGTGTCA | GCCATGACCA | CCCCGGCTCG | TATGTCACCT | 1380 |
| GTAGATTTCC | ACACGCCAAG | CTCCCCCAAA | TCGCCCCCTT | CGGAAATGTC | TCCACCCGTG | 1440 |
| TCCAGCATGA | CGGTGTCCAT | GCCTTCCATG | GCGGTCAGCC | CCTTCATGGA | AGAAGAGAGA | 1500 |
| CCTCTACTTC | TCGTGACACC | ACCAAGGCTG | CGGGAGAAGA | AGTTTGACCA | TCACCCTCAG | 1560 |
| CAGTTCAGCT | CCTTCCACCA | CAACCCCGCG | CATGACAGTA | ACAGCCTCCC | TGCTAGCCCC | 1620 |
| TTGAGGATAG | TGGAGGATGA | GGAGTATGAA | ACGACCCAAG | AGTACGAGCC | AGCCCAAGAG | 1680 |
| CCTGTTAAGA | AACTCGCCAA | TAGCCGGCGG | GCCAAAAGAA | CCAAGCCCAA | TGGCCACATT | 1740 |

| | | | | | |
|---|---|---|---|---|---|
| GCTAACAGAT | TGGAAGTGGA | CAGCAACACA | AGCTCCCAGA | GCAGTAACTC | AGAGAGTGAA | 1800 |
| ACAGAAGATG | AAAGAGTAGG | TGAAGATACG | CCTTTCCTGG | GCATACAGAA | CCCCCTGGCA | 1860 |
| GCCAGTCTTG | AGGCAACACC | TGCCTTCCGC | CTGGCTGACA | GCAGGACTAA | CCCAGCAGGC | 1920 |
| CGCTTCTCGA | CACAGGAAGA | AATCCAGGCC | AGGCTGTCTA | GTGTAATTGC | TAACCAAGAC | 1980 |
| CCTATTGCTG | TATAAAACCT | AAATAAACAC | ATAGATTCAC | CTGTAAAACT | TTATTTTATA | 2040 |
| TAATAAAGTA | TTCCACCTTA | AATTAAACAA | TTTATTTTAT | TTAGCAGTT | CTGCAAATAG | 2100 |
| AAAACAGGAA | AAAACTTTT | ATAAATTAAA | TATATGTATG | TAAAAATGAA | AAAAAAAAA | 2160 |
| AAAA | | | | | | 2164 |

( 2 ) INFORMATION FOR SEQ ID NO:7:

( i ) SEQUENCE CHARACTERISTICS:
( A ) LENGTH: 2199 base pairs
( B ) TYPE: nucleic acid
( C ) STRANDEDNESS: both
( D ) TOPOLOGY: unknown ( i i ) MOLECULE TYPE: DNA (genomic)

( x i ) SEQUENCE DESCRIPTION: SEQ ID NO:7:

| | | | | | |
|---|---|---|---|---|---|
| GGGACAAACT | TTTCCCAAAC | CCGATCCGAG | CCCTTGGACC | AAACTCGCCT | GCGCCGAGAG | 60 |
| CCGTCCGCGT | AGAGCGCTCC | GTCTCCGGCG | AGATGTCCGA | GCGCAAAGAA | GGCAGAGGCA | 120 |
| AAGGGAAGGG | CAAGAAGAAG | GAGCGAGGCT | CCGGCAAGAA | GCCGGAGTCC | GCGGCGGGCA | 180 |
| GCCAGAGCCC | AGCCTTGCCT | CCCCAATTGA | AAGAGATGAA | AAGCCAGGAA | TCGGCTGCAG | 240 |
| GTTCCAAACT | AGTCCTTCGG | TGTGAAACCA | GTTCTGAATA | CTCCTCTCTC | AGATTCAAGT | 300 |
| GGTTCAAGAA | TGGGAATGAA | TTGAATCGAA | AAAACAAACC | ACAAATATC | AAGATACAAA | 360 |
| AAAAGCCAGG | GAAGTCAGAA | CTTCGCATTA | ACAAAGCATC | ACTGGCTGAT | TCTGGAGAGT | 420 |
| ATATGTGCAA | AGTGATCAGC | AAATTAGGAA | ATGACAGTGC | CTCTGCCAAT | ATCACCATCG | 480 |
| TGGAATCAAA | CGAGATCATC | ACTGGTATGC | CAGCCTCAAC | TGAAGGAGCA | TATGTGTCTT | 540 |
| CAGAGTCTCC | CATTAGAATA | TCAGTATCCA | CAGAAGGAGC | AAATACTTCT | TCATCTACAT | 600 |
| CTACATCCAC | CACTGGGACA | AGCCATCTTG | TAAAATGTGC | GGAGAAGGAG | AAAACTTTCT | 660 |
| GTGTGAATGG | AGGGGAGTGC | TTCATGGTGA | AAGACCTTTC | AAACCCCTCG | AGATACTTGT | 720 |
| GCAAGTGCCC | AAATGAGTTT | ACTGGTGATC | GCTGCCAAAA | CTACGTAATG | GCCAGCTTCT | 780 |
| ACAAGCATCT | TGGGATTGAA | TTTATGGAGG | CGGAGGAGCT | GTACCAGAAG | AGAGTGCTGA | 840 |
| CCATAACCGG | CATCTGCATC | GCCCTCCTTG | TGGTCGGCAT | CATGTGTGTG | GTGGCCTACT | 900 |
| GCAAAACCAA | GAAACAGCGG | AAAAAGCTGC | ATGACCGTCT | TCGGCAGAGC | CTTCGGTCTG | 960 |
| AACGAAACAA | TATGATGAAC | ATTGCCAATG | GGCCTCACCA | TCCTAACCCA | CCCCCCGAGA | 1020 |
| ATGTCCAGCT | GGTGAATCAA | TACGTATCTA | AAAACGTCAT | CTCCAGTGAG | CATATTGTTG | 1080 |
| AGAGAGAAGC | AGAGACATCC | TTTTCCACCA | GTCACTATAC | TTCCACAGCC | CATCACTCCA | 1140 |
| CTACTGTCAC | CCAGACTCCT | AGCCACAGCT | GGAGCAACGG | ACACACTGAA | AGCATCCTTT | 1200 |
| CCGAAAGCCA | CTCTGTAATC | GTGATGTCAT | CCGTAGAAAA | CAGTAGGCAC | AGCAGCCCAA | 1260 |
| CTGGGGGCCC | AAGAGGACGT | CTTAATGGCA | CAGGAGGCCC | TCGTGAATGT | AACAGCTTCC | 1320 |
| TCAGGCATGC | CAGAGAAACC | CCTGATTCCT | ACCGAGACTC | TCCTCATAGT | GAAAGGTATG | 1380 |
| TGTCAGCCAT | GACCACCCCG | GCTCGTATGT | CACCTGTAGA | TTTCCACACG | CCAAGCTCCC | 1440 |
| CCAAATCGCC | CCCTTCGGAA | ATGTCTCCAC | CCGTGTCCAG | CATGACGGTG | TCCATGCCTT | 1500 |
| CCATGGCGGT | CAGCCCCTTC | ATGGAAGAAG | AGAGACCTCT | ACTTCTCGTG | ACACCACCAA | 1560 |

```
GGCTGCGGGA  GAAGAAGTTT  GACCATCACC  CTCAGCAGTT  CAGCTCCTTC  CACCACAACC    1620

CCGCGCATGA  CAGTAACAGC  CTCCCTGCTA  GCCCCTTGAG  GATAGTGGAG  GATGAGGAGT    1680

ATGAAACGAC  CCAAGAGTAC  GAGCCAGCCC  AAGAGCCTGT  TAAGAAACTC  GCCAATAGCC    1740

GGCGGGCCAA  AAGAACCAAG  CCCAATGGCC  ACATTGCTAA  CAGATTGGAA  GTGGACAGCA    1800

ACACAAGCTC  CCAGAGCAGT  AACTCAGAGA  GTGAAACAGA  AGATGAAAGA  GTAGGTGAAG    1860

ATACGCCTTT  CCTGGGCATA  CAGAACCCCC  TGGCAGCCAG  TCTTGAGGCA  ACACCTGCCT    1920

TCCGCCTGGC  TGACAGCAGG  ACTAACCCAG  CAGGCCGCTT  CTCGACACAG  GAAGAAATCC    1980

AGGCCAGGCT  GTCTAGTGTA  ATTGCTAACC  AAGACCCTAT  TGCTGTATAA  AACCTAAATA    2040

AACACATAGA  TTCACCTGTA  AAACTTTATT  TTATATAATA  AAGTATTCCA  CCTTAAATTA    2100

AACAATTTAT  TTTATTTTAG  CAGTTCTGCA  AATAGAAAAC  AGGAAAAAAA  CTTTTATAAA    2160

TTAAATATAT  GTATGTAAAA  ATGAAAAAAA  AAAAAAAA                              2199
```

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: unknown ( i i ) MOLECULE TYPE: DNA (genomic)

( x i ) SEQUENCE DESCRIPTION: SEQ ID NO:8:

```
GAATGTGCCC  ATGAAAGTCC  AAAACCA                                             27
```

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: unknown ( i i ) MOLECULE TYPE: DNA (genomic)

( x i ) SEQUENCE DESCRIPTION: SEQ ID NO:9:

```
AGAAAAGGCG  GAGGAGCT                                                        18
```

( 2 ) INFORMATION FOR SEQ ID NO:10:

( i ) SEQUENCE CHARACTERISTICS:
        ( A ) LENGTH: 61 base pairs
        ( B ) TYPE: nucleic acid
        ( C ) STRANDEDNESS: both
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 1..24

( i x ) FEATURE:
        ( A ) NAME/KEY: misc_feature
        ( B ) LOCATION: 49..61

( i x ) FEATURE:
        ( A ) NAME/KEY: misc_feature
        ( B ) LOCATION: 1..24

( x i ) SEQUENCE DESCRIPTION: SEQ ID NO:10:

```
CTACGTAATG  GCCCAGCTTC  TACAAGCATC  TTGGGATTGA  ATTTATGGAG  GCGGAGGAGC    60
```

T                                                                                                                    6 1

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:11:

```
AAR  GGN  AAR  GGN  AAR  AAR  NN                                                                                     20
Lys  Gly  Lys  Gly  Lys  Lys
 1                   5
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Lys  Gly  Lys  Gly  Lys  Lys
 1                   5
```

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: unknown ( i i ) MOLECULE TYPE: DNA (genomic)

( i v ) ANTI-SENSE: YES ( x i ) SEQUENCE DESCRIPTION: SEQ ID NO:13:

```
TTYCCNTTYC  CNTTYTTYNN                                                                                               20
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:14:

```
GGN  GAR  UAY  AUG  UGY  AAR  GU                                                                                     20
Gly  Glu  Tyr  Met  Cys  Lys  Val
 1                   5
```

( 2 ) INFORMATION FOR SEQ ID NO:15:

( i ) SEQUENCE CHARACTERISTICS:

(A) LENGTH: 7 amino acids
(B) TYPE: amino acid
(D) TOPOLOGY: linear (i i) MOLECULE TYPE: protein (x i) SEQUENCE DESCRIPTION: SEQ ID NO:15:

| Gly | Glu | Tyr | Met | Cys | Lys | Val |
|-----|-----|-----|-----|-----|-----|-----|
| 1   |     |     |     | 5   |     |     |

(2) INFORMATION FOR SEQ ID NO:16:

(i) SEQUENCE CHARACTERISTICS:
    (A) LENGTH: 20 base pairs
    (B) TYPE: nucleic acid
    (C) STRANDEDNESS: both
    (D) TOPOLOGY: unknown (i i) MOLECULE TYPE: DNA (genomic)

(i v) ANTI-SENSE: YES (x i) SEQUENCE DESCRIPTION: SEQ ID NO:16:

CCNCTYATRT ACACRTTYCA                                                        20

(2) INFORMATION FOR SEQ ID NO:17:

(i) SEQUENCE CHARACTERISTICS:
    (A) LENGTH: 483 base pairs
    (B) TYPE: nucleic acid
    (C) STRANDEDNESS: both
    (D) TOPOLOGY: unknown (i i) MOLECULE TYPE: DNA (genomic)

(i x) FEATURE:
    (A) NAME/KEY: CDS
    (B) LOCATION: 1..483

(x i) SEQUENCE DESCRIPTION: SEQ ID NO:17:

| AAA | GGG | AAG | GGC | AAG | AAG | AAG | GAG | CGA | GGC | TCC | GGC | AAG | AAG | CCG | GAG | 48 |
| Lys | Gly | Lys | Gly | Lys | Lys | Lys | Glu | Arg | Gly | Ser | Gly | Lys | Lys | Pro | Glu |    |
| 1   |     |     |     | 5   |     |     |     |     | 10  |     |     |     |     | 15  |     |    |

| TCC | GCG | GCG | GGC | AGC | CAG | AGC | CCA | GCC | TTG | CCT | CCC | CGA | TTG | AAA | GAG | 96 |
| Ser | Ala | Ala | Gly | Ser | Gln | Ser | Pro | Ala | Leu | Pro | Pro | Arg | Leu | Lys | Glu |    |
|     |     |     | 20  |     |     |     |     | 25  |     |     |     |     | 30  |     |     |    |

| ATG | AAA | AGC | CAG | GAA | TCG | GCT | GCA | GGT | TCC | AAA | CTA | GTC | CTT | CGG | TGT | 144 |
| Met | Lys | Ser | Gln | Glu | Ser | Ala | Ala | Gly | Ser | Lys | Leu | Val | Leu | Arg | Cys |     |
|     |     | 35  |     |     |     |     | 40  |     |     |     |     | 45  |     |     |     |     |

| GAA | ACC | AGT | TCT | GAA | TAC | TCC | TCT | CTC | AGA | TTC | AAG | TGG | TTC | AAG | AAT | 192 |
| Glu | Thr | Ser | Ser | Glu | Tyr | Ser | Ser | Leu | Arg | Phe | Lys | Trp | Phe | Lys | Asn |     |
|     | 50  |     |     |     |     | 55  |     |     |     |     | 60  |     |     |     |     |     |

| GGG | AAT | GAA | TTG | AAT | CGA | AAA | AAC | AAA | CCA | CAA | AAT | ATC | AAG | ATA | CAA | 240 |
| Gly | Asn | Glu | Leu | Asn | Arg | Lys | Asn | Lys | Pro | Gln | Asn | Ile | Lys | Ile | Gln |     |
| 65  |     |     |     |     | 70  |     |     |     |     | 75  |     |     |     |     | 80  |     |

| AAA | AAG | CCA | GGG | AAG | TCA | GAA | CTT | CGC | ATT | AAC | AAA | GCA | TCA | CTG | GCT | 288 |
| Lys | Lys | Pro | Gly | Lys | Ser | Glu | Leu | Arg | Ile | Asn | Lys | Ala | Ser | Leu | Ala |     |
|     |     |     |     | 85  |     |     |     |     | 90  |     |     |     |     | 95  |     |     |

| GAT | TCT | GGA | GAG | TAT | ATG | TGC | AAA | GTG | ATC | AGC | AAA | TTA | GGA | AAT | GAC | 336 |
| Asp | Ser | Gly | Glu | Tyr | Met | Cys | Lys | Val | Ile | Ser | Lys | Leu | Gly | Asn | Asp |     |
|     |     |     | 100 |     |     |     |     | 105 |     |     |     |     | 110 |     |     |     |

| AGT | GCC | TCT | GCC | AAT | ATC | ACC | ATC | GTG | GAA | TCA | AAC | GAG | ATC | ATC | ACT | 384 |
| Ser | Ala | Ser | Ala | Asn | Ile | Thr | Ile | Val | Glu | Ser | Asn | Glu | Ile | Ile | Thr |     |
|     |     | 115 |     |     |     |     | 120 |     |     |     |     | 125 |     |     |     |     |

| GGT | ATG | CCA | GCC | TCA | ACT | GAA | GGA | GCA | TAT | GTG | TCT | TCA | GAG | TCT | CCC | 432 |
| Gly | Met | Pro | Ala | Ser | Thr | Glu | Gly | Ala | Tyr | Val | Ser | Ser | Glu | Ser | Pro |     |
|     | 130 |     |     |     |     | 135 |     |     |     |     | 140 |     |     |     |     |     |

```
ATT  AGA  ATA  TCA  GTA  TCC  ACA  GAA  GGA  GAG  TAT  ATG  TGC  AAA  GTG  ATC        480
Ile  Arg  Ile  Ser  Val  Ser  Thr  Glu  Gly  Glu  Tyr  Met  Cys  Lys  Val  Ile
145                      150                      155                      160

AGC                                                                                   483
Ser
```

( 2 ) INFORMATION FOR SEQ ID NO:18:

( i ) SEQUENCE CHARACTERISTICS:
        ( A ) LENGTH: 161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Lys  Gly  Lys  Gly  Lys  Lys  Lys  Glu  Arg  Gly  Ser  Gly  Lys  Lys  Pro  Glu
1                        5                        10                       15

Ser  Ala  Ala  Gly  Ser  Gln  Ser  Pro  Ala  Leu  Pro  Pro  Arg  Leu  Lys  Glu
               20                        25                       30

Met  Lys  Ser  Gln  Glu  Ser  Ala  Ala  Gly  Ser  Lys  Leu  Val  Leu  Arg  Cys
          35                        40                       45

Glu  Thr  Ser  Ser  Glu  Tyr  Ser  Ser  Leu  Arg  Phe  Lys  Trp  Phe  Lys  Asn
     50                        55                       60

Gly  Asn  Glu  Leu  Asn  Arg  Lys  Asn  Lys  Pro  Gln  Asn  Ile  Lys  Ile  Gln
65                       70                       75                       80

Lys  Lys  Pro  Gly  Lys  Ser  Glu  Leu  Arg  Ile  Asn  Lys  Ala  Ser  Leu  Ala
               85                        90                       95

Asp  Ser  Gly  Glu  Tyr  Met  Cys  Lys  Val  Ile  Ser  Lys  Leu  Gly  Asn  Asp
               100                       105                      110

Ser  Ala  Ser  Ala  Asn  Ile  Thr  Ile  Val  Glu  Ser  Asn  Glu  Ile  Ile  Thr
          115                       120                      125

Gly  Met  Pro  Ala  Ser  Thr  Glu  Gly  Ala  Tyr  Val  Ser  Ser  Glu  Ser  Pro
     130                       135                      140

Ile  Arg  Ile  Ser  Val  Ser  Thr  Glu  Gly  Glu  Tyr  Met  Cys  Lys  Val  Ile
145                       150                      155                      160

Ser
```